US012285757B2

(12) United States Patent
Ladtkow et al.

(10) Patent No.: US 12,285,757 B2
(45) Date of Patent: *Apr. 29, 2025

(54) CENTRIFUGAL FLUID SEPARATION DEVICE

(71) Applicant: Terumo BCT, Inc., Lakewood, CO (US)

(72) Inventors: James R. Ladtkow, Broomfield, CO (US); Dennis J. Hlavinka, Arvada, CO (US); Thomas J. Felt, Boulder, CO (US); Andrew Gloor, Broomfield, CO (US); Jesse Janzen, Broomfield, CO (US); Taylor Polodna, Golden, CO (US); Luke Edwin Storm, Broomfield, CO (US)

(73) Assignee: Terumo BCT, Inc., Lakewood, CO (US)

( * ) Notice: Subject to any disclaimer, the term of this patent is extended or adjusted under 35 U.S.C. 154(b) by 361 days.

This patent is subject to a terminal disclaimer.

(21) Appl. No.: 17/951,150

(22) Filed: Sep. 23, 2022

(65) Prior Publication Data
US 2023/0015292 A1    Jan. 19, 2023

Related U.S. Application Data

(63) Continuation of application No. 15/719,224, filed on Sep. 28, 2017, now Pat. No. 11,478,792.
(Continued)

(51) Int. Cl.
*B01L 3/00* (2006.01)
*A61M 1/02* (2006.01)
(Continued)

(52) U.S. Cl.
CPC ..... *B01L 3/502738* (2013.01); *A61M 1/0231* (2014.02); *A61M 1/029* (2013.01);
(Continued)

(58) Field of Classification Search
CPC ........ A61M 1/36224; A61M 1/362262; A61M 1/362266; A61M 1/362265;
(Continued)

(56) References Cited

U.S. PATENT DOCUMENTS

| 6,039,711 | A | 3/2000 | Headley et al. |
| 6,063,589 | A | 5/2000 | Kellogg et al. |

(Continued)

FOREIGN PATENT DOCUMENTS

| EP | 2030686 A3 | 9/2009 |
| JP | 2003270252 A | 9/2003 |

(Continued)

OTHER PUBLICATIONS

Selvaganapathy, P. et al., Electrothermally Actuated Inline Microfludic Valve, 1 Department of Electrical Engineering and Computer Science, Center for Wireless Integrated Microsystems, University of Michigan, Ann Arbor, VII 48109-2122, Sensors and Actuators A 104 (2003) pp. 275-282.

(Continued)

*Primary Examiner* — Patrick Orme
(74) *Attorney, Agent, or Firm* — Harness, Dickey & Pierce, P.L.C.

(57) ABSTRACT

A modular cassette is provided for separating a composite fluid into at least two component parts thereof during centrifugation. The modular cassette includes: a housing defining a fluid inlet, a fluid outlet, and a chamber for fluid separation; a fluidic channel configured to provide fluid communication between at least two components of the modular cassette; a heat expanding valve including: a flow pathway including undulations configured to facilitate closing of the fluidic channel, wherein the heat expanding valve occludes one or more of the undulations of the flow pathway (Continued)

to close the fluidic channel; and a heating element configured to actuate the heat expanding valve.

11 Claims, 27 Drawing Sheets

Related U.S. Application Data

(60) Provisional application No. 62/500,021, filed on May 2, 2017, provisional application No. 62/416,519, filed on Nov. 2, 2016, provisional application No. 62/403,312, filed on Oct. 3, 2016.

(51) Int. Cl.

| | | |
|---|---|---|
| *A61M 1/36* | (2006.01) | |
| *A61M 1/38* | (2006.01) | |
| *B04B 5/04* | (2006.01) | |
| *B04B 7/08* | (2006.01) | |
| *F16K 99/00* | (2006.01) | |
| *G01N 1/40* | (2006.01) | |
| *G01N 33/49* | (2006.01) | |
| *G01N 35/00* | (2006.01) | |
| *B04B 9/14* | (2006.01) | |

(52) U.S. Cl.
CPC .... *A61M 1/36224* (2022.05); *A61M 1/36226* (2022.05); *A61M 1/362262* (2022.05); *A61M 1/362265* (2022.05); *A61M 1/362266* (2022.05); *A61M 1/3693* (2013.01); *B04B 5/0428* (2013.01); *B04B 5/0442* (2013.01); *B04B 7/08* (2013.01); *F16K 99/0032* (2013.01); *F16K 99/0044* (2013.01); *G01N 1/4077* (2013.01); *G01N 33/491* (2013.01); *G01N 35/00069* (2013.01); *A61M 1/38* (2013.01); *A61M 2205/128* (2013.01); *A61M 2205/3653* (2013.01); *B01L 2300/0803* (2013.01); *B01L 2300/0864* (2013.01); *B01L 2400/0409* (2013.01); *B01L 2400/0677* (2013.01); *B04B 2005/045* (2013.01); *B04B 2005/0464* (2013.01); *B04B 2009/143* (2013.01); *F16K 2099/0086* (2013.01); *G01N 2035/00267* (2013.01)

(58) Field of Classification Search
CPC .. A61M 1/0231; A61M 1/029; A61M 1/3693; A61M 1/38; A61M 2205/128; A61M 2205/3653; B01L 3/502738; B01L 2300/0803; B01L 2300/0864; B01L 2400/0409; B01L 2400/0677; B04B 5/0428; B04B 5/0442; B04B 7/08; B04B 2005/045; B04B 2005/0464; B04B 2009/143; F16K 99/0032; F16K 99/0044; F16K 2099/0086; G01N 1/4077; G01N 33/491; G01N 35/00069; G01N 2035/00267

See application file for complete search history.

(56) References Cited

U.S. PATENT DOCUMENTS

| | | |
|---|---|---|
| 6,302,134 B1 | 10/2001 | Kellogg et al. |
| 6,334,842 B1 | 1/2002 | Hlavinka et al. |
| 6,548,788 B2 | 4/2003 | Kellogg et al. |
| 6,632,399 B1 | 10/2003 | Kellog et al. |
| 6,736,768 B2 | 5/2004 | Felt et al. |
| 7,094,196 B2 | 8/2006 | Felt et al. |
| 7,322,254 B2 | 1/2008 | Bedingham et al. |
| 7,981,385 B2 | 7/2011 | Park et al. |
| 8,221,704 B2 | 7/2012 | Park et al. |
| 11,478,792 B2 * | 10/2022 | Ladtkow ............. F16K 99/0032 |
| 2003/0044322 A1 | 3/2003 | Andersson et al. |
| 2003/0049174 A1 | 3/2003 | Ganesan |
| 2006/0226057 A1 | 10/2006 | Robinson et al. |
| 2010/0055766 A1 | 3/2010 | Hwang et al. |
| 2010/0186839 A1 | 7/2010 | Namkoong et al. |
| 2011/0238029 A1 | 9/2011 | Biset et al. |
| 2013/0029370 A1 | 1/2013 | Coelho |
| 2014/0066281 A1 | 3/2014 | Weasler et al. |
| 2014/0147862 A1 | 5/2014 | Kim et al. |
| 2015/0064774 A1 | 3/2015 | Moon et al. |
| 2015/0244932 A1 | 8/2015 | Kang et al. |

FOREIGN PATENT DOCUMENTS

| | | |
|---|---|---|
| JP | 2014103966 A | 6/2014 |
| WO | 1997021090 A1 | 6/1997 |
| WO | 2005107947 A1 | 11/2005 |

OTHER PUBLICATIONS

International Searching Authority, International Search Report and Written Opinion, Dec. 6, 2017; 16 pages.
International Searching Authority, International Preliminary Report on Patentability, Apr. 18, 2019, 10 pages.
Seom Seok Lee et al., "Fully Integrated Lab-on-a Disc for Simultaneous Analysis of Biochemistry and Immunoassay from Whole Blood", The Royal Society of Chemistry 2011, vol. 11, pp. 70-78.
Seom Seok Lee et al, "A Fully Automated Immunoassay from Whole Blood on a Disc", The Royal Society of Dhemistry 2009, vol. 9, pp. 1548-1555.
Daniel Kirby et al., "Rapid and Cost-Effective Enumeration of Rare Cancer Cells from Whole Blood by Low-Loss Dentrifugo-Magnetophoretic Purification Under Stopped-Flow Conditions", Journal of the International Society for Advancementof Cytometry, 2015, pp. 74-80.
Hyundoo Hwang et al, "Lab-on-a-Disc for Simultaneous Determination of Nutrients in Water", Analytical Chemistry 2013, vol. 85, pp. 2954-2960.
Yoon-Kyoung Cho et al., "One-step Pathogen Specific DMA Extraction from Whole Blood on a Centrifugal Vlicrofluidic Device", The Royal Society of Chemistry 2007, 3 pages.
GE Healthcare Life Sciences, "Isolation of Mononuclear Cells, Methodology and Applications", Uppsala, Sweden, Aug. 2014, 20 pages.
A. Boyum et al, "Separation of Leucocytes: Improved Cell Purity by Fine Adjustments of Gradient Medium Density and Osmolality", The Scandinavian Journal of Clinical & Laboratory Investigation vol. 34, 1991, pp. 697-712.
A. Boyum, "Isolation of Lymphocytes, Granulocytes and Macrophages", The Scandinavian Journal of Clinical & Laboratory Investigation vol. 5, Supplemental 5, 1976, pp. 9-15.
A. Boyum, Isolation of Mononuclear Cells and Granulocytes from Human Blood, The Scandinavian Journal of Clinical & Laboratory Investigation vol. 21, Supplemental 97, 1968, pp. 77-89.
Arne Boyum, "Separation of Leucocytes from Blood and Bone Marrow", The Scandinavian Journal of Clinical & Laboratory Investigation vol. 21, Supplemental 97, 1968, pp. 30-50.
Jones, Alan L., "Past, Present, and Future Uses of Blood Cell Separation in Immunohenatology", Journal of Clinical pheresis 4:170,1988,14 pages.
Official Action for India Patent Application No. 201947016428, dated Jun. 1, 2021. 7 pages.
Official Action for China Patent Application No. 201780071790.4, dated Jan. 17, 2022, 8 pages.
Official Action for China Patent Application No. 201780071790.4, dated May 6, 2021, 11 pages.

* cited by examiner

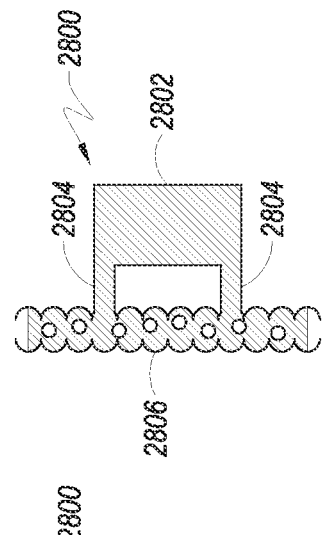
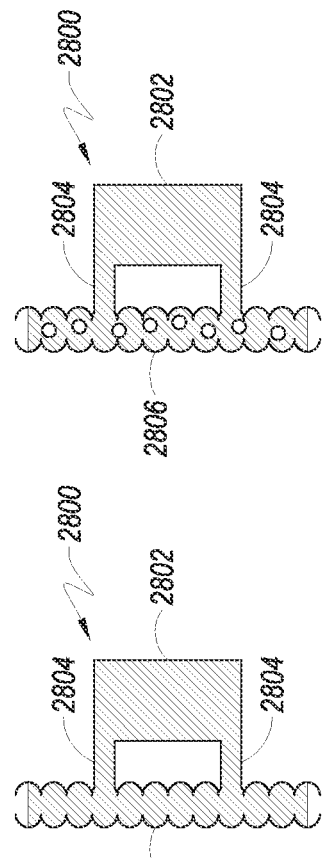
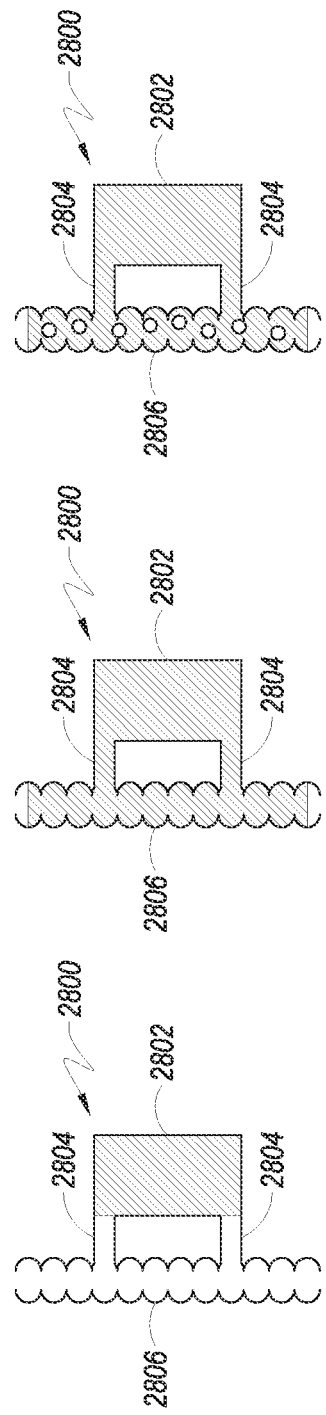
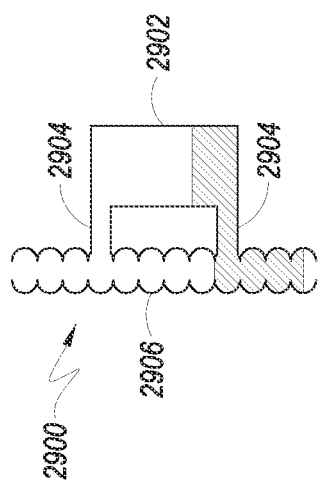
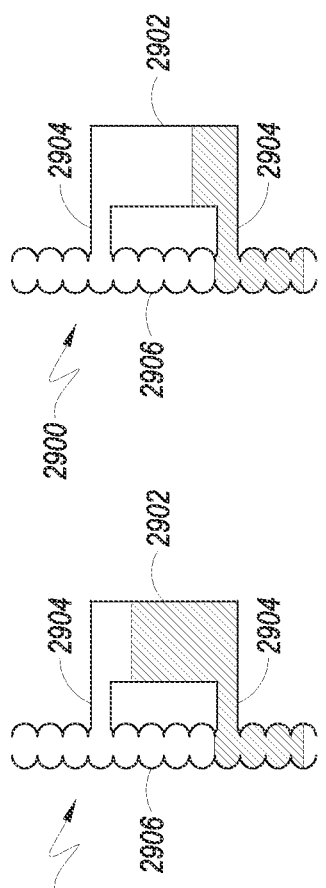
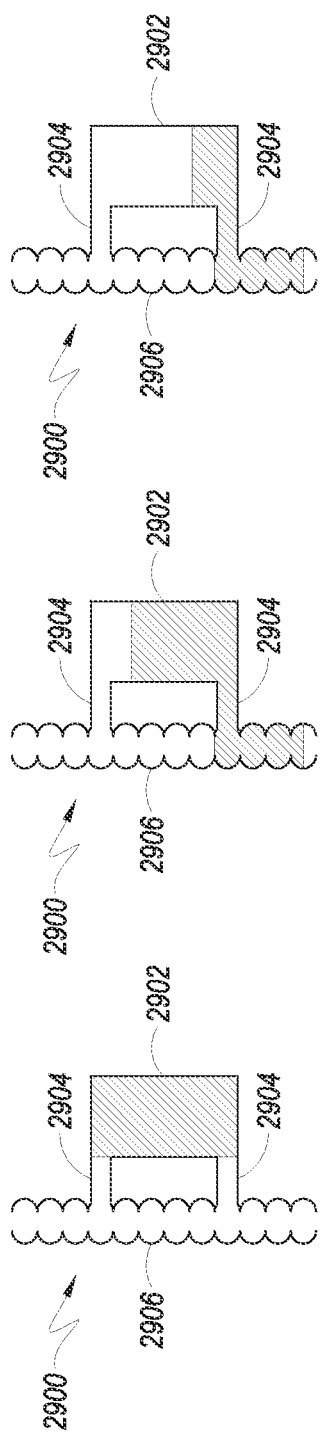
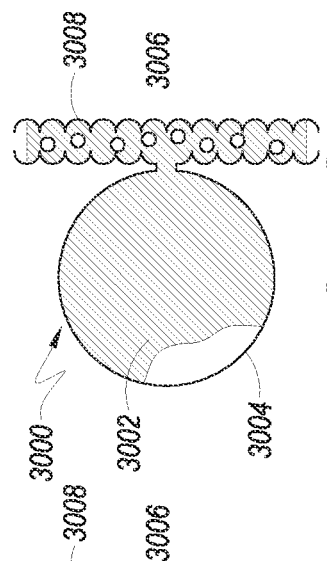
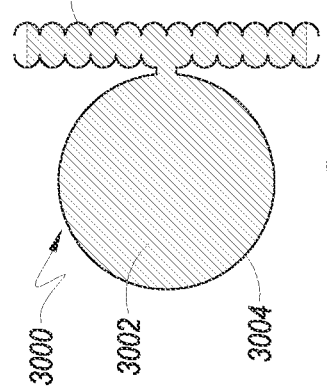
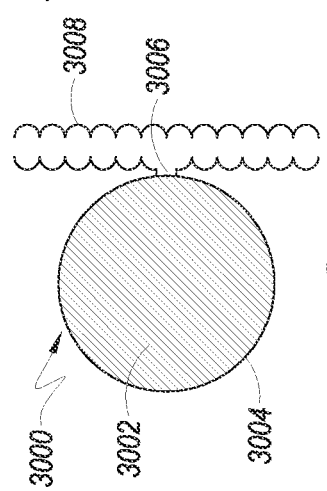

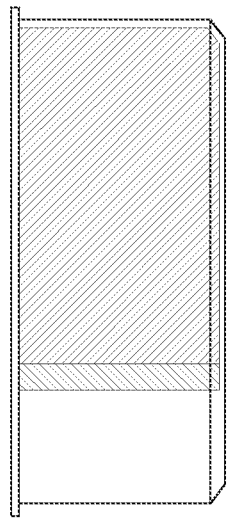
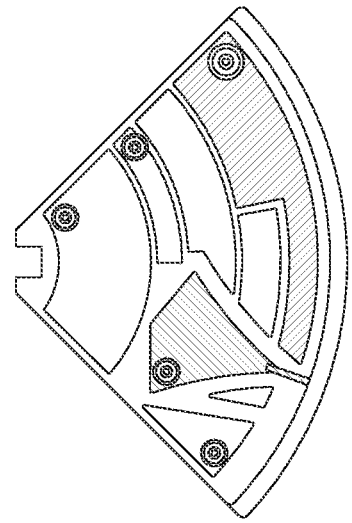
FIG. 41B
(40 - 125 mL)
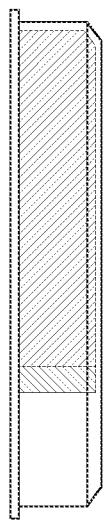
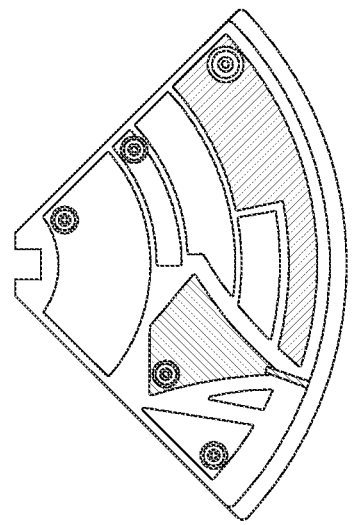
FIG. 41A
(1 - 10 mL)

CENTRIFUGAL FLUID SEPARATION DEVICE

CROSS-REFERENCE TO RELATED APPLICATIONS

This application is a continuation application of U.S. application Ser. No. 15/719,224 filed Sep. 28, 2017 and claims priority to U.S. Provisional Patent Application No. 62/403,312 filed Oct. 3, 2016, entitled CENTRIFUGAL FLUID SEPARATION DEVICE; U.S. Provisional Patent Application No. 62/416,519 filed Nov. 2, 2016, entitled CENTRIFUGAL FLUID SEPARATION DEVICE; and U.S. Provisional Patent Application No. 62/500,021, filed May 2, 2017, entitled CENTRIFUGAL FLUID SEPARATION DEVICE, each of which are incorporated by reference herein in their entirety.

BACKGROUND

The present application describes a centrifugal fluid separation device including one or more modular fluid separation cassettes disposed radially about a rotor assembly of a centrifuge and related system and method.

In many different fields, fluids carrying particle substances must be filtered or processed to obtain either a purified liquid or a purified particle end product. As a result, a number of fluid separation devices and related techniques have been developed and are currently employed across a broad spectrum of applications.

In the medical field, it is often necessary to filter or separate blood. Whole blood consists of both liquid components and particle components. The liquid portion of blood is largely made up of plasma. The particle components of blood, which may be referred to as "formed elements," include red blood cells (erythrocytes), white blood cells (including leukocytes) and platelets (thrombocytes). Although individual particle constituents may have similar densities, the groups of formed elements generally follow an average density relationship which, in order of decreasing density, is as follows: red blood cells, white blood cells and platelets. Plasma is less dense than even the blood platelets. Likewise, the particle constituents of blood can be classified according to relative size. In particular, particle constituents generally decrease in size as follows: white blood cells, red blood cells and platelets. These size and density relationships are important insofar as most current separation devices and techniques rely upon them, or upon differences in particle surface chemistry characteristics, in order to effectively and reliably separate and/or filter the blood components.

Of particular interest in whole blood separation is the ability to obtain purified Peripheral Blood Mononuclear Cells (PBMCs). PBMCs are peripheral blood cells characterized by a round nucleus, and which form an essential component of the human immune system. PBMCs are utilized in research and clinical applications across an array of fields including immunology, infectious diseases, hematology, vaccine development, tissue transplant, high-throughput screening, and so on. PBMCs include monocytes, lymphocytes and macrophages. Lymphocytes consist of T cells, B cells and Natural Killer (NK) cells, each playing a crucial role in the body's natural defenses. In order to study and analyze PMBCs, clinicians and researchers first require an effective separation of PBMCs from whole blood. The efficacy of this isolation is critical in obtaining reliable and accurate results in every subsequent phase of study and analysis.

Most commonly, blood components are separated or harvested from other blood components using a centrifuge. The centrifuge rotates a blood reservoir to separate components within the reservoir using centrifugal force. In use, blood enters the reservoir while it is rotating at high speed which generates centrifugal force. The centrifugal force stratifies the blood components and, consequently, particular components may be separately removed. Centrifuges are effective at, e.g., separating platelets from whole blood; however, centrifuges generally cannot effectively separate all of the white blood cells from the platelets. Historically, blood separation and centrifugation devices have been unable to consistently produce an end product having a purity which is high enough to satisfy current standards.

Because typical centrifuge collection processes are unable to consistently and satisfactorily separate blood into its constituent components, further processes have been added to improve results. For instance, in one such procedure, after centrifuging, platelets are passed through a porous woven or non-woven media filter, which may have a modified surface, in order to remove white blood cells. However, use of the porous filter introduces a variety of problems. Conventional porous filters may be inefficient because they may permanently remove or trap an unacceptably high amount (e.g., 5-20%) of the desired component. Conventional filters may also reduce product quality (e.g., "platelet viability"). For example, once passed through a filter, a percentage of the components may cease to function properly and may be partially or fully activated. In addition, porous filters may cause the release of brandykinin, which may lead to hypotensive episodes in a patient. Porous filters are also expensive and often additional time consuming manual labor is required to perform a filtration process. Additionally, after centrifugation and before porous filtering, a period of time must pass to give activated platelets time to transform to a deactivated state. Otherwise, the activated platelets are likely to clog the filter. For at least these reasons, porous filtration may not be a suitable filtration procedure.

Another conventional process is centrifugal elutriation. In centrifugal elutriation, cells are suspended in a liquid medium without the use of a membrane filter. In one common form of elutriation, a cell batch is introduced into a flow of liquid elutriation buffer. This liquid, which carries the cell batch in suspension, is then introduced into a funnel-shaped chamber located in a spinning centrifuge. As additional liquid buffer solution flows through the chamber, the liquid sweeps smaller sized, slower-sedimenting cells toward an elutriation boundary within the chamber, while larger, faster-sedimenting cells migrate to an area of the chamber having the greatest centrifugal force.

When the centrifugal force and the force generated by the fluid flow are balanced, the fluid flow is increased to force slower-sedimenting cells from an exit port in the chamber, while faster-sedimenting cells are retained in the chamber. If fluid flow through the chamber is increased, progressively larger and faster-sedimenting cells may be removed from the chamber.

Thus, centrifugal elutriation separates particles having different sedimentation velocities. Stoke's law describes sedimentation velocity (SV) of a spherical particle as follows: $SV = r2 \, (\rho_p - \rho_m) g \eta$, where, r is the radius of the particle, $\rho_p$ is the density of the particle, $\rho_m$ is the density of the liquid medium, $\eta$ is the viscosity of the medium, and g is the gravitational or centrifugal acceleration. Because the radius of a particle is raised to the second power in Stoke's equation, whereas the density of the particle is not raised to the second power, it is the size of a cell rather than its density which more greatly influences its sedimentation rate. This explains why, among particles having similar densities, larger particles generally remain in a chamber during centrifugal elutriation while smaller particles are released.

Further, and more generally, it should be noted that centrifugal force increases with an increase distance from the axis of rotation of the centrifuge according to the following equation: $F_c=mv^2/r$, where $F_c$=centrifugal force, m=mass, v=velocity at radius r, and r=radius or perpendicular distance from the axis of rotation to the center of mass of the revolving body. Notably, as velocity increases with distance from the axis of rotation, the velocity increases exponentially, whereas the divisor (radius) does not increase exponentially. Thus, increases in radius result in higher centrifugal forces. In centrifugation parlance, centrifugal force may also be expressed relative to the earth's gravitational force, i.e., as Relative Centrifugal Force (RCF) or the "G-force." The equation for this conversion is as follows: RCF or G-Force=$1.12 \times R \times (RPM/1000)^2$. Throughout this application, G-force may be used interchangeably with RCF, and "G-field" may be used to indicate the centrifugal field.

Centrifugal elutriation has a number of limitations, some of which are noted in described in U.S. Pat. No. 3,825,175 to Sartory. For example, in most centrifugal elutriation processes, particles must be introduced within a flow of fluid medium in separate discontinuous batches to allow for sufficient particle separation. Thus, some elutriation processes only permit separation in particle batches and require an additional fluid medium to transport particles. In addition, flow forces must be precisely balanced against centrifugal force to allow for proper particle segregation.

In another limitation of centrifugal elutriation, a Coriolis jetting effect takes place when particles flow into an elutriation chamber from a high centrifugal field toward a lower centrifugal field. The fluid and particles turbulently collide with an inner wall of the chamber facing the rotational direction of the centrifuge. This phenomenon mixes particles within the chamber and reduces the effectiveness of the separation process. Moreover, Coriolis jetting shunts flow along the inner wall from the inlet directly to the outlet. Thus, particles pass around the elutriative field to contaminate the end product.

Particle mixing by particle density inversion is yet another limitation encountered in some prior elutriation processes. Here, fluid flowing within the elutriation chamber has a decreasing velocity as it flows in the centripetal direction from an entrance port toward an increased cross sectional portion of the chamber. Because particles tend to concentrate within a flowing liquid in areas of lower flow velocity, rather than in areas of high flow velocity, the particles concentrate near the increased cross-sectional area of the chamber. Correspondingly, since flow velocity is greatest adjacent the entrance port, the particle concentration is reduced in this area. Density inversion of particles takes place when the centrifugal force urges the particles from the high particle concentration at the portion of increased cross-section toward the entrance port. This particle turnover reduces the effectiveness of particle separation by elutriation.

Referring specifically to PBMC separation, the current procedure for obtaining PBMCs is a density gradient centrifugation. In this procedure, a density gradient media renders lymphocytes and monocytes under a plasma layer during centrifugation. Typical workflows for obtaining PBMCs via a density gradient centrifugation are well known in the art. Centrifugal density gradient PBMC separations also suffer from various of the limitations described above, making it difficult to obtain a suitable white cell fraction from a small sample of whole blood. The current procedures for separating PMBC are labor and time intensive, and require highly qualified personnel with considerable technical expertise. It is thus desirable to reduce the time and labor required by the operator to complete an entire collection procedure, as well as to reduce the complexity of the present procedure in order to increase productivity, to reduce the need for highly skilled labor and to lower the potential for operator error.

For these and other reasons, there is a need to improve current blood separation systems and practices. More particularly, there is a need for further devices and techniques which are scalable, which improve the consistency of PMBC collection, which are more effective in separating PMBCs from small samples of blood, which yield a product having a higher purity, and which reduce each of the time, the labor and the costs associated with the current state of the art.

Embodiments of the present application have been made in light of these and other considerations. However, the relatively specific problems discussed above do not limit the applicability of the embodiments of the present application.

SUMMARY

The summary is provided to introduce aspects of some embodiments of the present application in a simplified form, and is not intended to comprise and exhaustive list of all critical or essential elements of the claimed invention, nor is it intended to limit the scope of the claims.

According to one aspect of the present application, a modular cassette for separating a composite fluid into at least two component parts thereof during centrifugation is provided. The modular cassette includes a fluid inlet portion, at least one fluid separation portion, at least one media chamber in fluid communication with the fluid separation portion, a fluid collection portion, at least one fluidic channel configured to form a fluid communication between at least two components of the cassette, at least one wax valve including undulating flow channel portions configured to close at least one of the fluidic channels and at least one heating element configured to actuate the at least one wax valve.

According to another aspect of the present application, a modular cassette for separating a composite fluid into at least two component parts thereof during centrifugation provided for herein includes a fluid inlet portion, at least one fluid separation portion including a middle section, the middle section including fluid separation means, at least one media chamber in fluid communication with the fluid separation portion, a fluid collection portion, at least one fluidic channel configured to form a fluid communication between at least two components of the cassette, and at least one valve configured to close at least one of the fluidic channels.

According to yet another aspect of the present application, a modular cassette for separating a composite fluid into at least two component parts thereof during centrifugation provided for herein includes a fluid inlet portion, at least one fluid separation portion, at least one media chamber in fluid communication with the fluid separation portion, a fluid collection portion, at least one fluidic channel configured to form a fluid communication between at least two components of the cassette at least one wax valve configured to close at least one of the fluidic channels, and at least one resistor of a resistor array configured to actuate at least one wax valve.

According to another aspect of the present application, a method for separating a composite liquid into at least two component parts thereof is provided. The method includes inputting the composite liquid into a first portion of a modular cassette, inputting, at a distance from an axis of rotation that is smaller than a distance from the axis of rotation of the first portion, a separation media having a greater density than the composite fluid into a second portion of the modular cassette, inputting the modular cassette into the centrifuge, rotating the cassette in the centrifuge, actuating, with an electrical resistor, a wax valve to release the separation media from the second portion into the first portion, causing a displacement of the composite fluid in the first portion, separating, in the first portion, the composite fluid into two or more of its component parts, and collecting, from the cassette, one or more of the separated component parts of the composite liquid.

Further embodiments of the present application include various devices, systems and methods for separating a composite liquid. The composite liquid may be any liquid, including whole blood, and may comprise a cellular component, such as a Peripheral Blood Mononuclear Cell (PBMC) component thereof.

BRIEF DESCRIPTION OF THE DRAWINGS

Non-limiting and non-exhaustive embodiments are described with reference to the following figures.

FIGS. 28A to 28C illustrate a NOV configured to utilize a crystalline heat activated material according to an embodiment of the present application;

FIGS. 29A to 29C illustrate a NOV configured to utilize an amorphous heat activated material according to an embodiment of the present application;

FIGS. 30A to 30C illustrate yet another NOV according to an embodiment of the present application;

FIGS. 41A and 41B illustrate a cross sectional comparison of two modular fluid separation cassettes according to an embodiment of the present application;

DETAILED DESCRIPTION

The principles described the present application may be further understood by reference to the following detailed description and the embodiments depicted in the accompanying drawings. It should be understood that, although specific features are shown and described below with respect to detailed embodiments, the present application is not limited to the embodiments described below.

Embodiments below may be described with respect to separating whole blood and blood components; however, such descriptions are merely illustrative, and those of skill in the art will appreciate that the embodiments are not limited to the descriptions herein. The embodiments are intended for use in products, processes, devices, and systems for separating any composite liquid. Accordingly, the present application is not limited to separation of whole blood or blood components.

Figure 1:
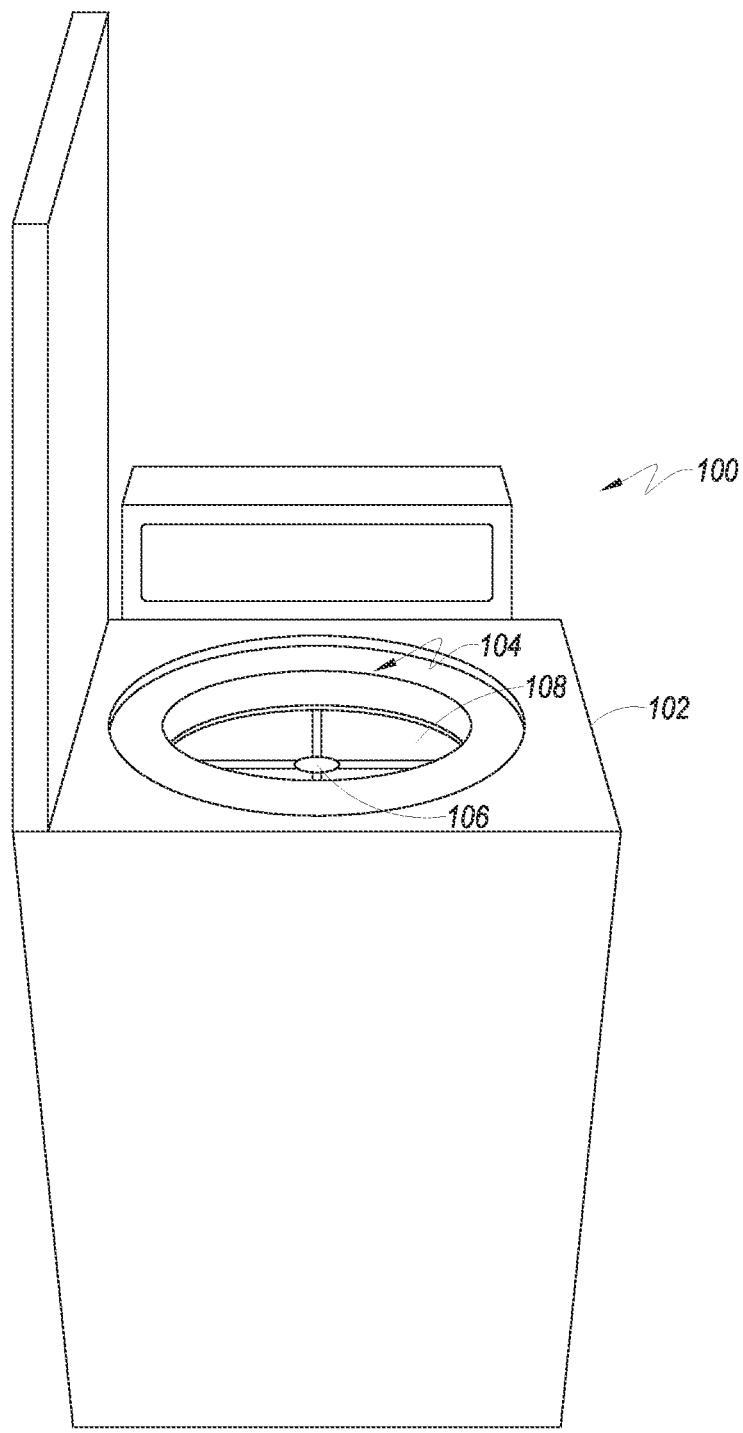
FIG. 1 illustrates a fluid separation system according to an embodiment of the present application.

FIG. 1 illustrates a fluid separation system according to an embodiment of the present application.

Referring to FIG. 1, a fluid separation system 100 includes a floor standing-type centrifuge 102; a rotor assembly 104 configured to be rotated by a motor about an axis of rotation 106; and at least one modular fluid separation cassette 108 affixed to the rotor assembly 104. The components of fluid separation system 100 together define a sterile and disposable fluid separation system.

As shown in FIG. 1, the centrifuge 102 is a floor standing-type centrifuge. Examples of suitable floor-standing-type centrifuges include those used in the SPECTRA OPTIA® apheresis system, the COBE® spectra apheresis system, and the TRIMA ACCEL® automated blood collection system, all manufactured by Terumo BCT, Inc. of Lakewood, Colorado. The centrifuge 102 may be capable of housing one or more modular fluid separation cassettes 108 of varying volumes, and may be suitable for fluid separation of a higher volume than a benchtop-type or other small-scale centrifuge. For example, the floor-standing centrifuge 102 may be capable of housing one or more modular fluid separation cassettes 108 which may each be configured to separate from 0.05 ml to 300 ml of whole blood. More particularly, embodiments may be capable of separating between 0.05 ml and 2 ml, between 1 ml and 10 ml and between 40 ml and 100 ml of whole blood.

Figure 2:
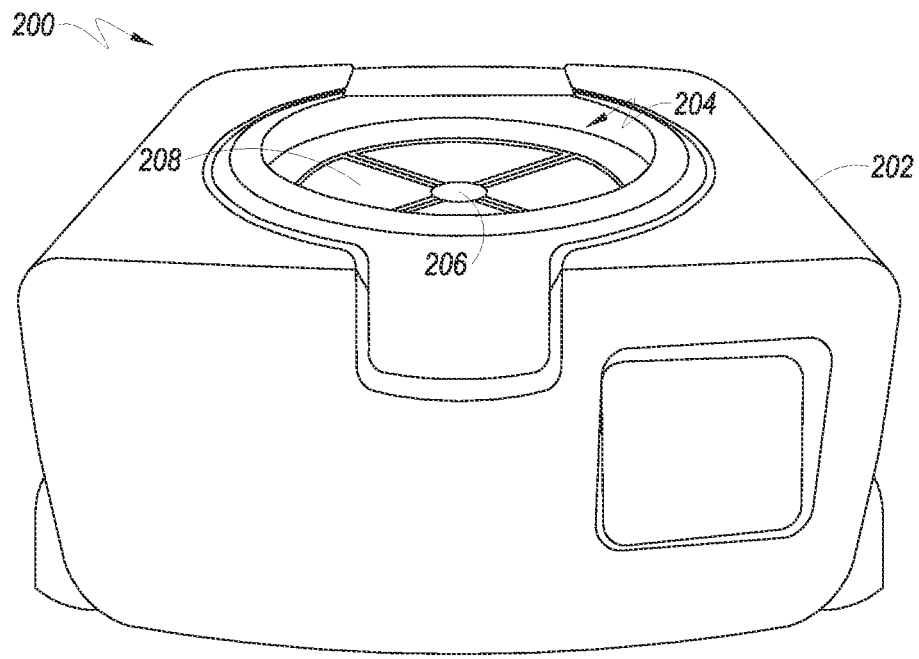
FIG. 2 illustrates a fluid separation system according to another embodiment of the present application.

FIG. 2 illustrates a fluid separation system according to another embodiment of the present application.

Referring to FIG. 2, the fluid separation system 200 includes a benchtop-type centrifuge 202; a rotor assembly 204 configured to be rotated by a motor about an axis of rotation 206; and at least one modular fluid separation cassette 208 affixed to the rotor assembly 204. The components of fluid separation system 200 together define a sterile and disposable fluid separation system.

As shown in FIG. 2, the centrifuge 202 is a bench top-type centrifuge. Examples of suitable bench top-type centrifuges are common and can be found throughout the art. One particular example of a suitable benchtop-type centrifuge is the small benchtop centrifuge by ThermoFischer Scientific, Inc.

In embodiments, the bench top-type centrifuge 202 may be capable of housing cassettes 208 of varying volumes, and may be suitable for the separation of samples having a lower volume than the volume of samples suitable in a floor standing-type centrifuge 102 or other centrifuge. For example, the benchtop-type centrifuge 202 may be capable of housing one or more cassettes 208 which may each be configured to separate between 0.05 ml and 125 ml of whole blood. More particularly, embodiments may capable of separating between 0.05 ml and 2 ml, between 1 ml and 10 ml and between 40 ml and 100 ml of whole blood.

In embodiments, benchtop centrifuges may confer several advantages over larger centrifuge systems. Notably, benchtop systems are suitable for lower volume sampling and cost significantly less than free standing systems. Further, benchtop centrifuge systems may be more easily scaled than other systems. That is, multiple bench-top centrifuges may be linked to one another via a computer network for increased control and customization of sample processing. For these and other reasons, benchtop centrifuge systems find wider application in small-scale laboratory settings.

In use, embodiments of either the floor standing-type or the benchtop-type centrifuge systems may require counter-balancing of the modular fluid separation cassette(s) during centrifugation. One method of counterbalancing involves placing cassettes opposite or equidistant from one another in the circumferential direction of the rotor assembly. Such counterbalancing may be achieved by affixing to the rotor assembly, along with a first modular fluid separation cassette, any of another modular fluid separation cassette, a "dummy" cassette (described below), or any other suitable counterweight, such as another cassette modified to include a traditional fixed-angle or swinging bucket configuration capable of housing one or more microcentrifuge tubes (e.g., 10 ml. Eppendorf tubes), Cryovials, or the like (i.e., a "generalized" or "traditional" cassette). The ability to simultaneously connect different cassette types to the rotor assembly advantageously allows the systems described herein to perform separate workflows concurrently. In particular embodiments, one or more Peripheral Blood Mononuclear Cell (PBMC) separations and post-processing workflows may thus occur concurrently.

In embodiments of either the floor standing-type or benchtop-type centrifuge systems, a cassette housing (not shown) may optionally be included. In use, the cassette housing may aid the rotor assembly in forming a connection with any of the modular fluid separation cassettes, the dummy cassettes and the traditional cassettes. The cassette housing may optionally include means for a mechanical or an electrical connection with the cassettes, and may include further design features which support the efficient centrifugation of fluids. In embodiments, the cassette housing may form an integral part of the rotor assembly. In other embodiments, the cassette housing may be a separate system component that is affixed to the rotor assembly.

The rotor assembly may form a part of the modular fluid separation cassette, or may be a rigid disk with connection means for connecting to, and optionally securing, one or more modular fluid separation cassette, one or more "dummy" cassette (described below), and one or more traditional cassette, or any combination thereof. The rotor assembly may be reusable.

In embodiments, the rotor assembly may include electronic control means and may include electronic communication means. For example, the rotor assembly may include any of one or more processors, embedded code, integrated hardwiring or circuitry, embedded sensors, or any other electronic means which may allow for one-way or for bi-directional communication to and from the rotor assembly, and which may allow for monitoring, assessment and control of the rotor assembly and any cassettes affixed thereto.

In embodiments, the rotor assembly may be electrically and mechanically coupled to the centrifuge system via a spindle or central shaft defining its axis of rotation. For instance, embodiments may incorporate a Pogo® pin, by Everett Charles Technologies, or similar connection for electrical coupling to the spindle or the central shaft of the centrifuge. Alternatively, an edge connection may be made with any of the spindle, with an outer edge of the rotor assembly, or with any cassette affixed thereto. A variety of other conventional means may likewise be incorporated into the rotor assembly in order to provide electrical and mechanical coupling between the rotor and the cassettes.

FIG. 3 to FIG. 6 illustrate examples of a modular fluid separation cassette according to embodiments of the present application.

The descriptions provided below in connection with the embodiments of FIG. 3 to FIG. 6 are merely illustrative. Various features of embodiments shown in FIGS. 3 to 6 are not exclusive to one another, and may be incorporated into one another, or into a single cassette, optionally along with other features. Additionally, the design of the chambers, channels and other cassette components may be adapted to any fluid, and are in no way limited to the separation of whole blood.

Figure 3:
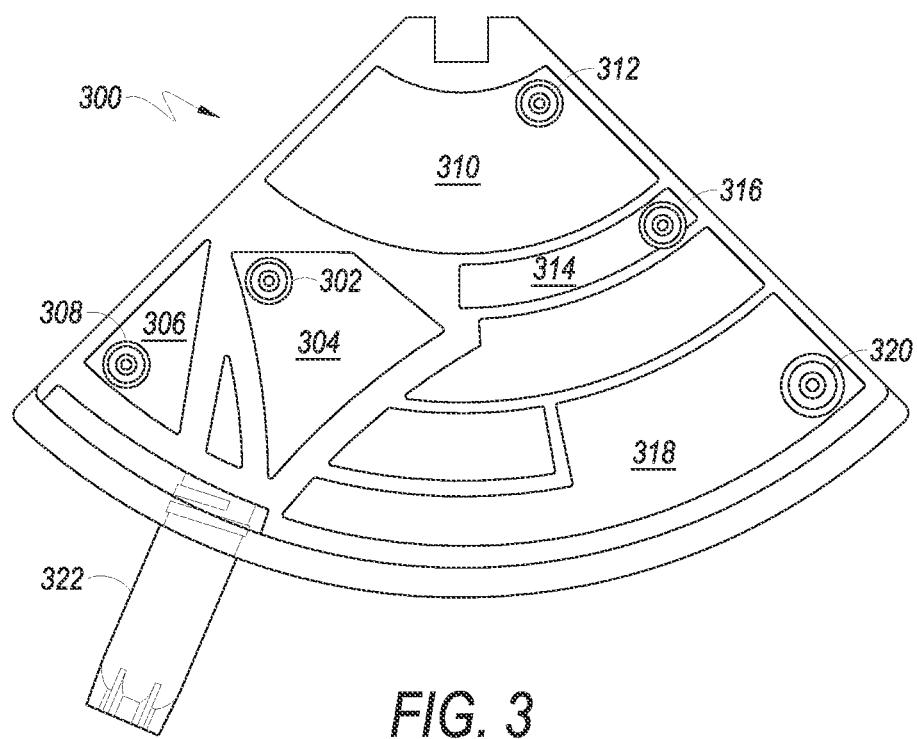
FIG. 3 illustrates an aseptic, open system-type modular fluid separation cassette according to an embodiment of the present application.

FIG. 3 illustrates an aseptic, open system-type modular fluid separation cassette according to an embodiment of the present application.

As shown in FIG. 3, cassette 300 includes an aseptic inlet port 302; a separation chamber 304; a suspension media chamber 306; a suspension media chamber port 308; a buffer solution chamber 310; a buffer solution chamber port 312; a density gradient medium chamber 314; a density gradient medium chamber port 316; a fluid collection chamber 318; an aseptic fluid collection chamber port 320; one or more removable collection vessels 322; one or more fluid channels (not shown); and one or more valves (not shown).

Referring to FIG. 3, modular fluid separation cassette 300 may be referred to as an open-type modular fluid separation cassette because a final product (e.g., PBMC or other fluid component) may be collected in a removable collection vessel 322, or may be collected using traditional means via aseptic collection chamber port 320.

More particularly, in the open-type modular fluid separation cassette 300, whole blood may be introduced or "onboarded" into the modular fluid separation cassette 300 through the aseptic inlet port 302 via conventional aseptic processes, such as with a pipette transfer or any other conventional transfer technique. Likewise, media may be conventionally onboarded through suspension media chamber port 308 and density gradient media chamber port 316, and a buffer may be introduced through buffer solution chamber port 312. In embodiments, particular fluids such as media and buffer solution may alternatively be pre-loaded into the cassette at the time of manufacture. Fluid collection or "offboarding" from the modular fluid separation cassette 300 may occur through the aseptic collection chamber port 320 or through the collection vessel 322. That is, a conventional aseptic transfer technique such as a pipette transfer may be used to collect the fluid from the collection chamber port 320 for collection. Likewise, a removable microcentrifuge tube (e.g., a 10 ml Eppendorf tube), a Cryovial, or any other suitable collection vessel, may optionally be used as a collection vessel 322. In such embodiments, a collection vessel port (not shown) may be included in the cassette to house the collection vessel 322.

The design and placement of the collection vessel 322 and the collection vessel port are not limited in any way. For example, the collection vessel port may be positioned on an outer side of the cassette that is most distal to an axis of rotation, and may be configured to allow insertion or attachment of the collection vessel 322 in any manner (e.g., lengthwise or sideways). Alternatively, the collection vessel port may be positioned on a top or bottom side of the cassette in the direction parallel to the axis of rotation, and may likewise be configured to allow insertion of or attachment the collection vessel 322 in any manner (e.g., lengthwise or sideways). Any conventional means may be implemented to allow for the attachment between the collection vessel 322 and the collection vessel port. In some embodiments, there is no collection vessel and no collection vessel port.

In the foregoing embodiments, purified fluid components may be collected in-situ, which may confer an advantage over embodiments requiring a final product to be held in the cassette until final processing.

Figure 4B:
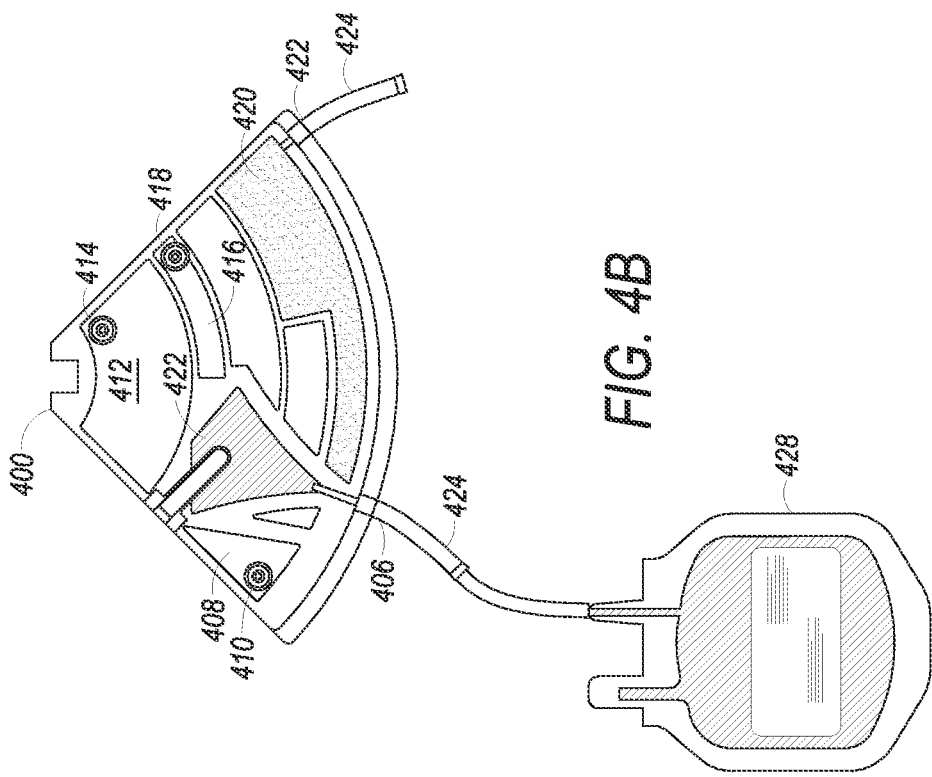
FIGS. 4A and 4B illustrate an aseptic, closed system-type modular fluid separation cassette according to an embodiment of the present application.
Figure 4A:
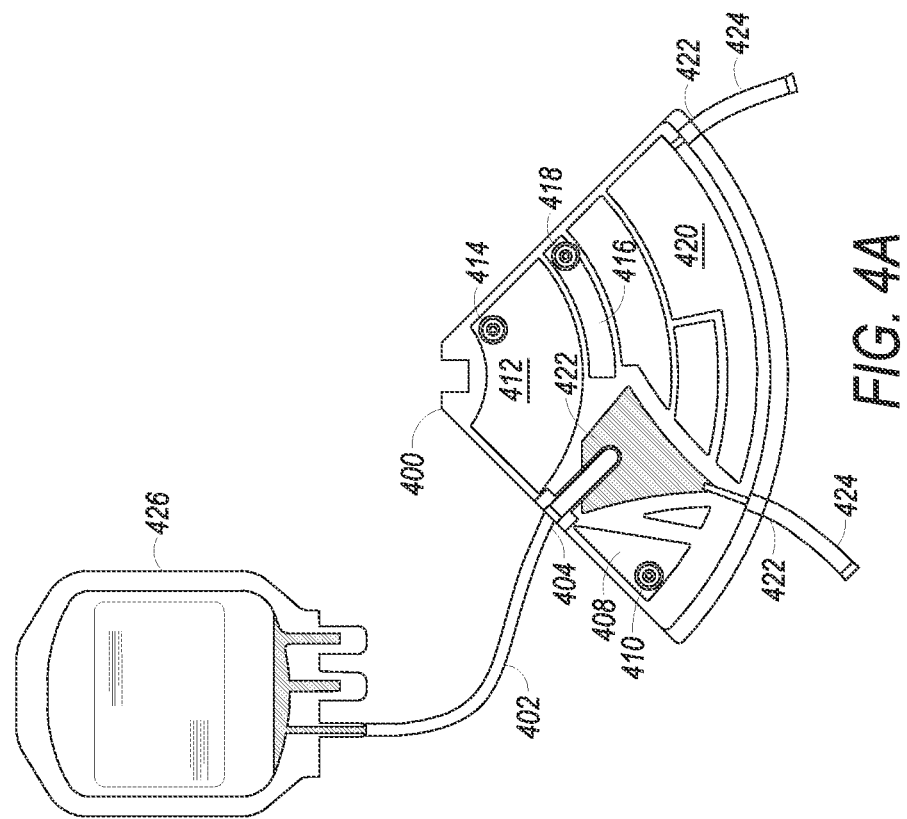

FIGS. 4A and 4B illustrate an aseptic, closed system-type modular fluid separation cassette according to an embodiment of the present application.

Referring to FIGS. 4A and 4B, the modular fluid separation cassette 400 includes an inlet tube 402, an inlet tube stub 404; a separation chamber 406; a suspension media chamber 408; a suspension media chamber port 410; a buffer solution chamber 412; a buffer solution chamber port 414; a density gradient medium chamber 416; a density gradient medium chamber port 418; a fluid collection chamber 420; one or more collection tube stubs 422; one or more collection tubes 424; one or more fluid channels (not shown); and one or more valves (not shown).

In the closed system-type cassettes, each of fluid introduction to the cassette 400 and fluid collection from the cassette 400 are performed through a type of sterile connection which provides additional assurance that the subject fluid remains free from contamination caused by any of harmful bacteria, viruses, or other microorganisms. In embodiments, the inlet tube 402 and collection tubes 424 may comprise sterile PVC tubing or any suitable alternative. In embodiments, a user may utilize a sterile docking device (not shown) to connect the inlet tube 402 to a blood bag 426 for fluid onboarding, or to connect the collection tube 424 to a collection bag 428 for fluid offboarding, thereby enabling a fluid transfer having additional safeguards against contamination risk.

Figure 5:
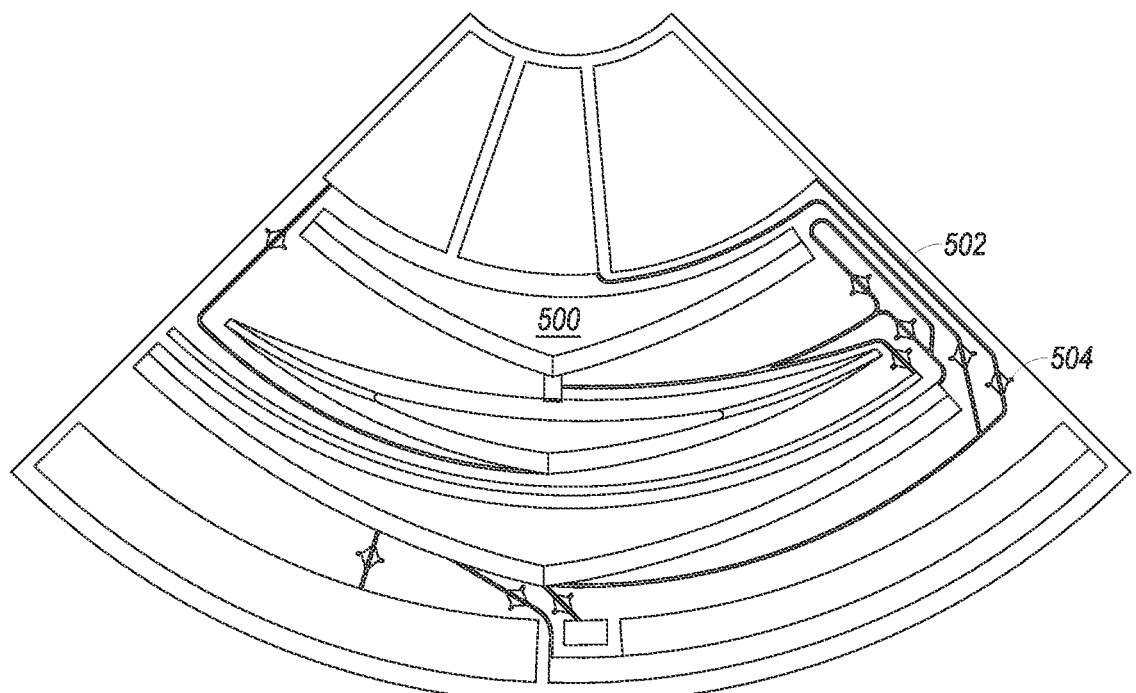
FIG. 5 illustrates a fluid separation cassette according to an embodiment of the present application.
Figure 6:
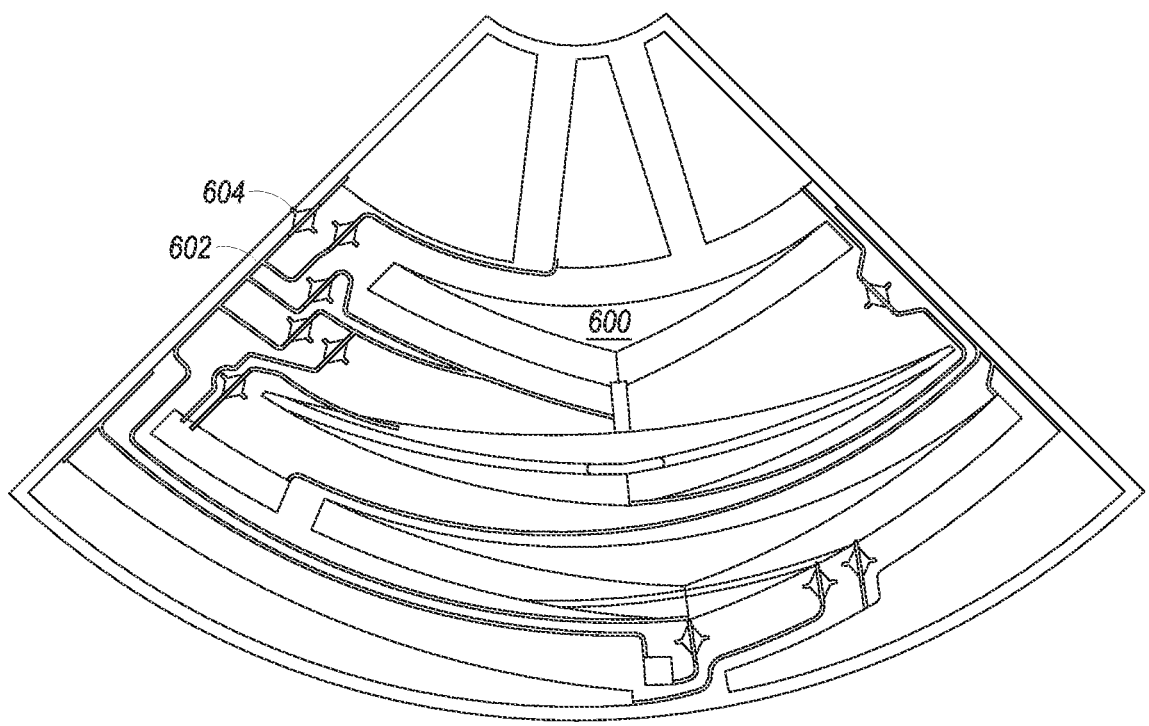
FIG. 6 illustrates another fluid separation cassette according to an embodiment of the present application.

FIG. 5 and FIG. 6 illustrate fluid separation cassettes according to embodiments of the present application.

As shown in the separation cassettes of FIG. 5 and FIG. 6, a given chamber 500, 600 may incorporate a conical aspect, and may include a middle portion or other portion which is narrower than a top portion or a bottom portion thereof. FIG. 5 and FIG. 6 also illustrate various flow channels 502, 602 and valves 504, 604 which connect various components of the modular fluid separation cassette.

As shown, the modular fluid separation cassettes shown in FIG. 3 to FIG. 6 are portable. That is, once a separated fluid component is obtained in the collection chamber of the modular fluid separation cassette at one physical location, the modular fluid separation cassette may then be portably moved, including the separated final product therein, to another location for removal or processing of the desired component. In embodiments, the collection chamber for the desired separated fluid may further include a collection media or a cell preservation media which may assist in maintaining the integrity of the collected fluid component, such as a PMBC blood component, during storage and transportation. Such embodiments represent a significant advantage over the current state of the art insofar as, upon collection, the purified fluid component is already suspended in media which aids in maximizing sample integrity and eliminating manual post-processing steps, such as manual collection and subsequent freezing. Moreover, the samples produced are more convenient and inexpensive to transport.

The use of modular fluid separation cassettes described herein may confer several advantages over traditional fluid separation processes. For instance, conventional centrifugation systems and processes may require the use of additional equipment, such as a Class II Biological Safety Cabinet or other bench and ventilation system in order to maintain a safe environment. In contrast, the aseptic, self-contained aspect of certain embodiments of the modular fluid separation cassettes described herein may eliminate the underlying risk of exposure mitigated by such equipment. This results in a reduction in cost and a reduced potential for exposure and operator error.

Another advantage is that the modular fluid separation cassettes of the present disclosure are particularly capable of yielding a product which is a viable cellular component of blood. In the related art, known centrifugal processes using a disk or similar design may effectively separate a particular fluid into its constituent parts; however, such processes cannot be analogized to the collection of a viable cellular component of whole blood. That is, cellular components of whole blood may be particularly delicate or fragile, and consequently, there exists a relative difficulty in maintaining cellular integrity during centrifugation processes in which cells must travel through a variety of irregularly shaped channels and chambers in a high speed, high G-field environment that exposes the cells to a variety of degradative mechanical processes.

Fluid flows within various embodiments of the modular fluid separation cassettes described herein may be managed using several unique principles. When used together or separately, these principles may greatly simplify the design of both the cassettes and the associated hardware used to manage the cassettes during operation. Proper use of these principles may obviate the need for independent mechanisms to pump, sense levels, and/or sense volumes of the various fluids used during the separation process. Further, these principles may permit "on-rotor" flow management without the need for external fluidic connections such as rotating seals or seal-less rotating loops.

One such fluid flow principle eliminates the need for active pumping of fluids within the cassette during rotational or centrifugal operation. This involves the proper positioning of fluid chambers within the cassette. Fluid chambers are placed at various radial positions such that opening a valve between chambers will facilitate flow from one chamber to another. In general, chambers are arranged so that, when a valve is open, fluid flows down the G-field gradient into a receiving chamber. In this manner, chamber placement, initial fluid placement within chambers, connecting flow channel placements, and valve placements are pre-positioned so that fluids flow outward in the G field or in a "downhill" direction.

Another such fluid flow principle eliminates the need for valves and/or level sensing to terminate flow between chambers. Fluid volumes and chambers volumes may be chosen so that when flow is enabled between two chambers, flow between the chambers will automatically terminate when the proper volume has flowed. Flow ceases when the liquid levels within the two connected chambers reach equilibrium radial positions. The equilibrium radial position of each compartment's surface will inherently accommodate the density of the fluid contained within the compartments. That is, if the density of the fluid in each compartment is identical, the radial positions of the compartment's liquid surfaces will be identical. If one compartment contains a higher density fluid, the radial position of its free surface will be larger than the radial position of the second compartment's surface.

Various embodiments of the modular fluid separation cassettes described herein may also operate based on a principle of volume matching. That is, a volume of introduced fluid may match a volume of end-product (e.g., waste product or other desired end-product) from a particular chamber. For instance, a known volume of more dense fluid (e.g., density gradient media) may be introduced into a media chamber in modular fluid separation cassette. The density gradient media may then be introduced into a separation chamber in the modular fluid separation cassette which holds a fluid constituent that is less dense than the density gradient media (e.g., whole blood). Under the G-force of centrifugation, the denser density gradient media will displace less dense whole blood constituents as the density gradient media moves in a downhill direction in the G-field (i.e., a direction that is increasingly distant from an axis of rotation). The displaced constituent(s) will resultantly move in an uphill direction in the G-field, and may consequently be collected in a known volume (i.e., the volume of the density gradient media introduced; the volume of the displacement). Using volume matching, it may be possible to obtain a substantial (e.g., 25%) increase in product yield at similar levels of purity. Likewise, it may be possible to obtain a higher purity yield at the same collection volume.

Further unique principles which may be incorporated into embodiments of the present application include the use of a fluid "pulley" and a fluid "push." Using a fluid "pulley," a desired fluid in a second chamber can be moved uphill in a G-field using the regular pressure driven flow of a remote fluid in a first chamber moving "downhill" in the G-field. That is, a regular downhill flow of fluid in first chamber that connected via a channel to a top portion of a second chamber may be used to draw a negative pressure in the second chamber, causing the fluid in the second chamber to be "pulled" uphill in the G-field by the induced pressure gradient. In embodiments, the only connection between the two chambers may be an air-filled channel, which would allow for the movement of fluid without any mixing. Alternatively, using a different configuration, the push principle may be used. By using the fluid "push" principle, fluid in the second chamber can be "pushed" uphill in the G-field by the regular pressure driven flow of the remote fluid moving "downhill" in the G-field of the first, remote chamber. Here, the channel connects the first chamber to the bottom of the second chamber, and the increased pressure in the first chamber pushes the fluid in the second chamber uphill in the G-field using a compression of air in the channel.

In embodiments, the "pulley" and the "push" principles can allow for a complete transfer of a fluid into a chamber, and a subsequent transfer of fluid out of the chamber "uphill" in the G-field, which can aid in obtaining higher purity yields. These principles also allow for a transfer of desired fluid through a larger channel having no valve, thereby minimizing shear stress during the transfer. Because the "pulley" and the "push" principles rely on a relative pressure between chambers to drive flow, these techniques may work effectively at any centrifugal speed.

Exemplary embodiments of the modular fluid separation cassettes described herein may be single use (i.e., disposable) or multiple use. In embodiments, the modular fluid separation cassettes herein may be of a variety of types and sizes. For example, the modular fluid separation cassettes described herein may take the form of a "wedge," or of a segment of a disk shape. In such embodiments, several cassettes together may form a complete disk shape. In other embodiments, a single cassette may take the form of an entire disk. In embodiments, the modular fluid separation cassettes described herein may be disposed about the rotor assembly in a stacked configuration (i.e., a "pancaked" configuration) or in a side-by-side configuration (i.e., circumferentially around the rotor assembly).

Exemplary fluid separation cassettes described herein may further incorporate any of a variety of sensors or detection means. That is, particular fluid characteristics throughout separation may further be sensed by sensors positioned throughout the cassette in order to support automation. An exemplary sensor may illuminate a fluidic channel, a chamber, a tube or any other cassette component which holds or transports fluid, and may detect ratios of reflected or transmitted red and green light from the fluid. For instance, the presence of red blood cells can be detected in certain embodiments using means described in the related art of U.S. Pat. No. 5,734,464.

The modular fluid separation cassettes described herein may be manufactured using known materials and techniques. Examples of materials used in the manufacture of the modular fluid separation cassette production and the resistor array (described below) may include polymers such as Polypropylene, Polystyrene, and the like. Examples of manufacturing techniques used in the production of the modular fluid separation cassettes and the resistor array may (described below) include 3-D printing, injection molding, insert molding, and various other conventional means. The cassettes may also be hydrophobic, or may include a hydrophobic coating or a hydrophobic treatment.

Figure 7:
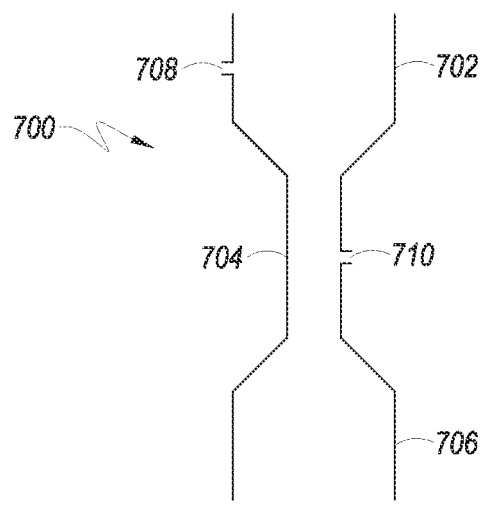
FIG. 7 illustrates an hourglass shaped separation chamber according to an embodiment of the present application.

FIG. 7 illustrates an hourglass shaped separation chamber according to an embodiment of the present application.

Referring to FIG. 7, the separation chamber 700 comprises an upper section 702 which is a section of the chamber most proximal to the axis of rotation; a middle section 704; a lower section 706 which is a section most distal to the axis of rotation; an entry port 708 and an exit port 710.

As shown in FIG. 7, the upper section 702 and the lower section 706 have a cross-sectional area that is greater than the cross-sectional area of the middle section 704. In embodiments, this chamber design may resemble a smooth "hourglass" shape or an angular "hourglass" shape. Inlet port 708 is configured for introducing a fluid (e.g., a suspension of cells) into the separation chamber. Exit port 710 is configured for allowing a removal of a fluid component (e.g., separated PBMCs) from the separation chamber 700. The separation chamber 700 may optionally include an overflow port (not shown) for removing any remaining portions of the suspension from the chamber. Hourglass and similar chamber designs may allow for a more precise separation of fluid components in the middle section 704 where the exit port 710 is positioned. A size relationship between the upper section 702 and the lower section 706 of the hourglass shape to its middle section 704 may, for example, be from two to one (2:1) to ten to one (10:1). In an exemplary embodiment, the cross section of middle section 704 is one quarter (¼) the size of the cross section of the upper and lower sections. The incorporation of a narrow chamber or channel portion for improved separation is not limited herein, and may be incorporated into other channels, chambers and system components.

Figure 8A:
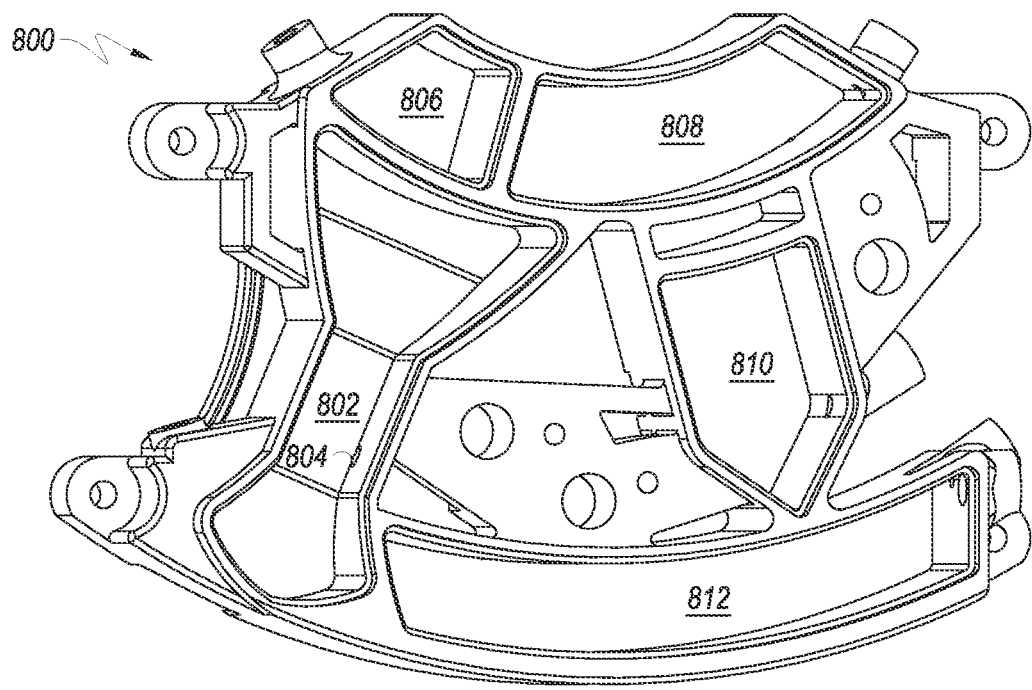
FIGS. 8A and 8B illustrate an hourglass shaped separation chamber within a partial cutout of a modular fluid separation cassette according to an embodiment of the present application.
Figure 8B:
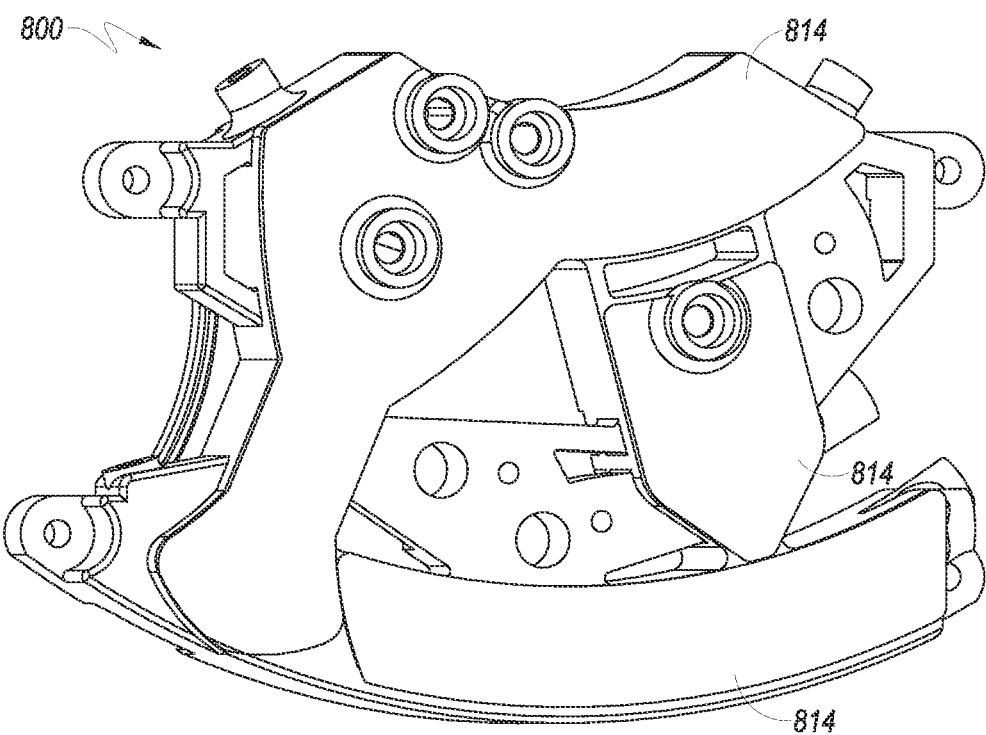

FIGS. 8A and 8B Illustrate another hourglass shaped separation chamber within a partial view of a modular separation cassette according to an embodiment of the present application.

FIG. 8A is a perspective view of a modular fluid separation cassette 800 including an "hourglass" shaped separation chamber 802, a separation chamber exit port 804, a media chamber 806, a buffer solution chamber 808, a wash chamber 810 and a collection chamber 812. In FIG. 8A, the interior of each chamber is exposed insofar as this view does not show chamber lids.

FIG. 8B is a perspective view of the cassette shown in FIG. 8A including optional chamber lids 812 which cover each of the cassette chambers.

In FIG. 8A, the separation chamber exit port 804 is located in the vertical wall of the middle, narrower portion of the separation chamber 802. The exit port 804 may be of a diameter and a geometry which is optimized for collecting a particular fluid or fluid constituent, such as a Mononuclear Cell (MNC) layer. The exit port 804 may face perpendicular to the direction of centrifugal force, may face relatively outward (over 90 degrees) from the center of rotation, or may face relatively inward (less than 90 degrees) toward the center of rotation. For instance, in a preferred embodiment, the exit port may face relatively inward toward the center of rotation whereby an angle between the exit port and a line parallel to the centrifugal force may be from 5 to 60 degrees, such as from 30 to 60 degrees or from 40 to 50 degrees. The exit port shown in of FIGS. 9A, 10A and 11A below illustrate this latter description (i.e., having an angle of approximately 45 degrees).

In further embodiments, a fluid separation cassette may incorporate a fluid separation chamber having means for concentrating a layer of fluid or fluid constituents in proximity to an exit port. Such means for concentrating a layer of fluid or of fluid constituents in close proximity to the exit port may take the form of a planar, multi-planar or similarly functioning surface (i.e., a "skimmer dam") positioned at an angle within the separation chamber. For example, the skimmer dam may be disposed at an angle of between 15 and 70 degrees, such as between 25 and 60 degrees or between 40 and 50 degrees relative to a line parallel to the centrifugal force within the chamber. The distal end of the skimmer dam (i.e., the end furthest from the axis of rotation, or the furthest "downhill" portion) may be positioned in the separation chamber at substantially the same radial distance from the axis of rotation as the position of the exit port. The distance between the distal end of the skimmer dam and the exit port may be optimized to facilitate the efficient movement of a particular fluid or fluid constituent (e.g., MNCs) from the separation chamber through the exit port. The skimmer dam may occupy substantially all of, or less than all of, the entire distance between the walls of the separation chamber. That is, a space may exist between one or both sides of the skimmer dam and the vertical side wall of the separation chamber in order to allow MNCs and platelets to rise and to allow RBCs and granulocytes to sediment.

Figure 9A:
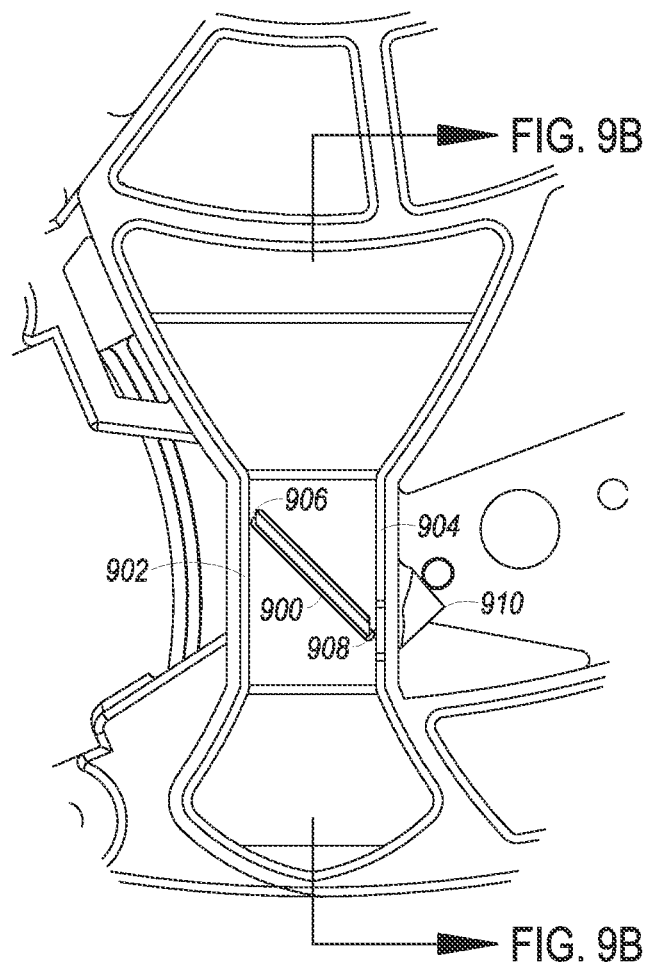
FIGS. 9A and 9B illustrate a planar skimmer dam positioned within a separation chamber according to an embodiment of the present application.
Figure 9B:
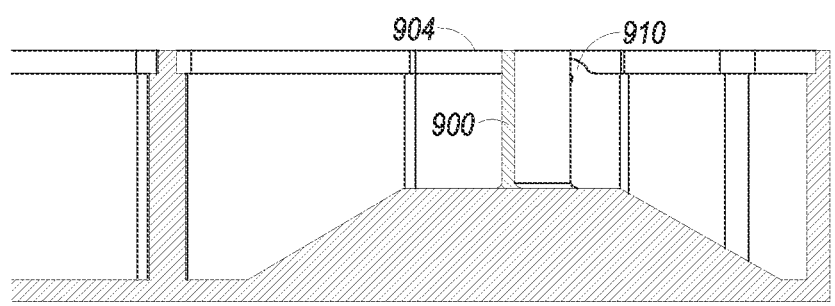

FIGS. 9A and 9B illustrate a planar skimmer dam positioned within a separation chamber according to an embodiment of the present application. The embodiment shown in FIGS. 9A and 9B is configured to not contact at least two (2) vertical side walls of the separation chamber.

FIG. 9A is a top view of the skimmer dam 900 between vertical walls 902, 904 of the narrow portion of the separation chamber. As shown in FIG. 9A, spaces 906, 908 exist between the vertical sidewalls 902, 904 and the skimmer dam 900. Also shown is an exit port 910 located toward the front of the middle portion of the separation chamber at approximately the same radial position from the axis of rotation as the distal end of the skimmer dam. The positioning of the exit port 910 may vary, and may preferably be located as is depicted in the FIGS.

FIG. 9B is a cross sectional view of the planar skimmer dam 900 used to show that the skimmer dam 900 comprises a single plane.

Figure 10A:
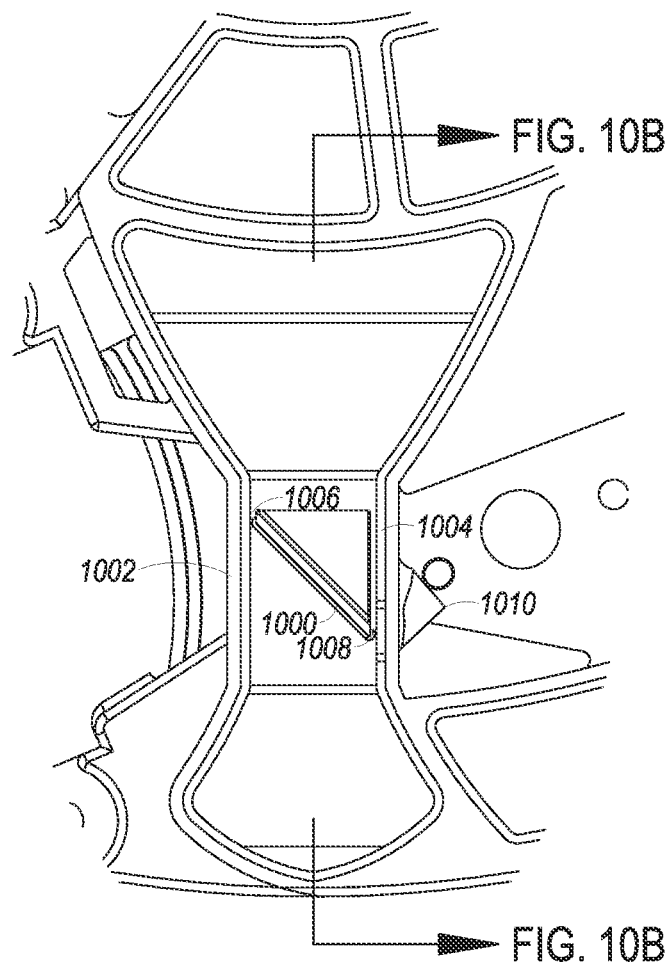
FIGS. 10A and 10B illustrate a multi-planar skimmer dam positioned within a separation chamber according an embodiment of the present application.
Figure 10B:
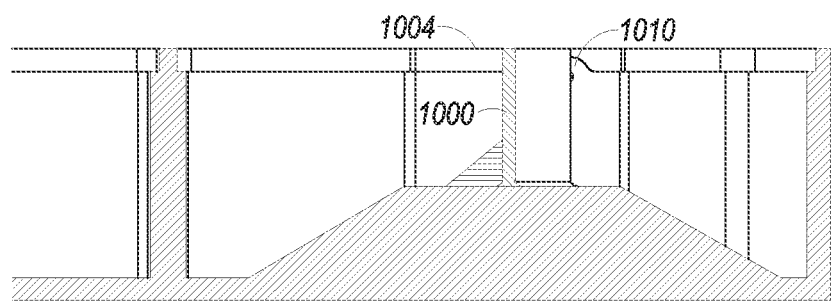

FIGS. 10A and 10B illustrate a multi-planar skimmer dam positioned within a separation chamber according to an embodiment of the present application. The embodiment shown in FIGS. 10A and 10B is also configured to not contact at least two (2) vertical side walls of the separation chamber.

FIG. 10A is a top view showing the multiplanar skimmer dam 1000 in contact with the vertical sidewalls 1002,1004 of the separation chamber, except for gaps 1006 and 1008 designed to allow for the rising of MNCs or platelets and for the sedimentation of RBCs or granulocytes. Also shown is an exit port 1010 as in FIG. 9A.

FIG. 10B is a cross sectional view of the multiplanar skimmer dam 1000. This view used to show that the skimmer dam 1000 comprises two planes.

In certain embodiments, a "double funnel design" may be implemented. That is, a modification may be made such that the skimmer dam and separation chamber resemble and/or function like two funnels oriented opposite one another; one upward facing and one downward facing. In embodiments, this configuration is designed to minimize the number or percentage of a particular fluid constituent (e.g., MNCs) which pass through the gaps between the skimmer dam and the sidewalls of the separation chamber, thereby maximizing a concentration of separated product (e.g., MNCs) near the exit port. In this configuration, the skimmer dam is modified to contact the vertical sidewalls of the separation chamber along a majority of its edge, leaving only a hole (or gap or opening) present in each "funnel" for the rising of MNCs or platelets and for the sedimentation of RBCs or granulocytes. The position of the gaps on either side of the skimmer dam are not limited herein, and may be on the side closest to the flow channels between chambers for easier moldability. The size and geometry of the hole, and in particular, the size of the hole opposite the chamber from the exit port (i.e., the hole furthest uphill, or nearest the axis of rotation), should be large enough to allow for cells to rise at a reasonable rate during initial separation, yet small enough so as to minimize a number of MNCs which pass through during MNC transfer. In certain embodiments of the "double funnel" configuration, a wax valve may be configured to occlude only one hole of the funnel, such as the hole nearest the axis of rotation. Closing the hole nearest the axis of rotation during centrifugation may force MNCs toward the other, "downhill" hole during cell transfer.

Figure 11A:
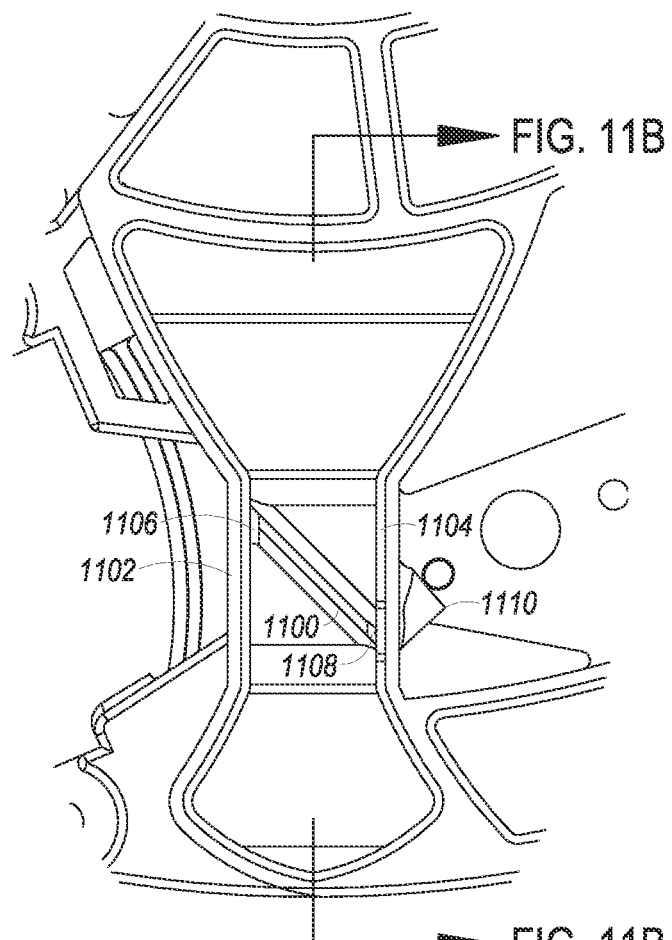
FIGS. 11A and 11B illustrate a multi-planar skimmer dam positioned within a separation chamber and forming a "double funnel" configuration according an embodiment of the present application.
Figure 11B:
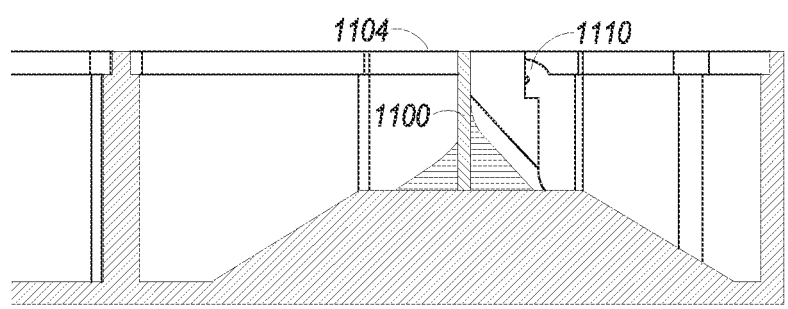

FIGS. 11A and 11B illustrate a multi-planar skimmer dam positioned within a separation chamber and forming a "double funnel" configuration according to embodiments of the present application.

FIG. 11A is a top view showing a skimmer dam 1100 in contact with the vertical sidewalls 1102,1104 of the separation chamber, except for gaps 1106 and 1108 designed to allow for the rising of MNCs or platelets and for the sedimentation of RBCs or granulocytes. Here the gaps 1106,1108 occupy only occur along a section of the intersection between the plane of the skimmer dam 1100 and the sidewall 1102,1104, creating a smaller flow channel. Such embodiments may minimize mixing and ensure proper separation via the use of the small flow channels, or gaps, on the sides of the skimmer dam 1100. Also shown is an exit port 1110.

FIG. 11B is a cross sectional view of the multi-planar skimmer dam 1100 in a double funnel configuration used to show that the skimmer dam 1100 comprises two planes angled to cause fluid to flow through smaller flow channels than the skimmer dam 1000 of FIGS. 10A to 10B.

In further embodiments, wax valves may be positioned at, and configured to occlude, the gaps on either side of the skimmer dam. In an embodiment, such wax valves can be used to form a "multi-use" chamber. For example, in such a multi-use chamber, a Normally Open Valve (NOV), as variously described throughout this application, may be positioned on the outside of each vertical sidewall of the separation chamber proximate to the gap between the skimmer dam and the vertical sidewall. In embodiments, a multi-use chamber may have more than one fluid entry and fluid exit port to allow for various wash, rinse, separation, or other procedure(s). In embodiments, the plurality of ports required for wash, rinse, separation, and the like are positioned "above" (i.e., closer to the center of rotation) the NOV in the G-field, near the distal end of the skimmer dam. That is, the plurality of ports may preferably be positioned at a radial distance from the axis of rotation which is shorter than the distance to the NOV positioned near the distal end of the skimmer dam.

Figure 12A:
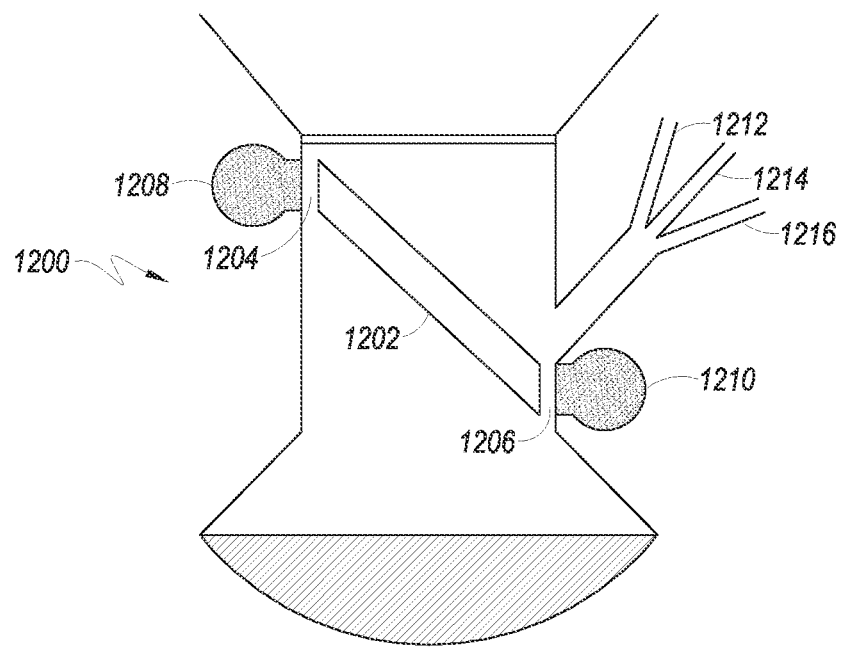
FIGS. 12A and 12B illustrate a multi-use chamber including Normally Open Valves (NOVs) according an embodiment of the present application.
Figure 12B:
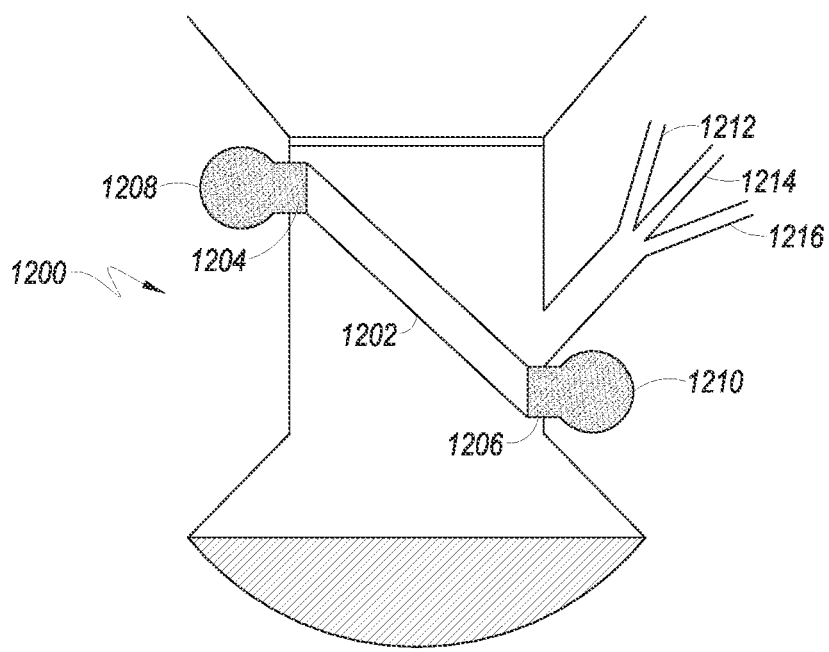

FIGS. 12A and 12B illustrate a multi-use chamber including NOVs according an embodiment of the present application.

FIG. 12A is a top view of a multi-use chamber 1200. A narrow section of multi-use chamber 1200 includes a skimmer dam 1202 which does not touch at least two portions of the chamber sidewall, creating gaps 1204, 1206 at both the distal and proximate end of the skimmer dam 1202 to enable the flow of fluid during various operations. NOVs 1208, 1210 are positioned, respectively, on the outer sidewall of the multi-use chamber 1200 in the same radial position as the gaps 1204, 1206 on either side of the skimmer dam 1202. The NOVs 1208, 1210 are in fluid communication with the chamber 1200 such that, upon actuation, molten material can flow from either NOV 1208, 1210 into the multi-use chamber 1200 and occlude the gaps 1204, 1206 on either side of the skimmer dam 1202. A wash fluid inlet 1212, a wash fluid outlet 1214 a final product/transfer outlet 1216 are variously included to form one or several separate channels depending on process needs.

FIGS. 12A and 12B illustrate the multi-use chamber of FIG. 12A in various stages of a multiple process operation. One exemplary method or workflow for implementing the multi-use chamber of FIGS. 12A and 12B is as follows. First, a separation of whole blood is performed in a separation cycle in the chamber 1200 shown in FIG. 12A. In this cycle, Red Blood Cells fall through the gap 1206 at the distal end of the skimmer dam 1202 while MNCs rise through the gap 1204 nearest the axis of rotation. Next, after the separation of fluid components during the separation cycle, each NOV 1208, 1210 is actuated as shown in FIG. 12B, thereby transforming the separation chamber 1200 into an uncontaminated wash chamber via the occlusion of the gaps 1204, 1206 between the skimmer dam 1202 and the vertical sidewalls of the chamber 1200. Next, full conventional washes can be completed as follows: mixing in wash fluid using was fluid inlet 1212, performing a wash and then draining the waste through wash fluid outlet 1214. Next, after the waste is drained, the final MNC may be collected via transfer outlet 1216. Finally, the MNCs may be suspended before transfer via fluid transfer outlet 1216 or the cells can be washed in one or more wash cycles before transfer. Here, the MNCs may be suspended in a mixture with wash fluid prior to being transferred to another wash chamber. This may cause a minimization of platelet activation due to lack of pressure drop in the cells throughout transfer.

Embodiments herein are not limited. That is, a separation chamber or a multi-use chamber may have an hourglass shape, a substantially hourglass shape, or may be of any other configuration which allows for effective separation of fluid constituents, as depicted throughout the FIGS. For instance, a separation or multi-use chamber may be configured as a two part chamber, whereby the two parts are in fluid connection with one another via fluidic channels. Such channels may optionally include one or more valves, such as those depicted in throughout the FIGS. Likewise, the foregoing configurations are not limited to separation chambers, and may refer to the configuration of any chamber in the cassette. For example, some embodiments may incorporate a conical shape in and aspect of a chamber, such as embodiments which may employ a conical wash chamber that is typical in elutriation, but which is not used in conventional PBMC separations.

In certain embodiments, the skimmer dam may positioned in a separation chamber such that, upon separation, an MNC layer is positioned entirely above the skimmer dam. In this configuration, as the separation chamber is drained, the MNC layer drops (i.e., flows outward in the G-field) and concentrates as it is pushed along the angled surface of the skimmer dam toward the exit port. A small percentage or number of MNCs may pass through the gap between one or both sides of the skimmer dam and a vertical wall of the separation chamber, yet such MNCs may still exit the separation chamber via an exit port once the MNCs reach the radial position of the exit port. In certain embodiments, the top of the skimmer dam, (i.e., the point of the skimmer dam that is highest in the G-field and that is closest to the axis of rotation) may be at or below an entry port.

The various embodiments of separation chambers and skimmer dams described herein may confer a variety of benefits. For example, the concentrating of a MNC layer near an exit port of a separation chamber may result in a higher yield and a decrease in run time. The addition of a means for concentrating a layer of fluid or fluid constituents toward an exit port may also eliminate the need for a narrow portion of a separation chamber, thereby allowing greater design latitude. Such a configuration may be particularly useful as related to a large-volume cassette in which radial height can be shortened for a given chamber volume, thus resulting in a more efficient use of space overall. Additionally, MNC and platelet rising and red blood cell (RBC) sedimentation can occur in separate regions of the separation chamber, which may result in an accelerated separation.

In embodiments, the modular fluid separation cassette includes a port configuration adapted to utilize a Luer taper connection including a fluid line and a vent line. Exemplary ports are shown in FIGS. 3, 4A, 4B and 8B. In embodiments, either a slip taper design or a lock connection design may be used, or a modified version thereof may be used. Examples of such connections are "Luer-Lock" © and "Luer-Slip" ® style connectors by Becton, Dickinson and Company. For example, a modular fluid separation cassette chamber may incorporate a port designed to interface with a female end of an evacuated chamber, such as a BD Vacutainer® Venous Blood Collection Tube, also by Becton, Dickinson and Company. Other Luer® and similar fittings and connections may also be used or modified and incorporated into embodiments as needed.

In further embodiments, one or more ports of the cassette may have a conventional design. For example, a port which is designed as simply an aperture may be utilized in order to allow for traditional pipette fluid introduction and collection. Such ports may be opened and re-sealed using a stop cap or other conventional feature which allows an operator to open and re-seal the port as desired. Any other conventional port design may likewise be incorporated into embodiments in order to effectively onboard and offboard fluid from the modular fluid separation cassette.

The cassette chambers described herein may variously be connected via fluidic channels within which valves may be positioned so that fluid flow can be controlled throughout centrifugation. Channels and valves may be formed within a solid body portion of the fluid separation cassette during manufacturing, or may be formed into, or cut out of (e.g., die cut), another portion of the cassette or layer thereof (e.g., a silicon layer of a resistor layer assembly) and subsequently combined with the remainder of the cassette. Channel size and design are not limited, and various valve designs and materials may be used in different embodiments. In embodiments, channels may have a cross section of 0.3 mm to 2 mm, such as from 0.5 mm to 1 mm. In an exemplary embodiment, the channels may have a cross section of 0.75 mm (0.030×0.030 in.).

In embodiments, novel means may be included for controlling fluid flow rate within the modular fluid separation cassette. That is, in many conventional processes which require highly specific flow rates, such as in elutriation, flow rates are obtained using a pump. Nonetheless, it may be desirable for a variety of reasons to replace the conventional pump with pumpless flow control means. To address this issue, embodiments include a section of a fluidic path or channel which incorporates a multiplicity of fluidic channels of specific dimensions variously combinable to achieve a variety of distinct flow rates. In embodiments, the multiple fluidic channels may be parallel to one another, or may assume another relationship to one another. It is assumed herein that flow rates are based on a variety of variables, such the diameter of the channels, the distance of the channels from the axis of rotation, the RPM of the rotor, the particular viscosity and specific gravity of the fluid, and so on.

Figure 13:
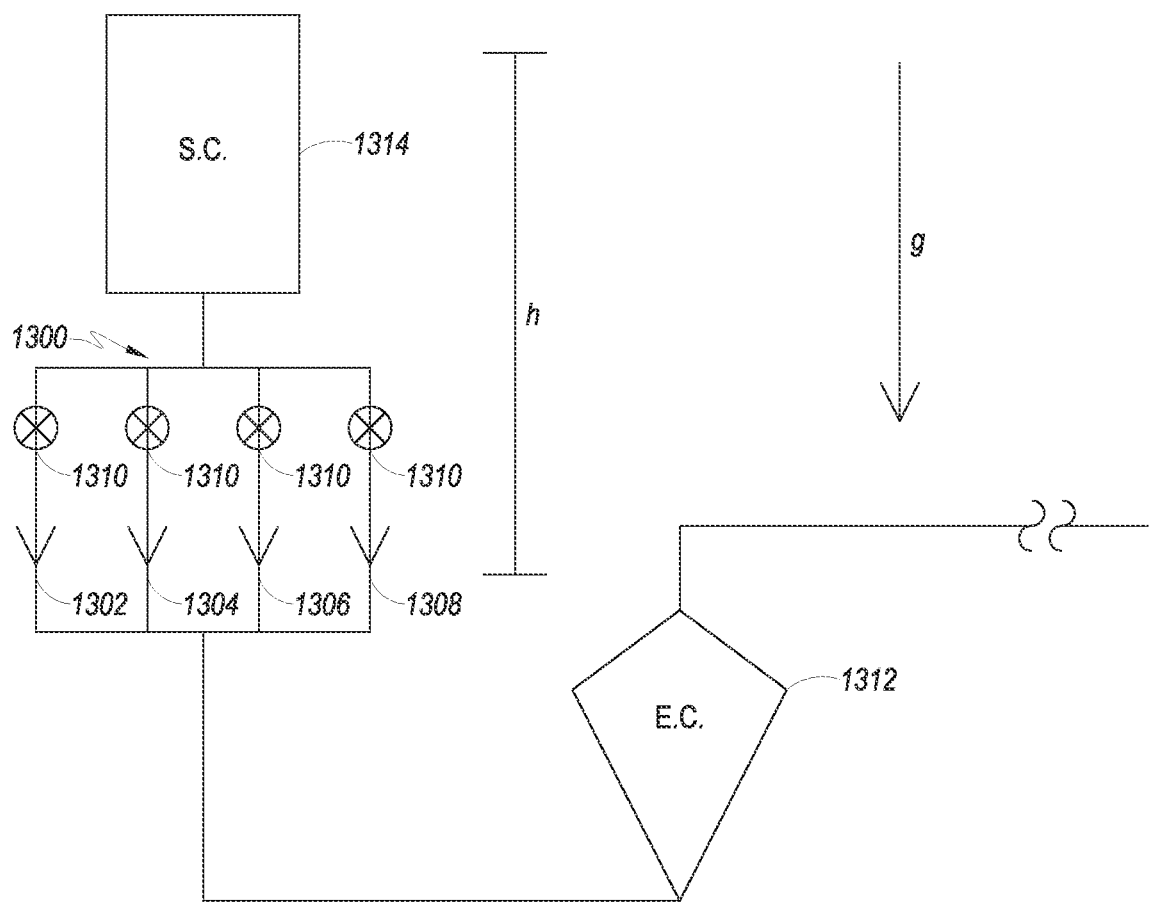
FIG. 13 is a schematic view of parallel fluidic channels for controlling flow rate according to an embodiment of the present application.

FIG. 13 is a schematic view of parallel fluidic channels for controlling flow rate according to an embodiment of the present application.

Referring to FIG. 13, a cluster or a battery of four (4) parallel fluidic channels 1300 having different diameters are shown providing fluid to an elutriation chamber (EC) 1312 from a supply chamber (SC) 1314 that is higher than the EC in a G-field. The channels are positioned proximate to one another along a fluid flow path.

In the embodiment of FIG. 13, channel 1302 allows fluid to flow at 1 ml per minute; channel 1304 allows fluid to flow at 2 ml per minute; channel 1306 allows fluid to flow at 4 ml per minute; and channel 1308 allows fluid to flow at 8 ml per minute. Each of the four (4) parallel fluidic channels includes at least one valve 1310 selected from among the embodiments variously described herein.

Variously actuating the valves in the four (4) parallel fluidic channels 1302, 1304, 1306, 1308 allows for a total flow rate of between 0 ml per minute and 15 ml per minute in distinct 1 ml per minute increments. For instance, when the valve in channel 1302 is open, the valve in channel 1304 valve is closed, the valve in channel 1306 is open, and the valve in channel 1308 is closed, a total flow rate of 5 ml per minute can be achieved. Likewise, when the valve in channel 1302 is closed, the valve in channel 1304 is open, the valve in channel 1306 is closed and the valve in channel 1308 is open, a total flow rate of 10 ml per minute can be achieved. The foregoing flow rates are mere examples, and any desired combination of flow rates could be achieved by utilizing various channel configuration and valve closures.

In embodiments, the fluidic channels may have a diameter of from 0.02 in. to 0.05 in., e.g., the fluidic channels may be 0.030 in. in diameter (approximately 0.75 mm). In operation, the RPM of the rotor may range from 200 RPM to 120,000 RPM, such as from 1,000 RPM to 6,000 RPM. In embodiments, the parallel fluidic channels may be positioned on the rotor assembly at a distance of from 1 cm to 15 cm from the axis of rotation, and more particularly, at a distance of from 2 cm to 10 cm from the axis of rotation.

In embodiments, the fluidic channels may be parallel, substantially parallel, or may have another orientation relative to one another. Each channel may have the same length or may have a different length than another channel, and more or fewer than four (4) fluidic channels may be used. As described throughout this application, exemplary valve types are not limited, and may include wax valves, mechanical valves, or any other suitable valve type. In certain embodiments, no valve may be present in a particular channel.

As chamber and channel design may vary according to a particular application, a variety of valve configurations may be required. Specific valve configurations may include heat expanding valves, such as certain wax valves. In the case of heat expanding wax valves, examples of suitable wax materials include Ethylene Vinyl Acetate (EVA) wax and EVA blends. In embodiments, DuPont™ Elvax® 410 (ethyl-vinyl acetate copolymer resin) may be preferred. Such waxes may exhibit a narrow or "sharp" melting point and favorable flexibility and surface adhesion. Other waxes having characteristics similar to EVA may also be used.

In embodiments, the heat expanding material may further comprise a thermal absorbing compound to which radiant heat may be applied in order to activate the valve. Such configurations may be useful in microfluidic channels. Potential advantages of this embodiment are that the heat expanding material does not contact the fluid in the channel, which may cause contamination or thermal damage.

In embodiments, various other thermal actuators suitable for converting temperature change into a mechanical motion may also be adapted to act as a valve, i.e., to open or close a fluidic channel.

Described below are various valve designs according to embodiments of the present application.

Figure 14A:
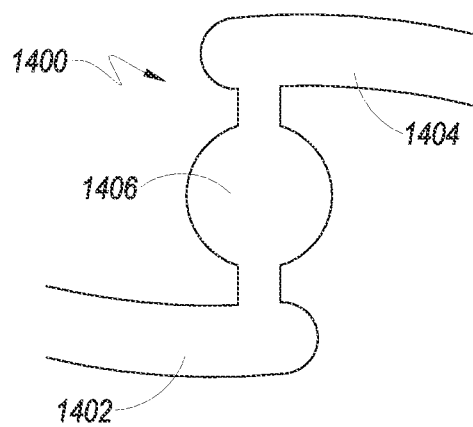
FIGS. 14A and 14B illustrate a "back loaded" valve according to an embodiment of the present application.
Figure 14B:
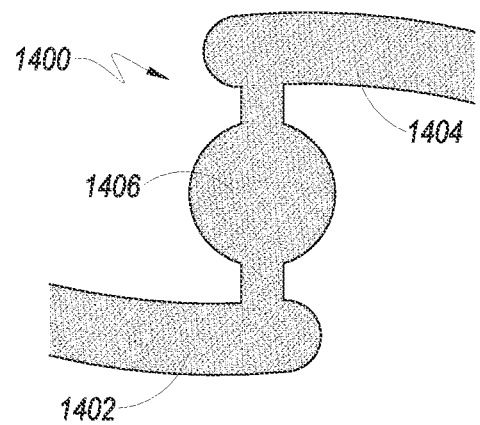

FIG. 14A and FIG. 14B illustrate a "back-loaded" valve according embodiments of the present application.

As shown in FIG. 14A, the back loaded valve 1400 includes fluid channels 1402, 1404 and a gravity well 1406. To obtain a back-loaded valve, a modular fluid separation cassette may be manufactured by an insert molding process. In this process, the cassette incorporates channels 1402, 1404 for the movement of valve material to be deposited in gravity well 1406 of valve 1400. During manufacture, a wax (e.g., EVA) or other suitable valve material may be introduced into the "back" of valve 1400. That is, wax is introduced to flow along the channel 1402 until it is deposited into the gravity well 1406. Any excess wax from well 1406 flows into channel 1404, as shown in FIG. 14B. In a post-injection step of this process, the excess wax is retained on the cassette. In embodiments, a 2 mm diameter (i.e., app. 4.2 µl) wax droplet or solid is dispensed into a "back" of a valve during manufacture. The wax then flows to achieve an active wax volume of approximately 0.5 µl.

Figure 15A:
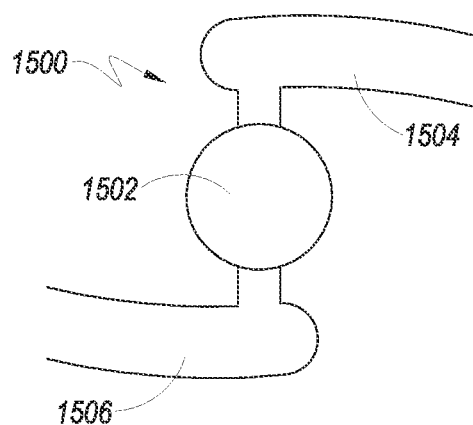
FIGS. 15A and 15B illustrate a "front loaded" valve according to an embodiment of the present application.
Figure 15B:
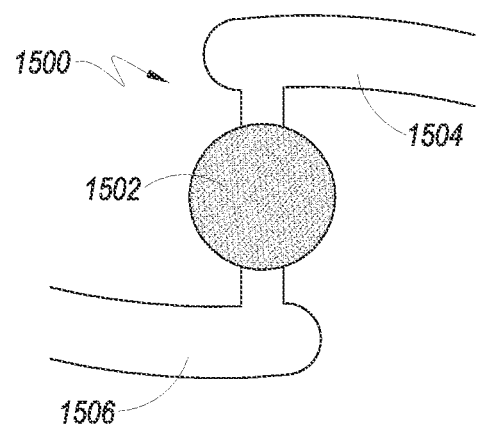

FIGS. 15A and 15B illustrate a "front loaded" valve according to an embodiment of the present application.

A front-loaded valve results from a manufacturing process whereby wax is deposited only directly on specified portions of the modular fluid separation cassette. As shown in FIGS. 15A and 15B, the front-loaded valve 1500 includes wax well 1502, and optionally includes channels 1504, 1506. Wax is deposited only into the top of well 1502 during production. That is, in contrast to the "back-loading" process described in connection with FIGS. 14A and 14B, in which fluid wax is pushed through a channel 1402 and deposited into a gravity well 1404 of a valve 1400, this process for obtaining a front-loaded valve deposits wax directly into well 1502. For example, an embodiment of a front-loaded valve may result from dispensing and melting into place a small volume droplet of EVA to accommodate an approximately 0.5 µl active wax volume, such as a 1 µl to 2 µl droplet. In a post-injection step in this process, excess wax must be shaved away from the modular fluid separation cassette.

Described below are various further valve designs, including embodiments of Normally Open Valves (NOVs) and Normally Closed Valves (NCVs). NOVs are valves which remain open during normal operation until they are actuated, whereas NCVs remain closed during normal operation.

Figure 16A:
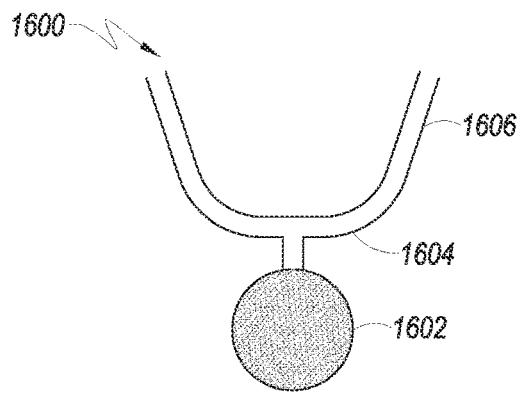
FIGS. 16A and 16B illustrate a NOV according to an embodiment of the present application.
Figure 16B:
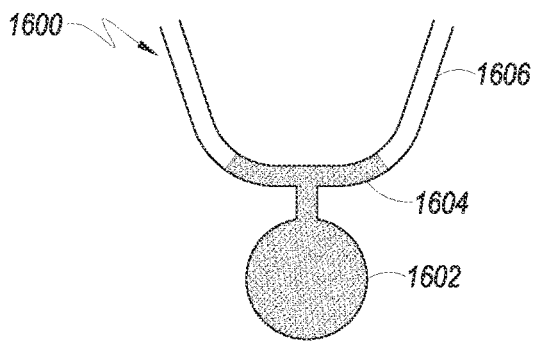

FIGS. 16A and 16B illustrate a Normally Open Valve (NOV) valve according to an embodiment of the present application.

As shown in FIGS. 16A and 16B, valve 1600 includes a gravity well 1602 in fluid connection with, and on the downhill or "outboard" side of (i.e., downhill or outboard in the G-field; on the distal side from the axis of rotation), bend 1604 in channel 1606. Wax is preloaded to fill the gravity well 1602.

FIG. 16A shows valve 1600 in an open position in its normal state. In this state, the wax remains in the well 1602 and does not obstruct the channel 1606. In this configuration, the valve 1600 is thus in a "normally open" position. In a heated or activated state, as shown in FIG. 16B, the wax expands into and obstructs the channel 1606, thereby causing the valve 1600 to assume a closed position. In this configuration, G-forces may not compliment actuation of this valve configuration when the valve 1600 is in the closed position since G-forces exert a pressure on the wax toward an open position. Nonetheless, this configuration may be preferable for particular applications.

Figure 17A:
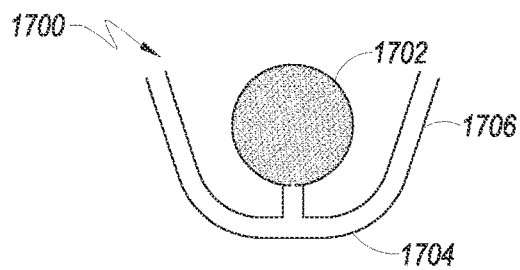
FIGS. 17A and 17B illustrate yet another NOV according to an embodiment of the present application.
Figure 17B:
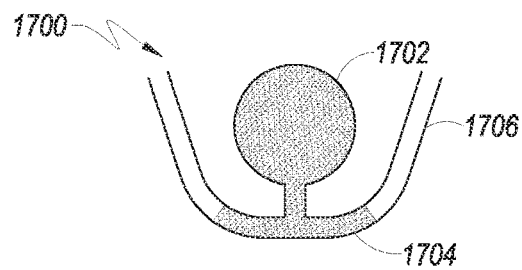

FIGS. 17A and 17B illustrate yet another NOV according to an embodiment of the present application.

As shown in FIGS. 17A and 17B, valve 1700 includes a gravity well 1702 in fluid connection with, and on the uphill or "inboard" side of (i.e., uphill or inboard in the G-field; on the proximal side from the axis of rotation), bend 1704 in channel 1706. Wax is preloaded to fill the gravity well 1702.

FIG. 17A shows valve 1700 in an open position in its normal state. In this state, the wax remains in the well 1702 and does not obstruct the channel 1706. FIG. 17B shows valve 1700 in a heated or activated state in which the wax has expanded into and is obstructing the channel 1706. In this configuration, G-forces may compliment actuation of this valve 1700 toward a fully closed state by exerting pressure on the wax toward the closed position.

Figure 18A:
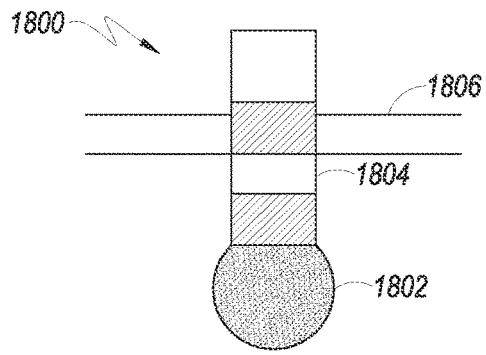
FIGS. 18A and 18B illustrate a Normally Closed Valve (NCV) according to an embodiment of the present application.
Figure 18B:
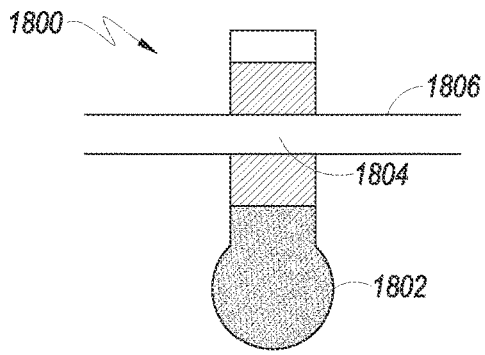

FIGS. 18A and 18B illustrate a Normally Closed Valve (NCV) according to an embodiment of the present application.

As shown in FIGS. 18A and 18B, valve 1800 includes a gravity well 1802 and a flow through portion 1804. Wax is preloaded to fill the gravity well 1802. FIG. 18A illustrates the valve 1800 in a normally closed position. Here, the valve is a NCV by including the flow through portion 1804 to be offset from the flow channel 1806 in the normal state. In its normal state, the wax remains in the well 1802 and does not act upon or drive the valve 1800. In a heated or activated state, the wax expands and drives the valve 1800, thereby causing the valve 1800 to assume an open position. FIG. 18B illustrates the valve 1800 in an open position after actuation such that flow through portion 1804 is in line with the fluid channel 1806.

Figure 19A:
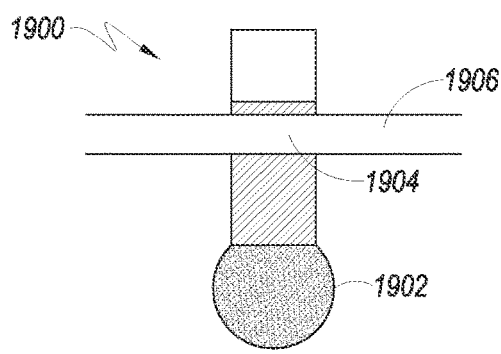
FIGS. 19A and 19B illustrate yet another NOV according to an embodiment of the present application.
Figure 19B:
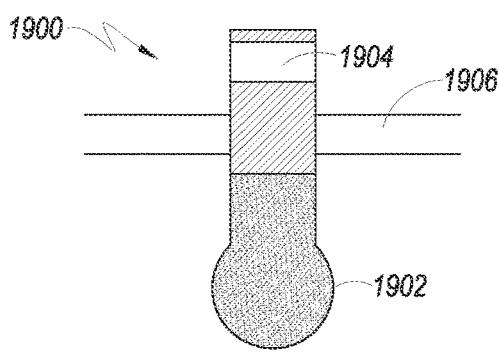

FIGS. 19A and 19B illustrate yet another NOV according to an embodiment of the present application.

FIGS. 19A and 19B illustrate a valve design similar to that shown in FIGS. 17A and 17B, but in a normally open configuration. As shown, valve 1900 includes a gravity well 1902 and a flow through portion 1904. Wax is preloaded to fill the gravity well 1902. In a normal state, flow through portion 1904 is in-line with the flow channel 1906. In its normal state, the wax remains in the gravity well 1902 and does not act upon or drive the valve 1900. In a heated or activated state, the wax expands and drives the valve 1900, thereby causing the flow through portion 1904 to be offset from flow channel 1906, thereby assuming a closed position.

Figure 20A:
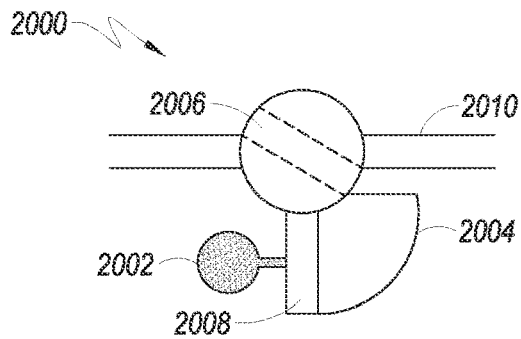
FIGS. 20A and 20B illustrate a rotary valve according to an embodiment of the present application.
Figure 20B:
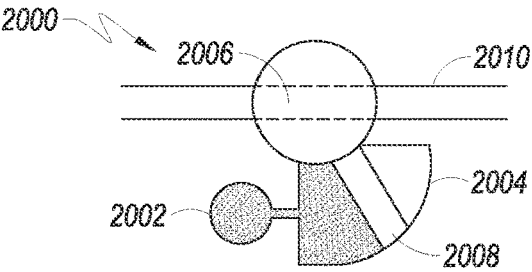

FIGS. 20A and 20B illustrate a rotary valve according to an embodiment of the present application.

As shown in FIGS. 20A and 20B, the valve 2000 includes a gravity well 2002 in fluid connection with a lever chamber 2004. The valve 2000 further includes a flow through portion 2006 situated within a fluid channel 2010, and a lever portion 2008 positioned in the lever chamber 2004. Wax is preloaded to fill the gravity well 2002.

In its normal state, shown in FIG. 20A, the wax remains in the well 2002 and does not act upon or drive the lever portion 2008. In the normal state, the flow through portion 2006 is offset from the fluid channel 2010, and no fluid can flow along fluid channel 2010. FIG. 20B shows the valve 2000 in an actuated or open state in which the wax has expanded and has driven the lever portion 2008, turning the valve 2000 to position the flow through portion 2006 to be in-line with channel 2010 allowing fluid to flow.

Figure 21A:
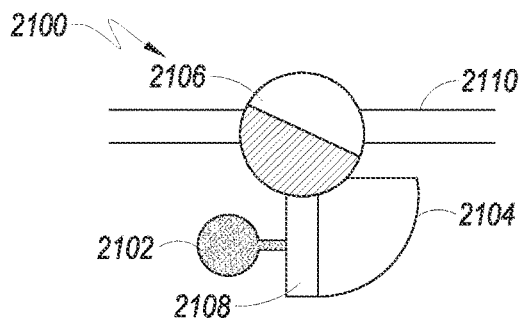
FIGS. 21A and 21B illustrate another rotary valve according to an embodiment of the present application.
Figure 21B:
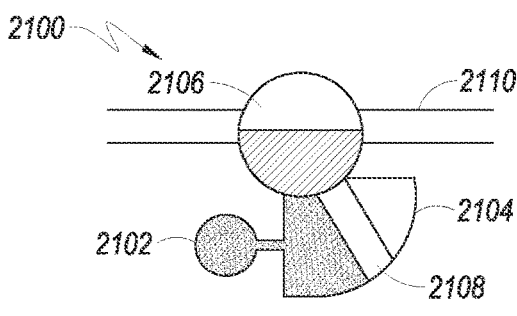

FIGS. 21A and 21B illustrate another rotary valve according to embodiments of the present application.

As shown in FIGS. 21A and 21B, the valve 2100 includes a gravity well 2102 in fluid connection with a lever chamber 2104. The valve 2100 further includes a flow through portion 2106 situated within a fluid channel 2110, and a lever portion 2108 positioned in the lever chamber 2104. Wax is preloaded to fill the gravity well 2102.

In its normal state, shown in FIG. 21A, the wax remains in the well 2102 and does not act upon or drive the lever portion 2108. In the normal state, the flow through portion 2106 is offset from the fluid channel 2110, and no fluid can flow along fluid channel 2110. FIG. 21B shows the valve 2100 in an actuated or open state in which the wax has expanded and has driven the lever portion 2108, turning the valve to place the flow through portion 2106 to be in-line with channel 2110 allowing fluid to flow.

In particular embodiments, using wax as a thermally activated material may not be desirable. Rather, a shape memory alloy or other heat activated memory material may be preferable.

Figure 22A:
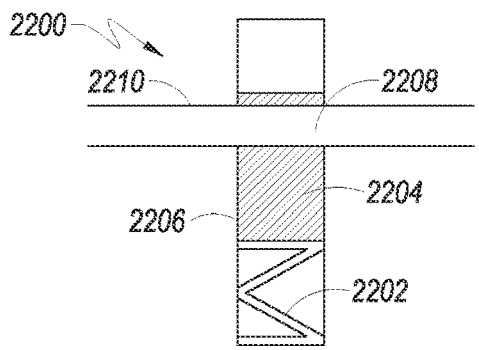
FIGS. 22A and 22B illustrate a shape memory alloy valve according to an embodiment of the present application.
Figure 22B:
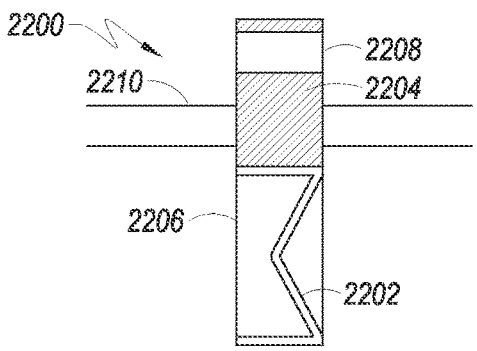

FIGS. 22A and 22B illustrate a shape memory alloy valve according to an embodiment of the present application.

As shown in FIGS. 22A and 22B, valve 2200 includes a shape memory alloy 2202, a mechanical valve portion 2204, a valve chamber 2206 and a flow through portion 2208. The shape memory alloy 2202 is preloaded to fill the valve chamber 2206, which bisects the fluid channel 2210. Mechanical valve portion 2204 is disposed in the valve chamber 2206 and is designed to open or to obstruct the channel 2210. In its normal or compressed state, as depicted in FIG. 22A, flow through portion 2208 is in line with the fluid channel 2210. Here, the shape memory alloy 2202 remains in the valve chamber 2206 and does not act upon or drive the mechanical valve portion 2204. In an activated state, the shape memory alloy 2202 expands and drives the valve 2200, thereby causing the valve 2200 to close. In the closed position, the flow through portion 2208 is offset from the flow channel 2210 to stop fluid flow in the channel 2110.

Figure 23A:
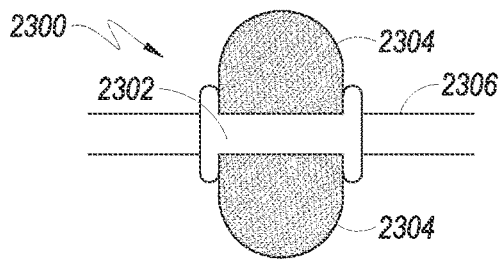
FIGS. 23A and 23B illustrate a soft tubing valve according to an embodiment of the present application.
Figure 23B:
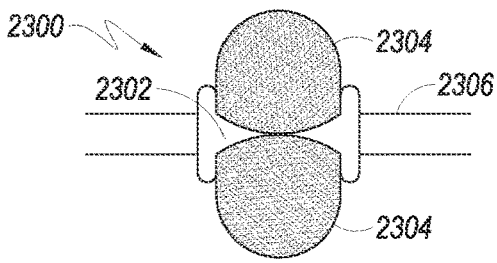

FIGS. 23A and 23B illustrate a soft tubing valve according to an embodiment of the present application.

As shown in FIGS. 23A and 23B, soft tubing valve 2300 includes soft tubing material 2302 and wells 2304 on either side of a fluid channel 2306. Wax is preloaded to fill wells 2304. In its normal or open state, as shown in FIG. 23A, the wax remains in the wells 2304 and does not act upon or compress the valve tubing 2302. In a heated or activated state, as shown in FIG. 23B, the wax expands and compresses or pinches the valve tubing 2302, causing the valve 2300 to assume a closed position.

Figure 24A:
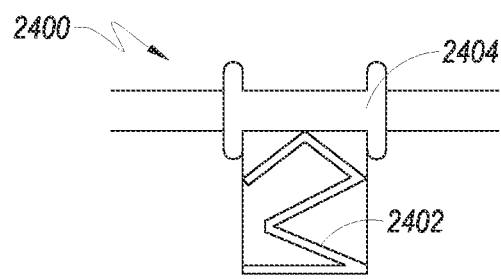
FIGS. 24A and 24B illustrate another soft tubing valve design according to an embodiment of the present application.
Figure 24B:
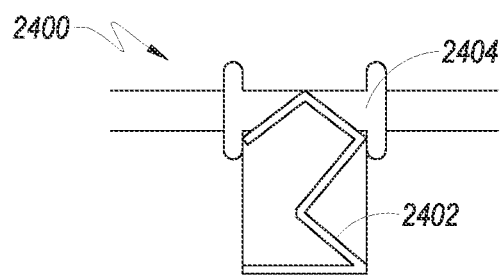

FIGS. 24A and 24B illustrate another soft tubing valve design according to an embodiment of the present application.

FIGS. 24A and 24B illustrate a valve design similar to that shown in FIGS. 23A and 23B, except that valve 2400 shown in FIGS. 24A and 24B incorporates a shape memory alloy 2402 as opposed to a heat activated wax for pinching soft tubing 2404. FIG. 24A shows the valve 2400 in an open position, whereas FIG. 4B shows the valve 2400 in a closed position.

Figure 25A:
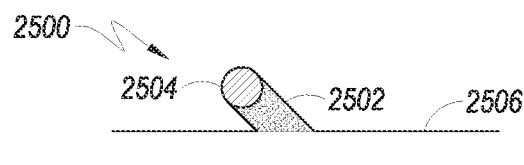
FIGS. 25A and 25B illustrate a ball and seat valve design according to an embodiment of the present application.
Figure 25B:
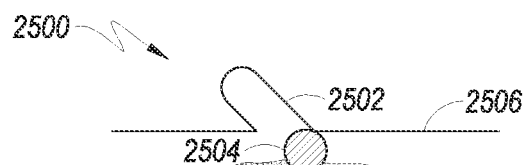

FIGS. 25A and 25B illustrate a ball and seat valve design according to an embodiment of the present application.

As shown in FIGS. 25A and 25B, the valve 2500 includes a wax well 2502 including a ball 2504 in fluid connection with a fluid channel 2506. In this configuration, wax is preloaded into the well 2502. A ball 2504 is then loaded into the well 2502 on top of the wax. In its normal or cooled state, shown in FIG. 25A, the wax remains in the well 2502 and does not act upon or drive the ball 2504. In a heated or activated state, shown in FIG. 25B, the wax expands and drives the ball 2504 into the channel 2506, thereby causing the valve 2500 to close.

Figure 26A:
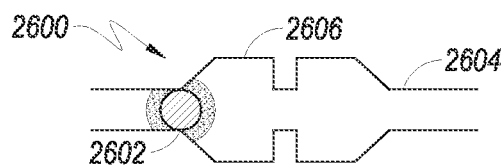
FIGS. 26A and 26B illustrate a ball valve according to an embodiment of the present application.
Figure 26B:
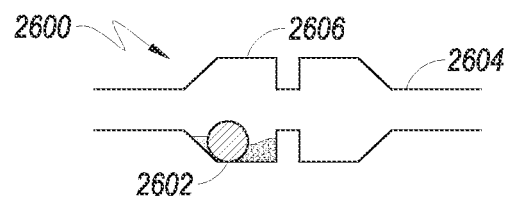

FIGS. 26A and 26B illustrate a ball valve according to an embodiment of the present application.

As shown in FIGS. 26A and 26B, the valve 2600 includes a ball 2602, a fluid channel 2604 and extended channel portions 2606. As shown in FIG. 26A, in its normal state, the valve 2600 includes the ball 2602 seated in wax, obstructing fluid channel 2604. In a heated or activated state, as shown in FIG. 26B, the wax melts and releases the ball 2602 into extended channel portions 2606 which allows fluid to flow through the channel 2604.

Figure 27A:
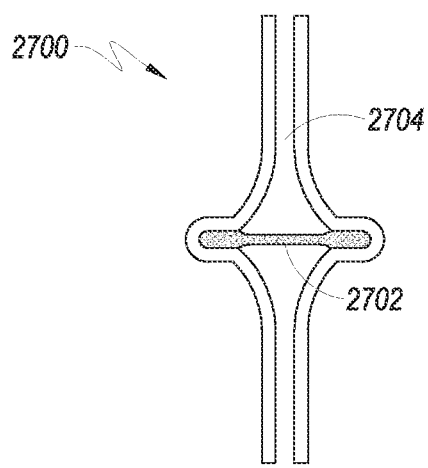
FIGS. 27A and 27B illustrate yet another NCV according to an embodiment of the present application.
Figure 27B:
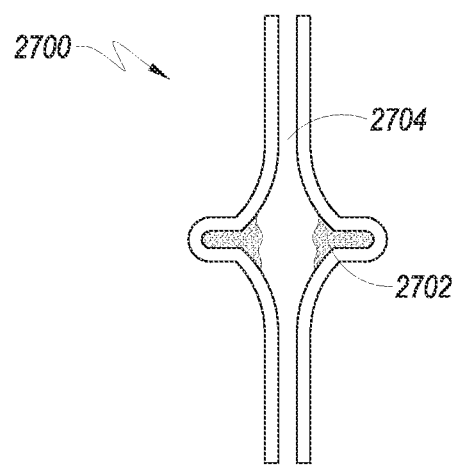

FIGS. 27A and 27B illustrate yet another NCV according to an embodiment of the present application.

As shown in FIG. 27A, valve 2700 includes a valve dam 2702 in a valve housing portion. Valve dam 2702 is constructed of hardened wax. In its normal, closed state NCV 2700 obstructs fluid pathway 2704. Upon actuation, as shown in FIG. 27B, valve dam 2702 falls away, allowing fluid to flow along the fluid pathway 2704.

The NCV 2700 of FIG. 27 may offer unique advantages based upon any of its method of manufacture, its geometry, or its method of actuation. The valve 2700 of FIG. 27 is made using an insert mold of injected wax allowing for a fine control of the valve shape. Consequently, a very thin and long dam of wax can be achieved across a fluidic channel. Once heated, fluid can push over and through the dam, or an orifice can be formed in the channel, allowing fluid to flow.

Disclosed below are additional NOV designs, including those for utilizing both crystalline and amorphous heat activated materials. Valve designs described below may use a combination of expansion and centripetal forces to move wax.

FIGS. 28A to 28C illustrate a NOV 2800 designed to utilize a crystalline heat activated material.

As depicted in FIGS. 28A to 28C a crystalline material (e.g., crystalline wax) is deposited into a well 2802 which is connected via channels 2804 to a fluidic flow channel 2806. The area of the fluidic flow channel 2806 which is near channels 2804 is undulated. As the crystalline material is heated, it expands and fills the fluidic flow channel 2806. Upon cooling, the restrictions in the channel (due to the undulations) control the contraction of the wax in order to ensure that a seal is held. Although this design can be accomplished with a singular port into the fluidic flow channel (as depicted in FIGS. 29A to 29C below), a two-port design allows for air or fluid to displace the wax to ensure pressure upon cooling. This design can use a combination of expansion and contraction to move wax.

FIGS. 29A to 29C illustrate a NOV designed to utilize an amorphous heat activated material.

As shown in FIGS. 29A to 29C, this valve design is essentially the same is that depicted in FIGS. 28A to 28C. In FIGS. 29A to 29C, an amorphous material (e.g., amorphous wax) is deposited into a well 2902 which is connected via channels 2904 to a fluidic flow channel 2906. In air, (FIG. 29B) the wax flows out of the "lower" (i.e. further down the G-field; more distant from the axis of rotation) channel 2904 to occlude the fluid flow channel 2906 as it is displaced by air. In fluid, (FIG. 29C) the wax can be less dense than the fluid, which allows the wax to flow out of the "top" (i.e. further up the G-field; less distant from the axis of rotation) channel 2904 as it is replaced with the more dense fluid underneath. Amorphous wax may ensure improved contact with the walls of the fluid channel upon cooling due to its lack of contraction.

FIGS. 30A to 30C illustrate yet another NOV according to an embodiment of the present application.

The valve 3000 illustrated in FIG. 30A to FIG. 30C incorporates a pre-formed wax cartridge 3002 that is placed into a wax chamber 3004 that has equivalent shape and volume to the cartridge 3002. Upon heating and melting of the cartridge 3002, molten wax flows from the chamber 3004 through an escape port 3006 which joins the chamber 3004 to the fluid pathway 3008 to be blocked. In this embodiment, undulated fluid pathway 3008. Notably, the undulations of the fluid pathway 3008 may provide redundancy for an improved seal in this and in other valves described in this disclosure.

Due to phase change volumetric expansion of the wax within the confining chamber 3004, molten wax is forced to flow into the fluid pathway 3008 and thereby obstruct the pathway 3008. The shape of the pathway 3008 is designed such that freezing dynamics of the molten wax is controlled. Shape must be chosen to assure that, upon freezing in the fluid path 3008, phase change shrinkage does not cause the pathway to re-open. This can be accomplished by properly positioning regions within the pathway 3008 so that molten wax therein remains fluid (unfrozen) until other regions have already frozen. Because these regions are last to freeze, shrinkage voids are formed within these predetermined regions while the first-to-freeze regions experience no shrinkage. The integrity of the wax plug 3002 thus is maintained. First-to-freeze regions are generally shaped to have high local surface area to local wax volume ratios. Thus, heat transfer from the molten wax is rapid. Last-to-freeze regions are generally shaped to have low local surface area to local wax volume ratios. Heat transfer from the molten wax is therefore slower and thus freezing is slower. It should be noted that heat provided to the chamber 3004 might be controlled so that the molten wax is maintained for an extended period while freezing in the fluid path 3008 takes place. This further assures that shrinkage in the fluid path 3008 might be replaced with molten wax from the chamber 3004.

Described below are various views and features of embodiments of an Injectable Channel (IC) NOV according to embodiments of the present application, including a related method of manufacture.

In embodiments, the IC NOV utilizes an injectable channel design. That is, during an injection process, an injection plate with a channel feature is placed over an injection cavity (i.e., a valve well). As a molten, heat activated material (e.g., a wax) is introduced into the well, the channel feature of the injection plate obstructs the wax in the shape of a fluidic flow channel. Once the wax cools and the injection plate is removed, and the solidified wax filling the injection cavity (i.e., including the void created in the solidified wax by the channel feature in the shape of the fluidic flow channel) constitutes the IC NOV. The following figures and descriptions describe the IC NOV in further detail.

Figure 31A:
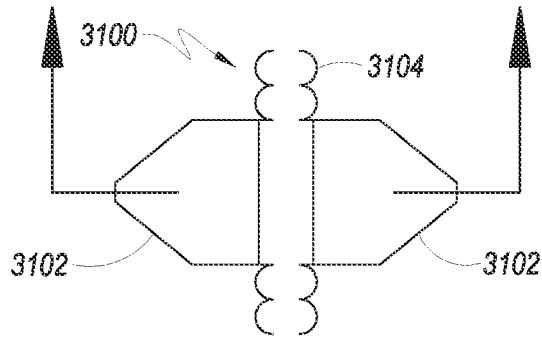
FIGS. 31A and 31B illustrate an Injectable Channel (IC) NOV according to an embodiment of the present application.
Figure 31B:
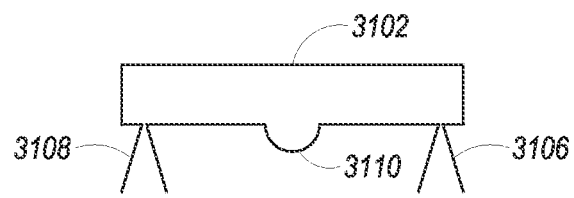

FIGS. 31A and 31B illustrate an Injectable Channel (IC) NOV according to an embodiment of the present application.

FIG. 31A is a top view of the IC NOV 3100 in an empty state. In FIG. 31A, the injection cavity 3102 of the IC NOV 3100 forms an opening in the form of an undulated fluidic flow path 3104.

FIG. 31B is a cross sectional view of the IC NOV 3100 in an empty state. In FIG. 31B, IC NOV 3100 is shown as including an injection cavity 3102, an extended portion 3110 positioned opposite the portion of the injection cavity 3102 in which a flow channel 3212 (shown below) will be formed in molten wax, an injection port 3106 and a vent 3108. The injection port 3106 is the point of injection for the molten heat activated material (e.g., the wax) into the injection cavity 3102. Vent 3108 allows air to escape during the introduction of wax into the injection cavity 3102.

Figure 32A:
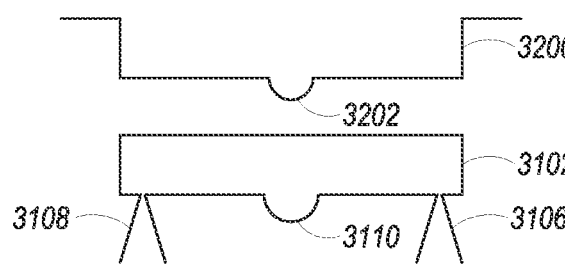
FIGS. 32A to 32C illustrate an injection plate in combination with an injection cavity in the manufacture of an IC NOV according to an embodiment of the present application.
Figure 32B:
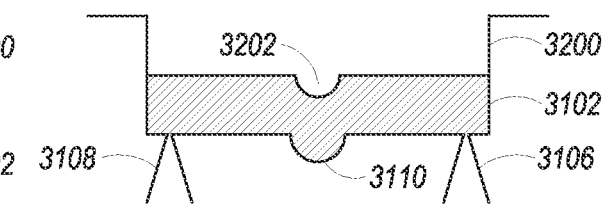
Figure 32C:
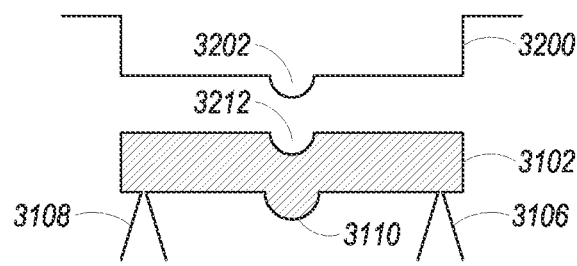

FIGS. 32A to 32C illustrate an injection plate in combination with an injection cavity in the manufacture of an IC NOV according to an embodiment of the present application.

FIG. 32A is a cross sectional front view of an injection plate 3200 directly above the injection cavity 3102 of FIGS. 31A and 31B. The injection plate 3200 has a channel feature 3202 for creating a flow channel 3212 (shown below) when the injection plate is placed in contact with molten wax of the injection cavity 3102.

FIG. 32B is a cross sectional front view of an injection plate 3200 being pressed downward and in direct contact with the injection cavity 3102. As shown in FIG. 32B, injection plate 3200 includes channel feature 3202. Injection cavity 3102 includes vent 3108 and injection port 3106. Injection cavity 3102 further includes an extended portion 3110 positioned opposite the channel feature 3202 of injection plate 3200. In FIG. 32B, wax fills the injection cavity 3102 through injection port 3106, and air escapes through vent 3108. The molten wax fills the injection cavity 3102, including extended portion 3110, and channel feature 3202 forms a flow channel 3212 in the molten wax. Advantages of incorporating extended portion 3110 in to this valve configuration include the ability of wax to fill the injection cavity more evenly during production and the ability to achieve a more uniform wax thickness.

FIG. 32C depicts the injection plate 3200 disjoined from the injection cavity 3102. That is, the wax has cooled sufficiently to allow the formation of the IC NOV 3100, and injection plate 3200 has been removed, leaving injection cavity 3102 (including extended portion 3110) filled with solidified wax and leaving a flow channel 3112 in the wax in the form of channel feature 3202.

FIGS. 33A to 33D illustrate an IC NOV accommodating a variety of materials according to embodiments of the present application.

Figure 33A:
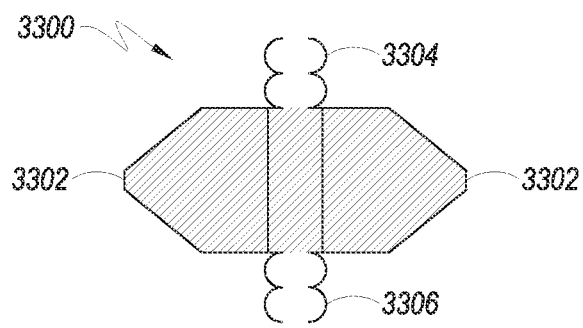
FIGS. 33A and 33D illustrate an IC NOV accommodating a variety of materials according to embodiments of the present application.

FIG. 33A is a top view of IC NOV 3300 including an injection cavity 3302 and undulated flow path portions 3304, 3406. IC NOV 3300 is shown in an open mode, and injection cavity 3302 is filled with wax or any suitable heat actuated material described herein.

Figure 33B:
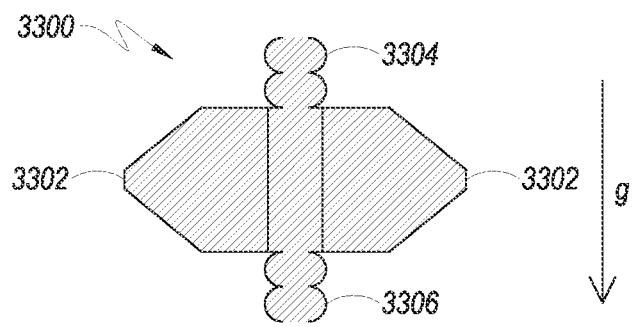

FIG. 33B is a top view of IC NOV 3300 after actuation (i.e., in a closed mode) in which heat has been applied and the heat actuated material (i.e., the wax) has moved throughout the injection cavity 3302 and into adjacent undulated portions of the flow path 3304, 3306 thereby effectively collapsing the flow channel and closing the valve 3300.

Figure 33C:
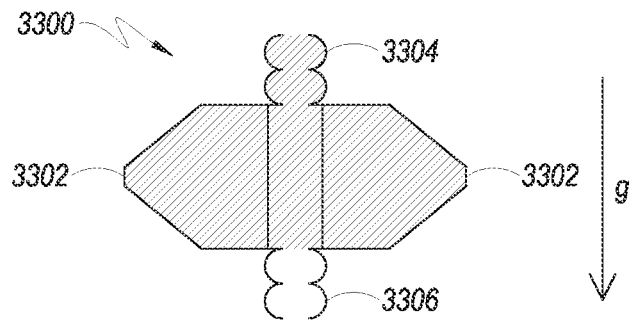

FIG. 33C is top view of IC NOV 3300 in case in which the heat actuated material (i.e., the wax) is of a lower density than the fluid in the flow channel. In this case, the IC NOV 3300 is also shown after actuation in a closed mode in which heat has been applied and wax has moved throughout the injection cavity 3302, yet the wax has further moved to only the adjacent flow path area 3304, which is inboard from the injection cavity 3302, nearer the axis of rotation. This occurs because the lower density wax may "float" on the fluid in the flow path when subjected to G-forces.

Figure 33D:
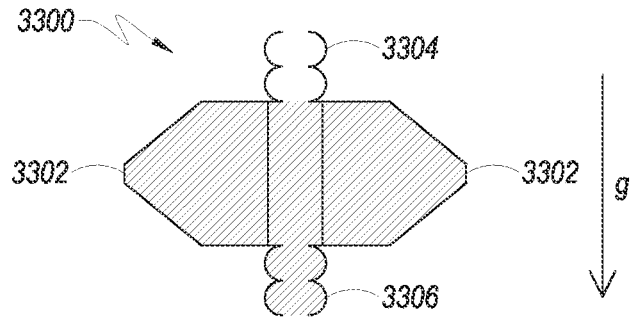

FIG. 33D is a top view of IC NOV 3300 used along an air path. FIG. 33D also illustrates IC NOV 3300 after actuation in a closed mode in which heat has been applied and actuated wax has moved throughout the injection cavity 3302. In this case, the wax has further moved to only the adjacent undulated flow path 3306, which is outboard from the injection cavity 3302, further from the axis of rotation. This occurs because the density of wax is greater than the density of the air in the flow channel, causing the wax to flow outward from the injection cavity 3302 when subjected to G-forces.

Notably, the valves depicted in each of FIGS. 33B-33D would appear the same as one another from a cross sectional view when in the closed mode since the actuation of each design results in a collapsed flow channel.

There are many benefits and technical advantages to IC NOVs. In particular, IC NOVs described in FIGS. 31A to 33D rely on cohesion. That is, the molten wax coheres to itself when activated in order to provide the valve closing mechanism. In this respect, IC NOVs take advantage of the natural affinity of certain heat actuated materials for themselves, which results in improved valve integrity, a faster closure rate, and the ability to close larger valves effectively. This natural affinity of wax for itself may be most pronounced in the molten state. Another potentially advantageous aspect of this design is that each portion of the heat actuated material which coheres to itself is heated to a similar temperature during actuation. In contrast, other heat actuated valve types may rely on adhesion, i.e., the wax creating a channel closure by wax adhering to a dissimilar material. A further distinction from adhesion occurs when, during actuation, the dissimilar material is not heated.

The IC NOV design described herein also allows a greater volume of wax to be heated in relation to the empty volume of the flow channel in its open state. That is, in the IC NOV, a greater volume of the wax surrounding the flow channel is heated as compared to other valve designs, thereby collapsing the walls of the flow channel inward toward each other more effectively. More specifically, embodiments of the IC NOVs may contrast with valve designs in which heat actuated material proceeds in only one direction or not toward itself, and valve designs in which the heat actuated material is expected to adhere to a material which is dissimilar or in a dissimilar state. The foregoing features of the IC NOVs allow for larger channels to be closed as effectively as smaller channels using other valve designs. Additionally, as noted above, a further advantage of the IC NOV is that the injection cavity utilizes an extended portion (see 3110 of FIG. 31B) which protrudes outward opposite the channel feature of the injection plates. This outward protrusion may result in a more uniform injection cavity once joined with the injection plate, thereby allowing for a more rapid, even and uniform fill. Another advantage is that, in an open mode, the IC NOV interfaces with and forms a portion of a flow channel having a geometry and volume that is substantially the same as other portions of the flow channel. In this respect, the IC NOV will not impede flow as other valve types may, even when deployed in applications involving slower flow rates, such as in the case of sedimentation through a valve in a Multi-Use Chamber. Further, the IC NOV design accommodates a variety of materials across a variety of applications. For instance, the use of a more crystalline wax will cause further expansion of the wax into adjacent flow channel areas upon actuation, whereas the use of a more amorphous wax may feature the buoyancy of the wax or the weight of the wax in the G-field to achieve channel closure. The ability to choose a particular wax for a particular application may also allow for the use of a wax which does not separate from injection cavity walls or crack during solidification. For these and other reasons, IC NOVs provide improved structural integrity and a more reliable channel closure.

Various embodiments and combinations of features not specifically enumerated are within the scope of this disclosure. For example, some embodiments may utilize a heat actuated material that expands, whereas other embodiments do not require expansion. As another example, some embodiments may utilize a different geometry in one or both of the flow channel portions adjacent to an injection cavity in order to aid in valve closure. As another example, some embodiments may require machining out of the wax to form the flow channel as opposed to using an injection plate with a channel feature. As another example, the orientation and placement of the flow channel and the injection cavity may be adjusted relative to one another. Likewise, a variety of injection cavity designs may be used. In a particular example, an embodiment may include a relatively larger section of injection cavity positioned inboard of the flow channel along with a relatively heavy wax. In such a configuration, the G-Field would "push" a greater volume of wax in a downhill direction toward the flow channel thereby closing the channel more effectively. These and many other combinations can be readily envisaged with the benefit of the disclosures made herein In various embodiments including any of the valve types described herein, the valve portions and the fluid channel in connection therewith may further incorporate raised banks along their respective sides which define a flow path. These raised banks may aid in securing a resistor array or layer thereof (discussed below), to the modular fluid separation cassette, and may help maintain the integrity of the fluid pathways and valve portions throughout production and use of the modular fluid separation cassette. For instance, the raised banks may aid the resistor array in being combined with the remainder of the modular fluid separation cassette during welding or other suitable manufacturing process.

In embodiments, a modular fluid separation cassette may incorporate more than one valve-type. For example, a NOV may be used in the separation of waste or the collection of product in a modular fluid separation cassette concurrently with a NCV that is used in the introduction of media to the separation chamber. Likewise, a single modular fluid separation cassette may incorporate one or both of back-loaded and front-loaded valve types, or may include variations of one type of valve, and more than one valve may be implemented in series. Several alternative valve designs and combinations may also exist within a single modular fluid separation cassette, and several further embodiments of suitable valve configurations may be readily envisaged.

In embodiments, each modular fluid separation cassette may have any of a number of valves. For example, a modular fluid separation cassette may 1-20 valves, and more particularly, a single modular fluid separation cassette may include equal to or less than 8 valves. Exemplary heat expanding waxes may form various shapes and dimensions. For example, a wax plug may range from 0.005 to 0.017 inches thick, and more particularly, from 0.008 to 0.013 inches thick.

Waxes and heat expanding materials used in the valve types described herein may exhibit particular physical characteristics and may be associated specific processing and handling temperature constraints. For example, the wax material may be suitable for ETO sterilization at 131° F. (55° C.) in a vacuum, or for steam sterilization at 273° F. (134° C.) and 3 bar of pressure. In embodiments, suitable wax materials may also be capable of being transported as freight in accordance with ASTM standards. For instance, suitable materials may be capable of being transported in a tropical climate of 104° F.±4° F. (40° C.±2° C.) and 90%±5% Relative Humidity (RH), and in a desert climate of 140° F.±4° F. (60° C.±2° C.) and 15%±5% RH. In embodiments, the material used for the wax may exhibit no, or substantially no, visible particles or visible discoloration.

In embodiments incorporating heat expanding valves, the modular fluid separation cassette includes a means of thermal actuation, i.e., a heating element. In use, a heating element serves to heat the wax in the gravity well in order to actuate the valve into an "open" or a "closed" position. When wax valves are heat activated, such as valves made from EVA, a resistor array or similar thermal actuation means may be employed to heat the valve material. In embodiments, actuation of the valve occurs by arranging a resistor to be proximal to a gravity well holding the wax. The resistor may be printed on a film and arranged above, below or near the wax in the modular fluid separation cassette. Alternatively, resistors may be disposed in the rotor assembly. In operation, current is sent through the resistor(s) to generate sufficient heat to melt the wax. The wax then expands into the channel to achieve a closed position, or alternatively, expands so as to open a channel.

In embodiments, a resistor array may comprise a portion of the modular fluid separation cassette which is incorporated into the cassette after the construction of the fluid channels and the valve portions, and which may form a top portion of the modular fluid separation cassette. The resistor array may comprise multiple layers. For example, the resistor array may comprise a resistor layer, an insulating layer and an adhesive layer (not shown). Optionally, any combination of these and other layers may be integrated so as to comprise fewer layers.

In embodiments, the resistor layer may have a top portion exposed to the outside of the modular fluid separation cassette. The top portion of the resistor layer may be decorated for visual appeal. The resistor layer may also have a bottom portion. The bottom portion of the resistor layer may be a printed portion comprising an array of resistors printed thereupon.

In embodiments, the insulating layer serves to insulate the exposed resistor array to prevent grounding. In various embodiments, the insulating layer may exhibit particular compliance characteristics to facilitate bonding of the resistor array to the remainder of the modular fluid separation cassette.

In embodiments, the adhesive layer serves to adhere the resistor array to the remainder of the modular fluid separation cassette. The adhesive layer may exhibit particular pressure sensitivity characteristics and thermal sensitivity characteristics which facilitate bonding. Examples of material used for the adhesive layer include silicon, such as a 10 ml silicon layer. In further embodiments, channels and valves may be formed into, or cut out of (e.g., die cut), the silicon layer during the manufacturing process, thus forming the one or more of the various channels or fluid flow paths between the chambers of the modular fluid separation cassette.

An interface between a resistor and a wax deposit arranged in a valve portion of a cassette may range from 0.0001 to 0.015 inches, for example, the resistor and the wax may be from 0.005 to 0.010 inches apart. In embodiments, the actuating of a resistor with between 10V and 20V may result in a temperature increase of approximately 100° C. in as few as 5 seconds, and greater temperature increases can be achieved with the application of voltage over greater time periods. Voltage increases between 10V and 20V can cause an increase in temperature of an exemplary resistor from approximately 60° C. to 165° C. in 15 seconds.

In embodiments, the resistor array may include or be controlled by a variety of electronic control means and may further include electronic communication means. For example, the resistor array may include or be controlled by any of one or more processors, embedded code, integrated hardwiring or circuitry, embedded sensors, or any other electronic means which may allow for one-way or for bi-directional communication to and from the resistor array, and which may allow for monitoring, assessment and control of any of the resistors on the rotor assembly, resistors on the resistor array, the valves, the chambers and the channels within any cassette affixed thereto, and any other system component.

FIG. 34 to FIG. 37 illustrate a resistor array according to embodiments of the present application.

Figure 34:
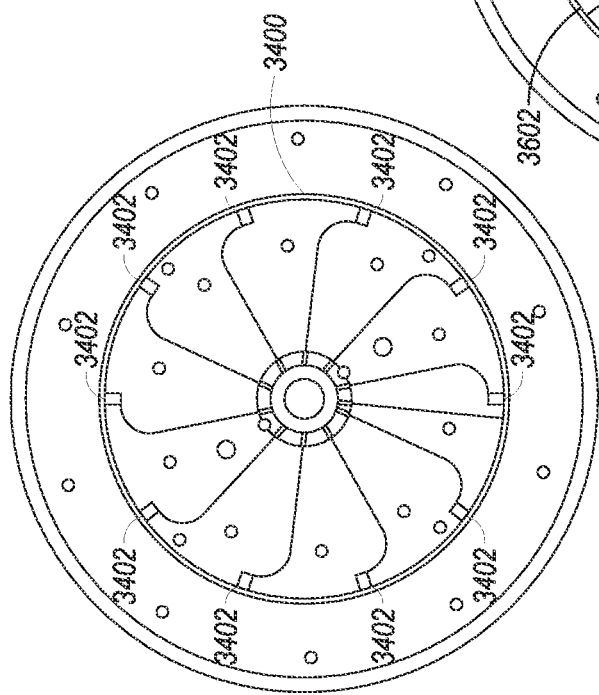
FIG. 34 illustrates a disk-shaped resistor array according to an embodiment of the present application.

Referring to FIG. 34, the resistor array 3400 forms a printed circuit layer including heating elements (i.e., resistors) 3402 for actuating valves in a modular fluid separation cassette. The resistor array 3400 is circular in shape and accommodates a disk-shaped cassette.

Figure 35:
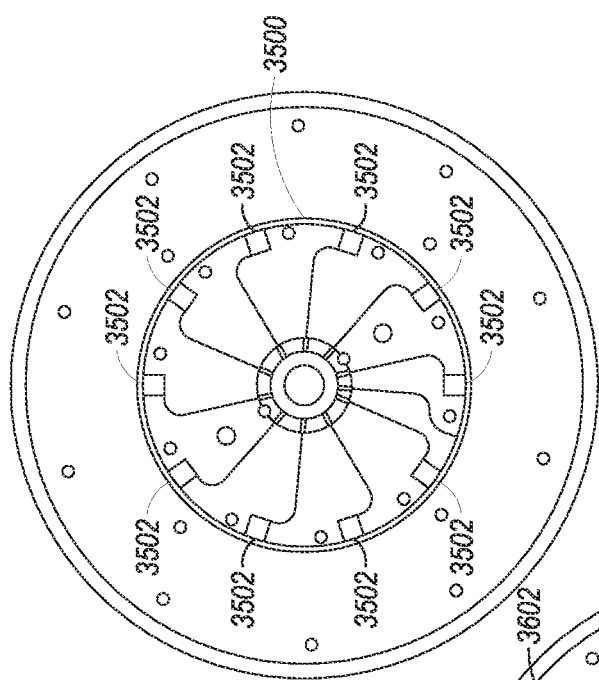
FIG. 35 illustrates another disk-shaped resistor array according to an embodiment of the present application.

Referring to FIG. 35, the resistor array 3500 forms a printed circuit layer including heating elements (i.e., resistors) 3502 for actuating valves in a modular fluid separation cassette. The resistor array 3500 is circular in shape and accommodates a disk-shaped cassette. The resistors 3502 of the embodiment in FIG. 35 are further inboard than the resistors 3402 of FIG. 34. The resistors 3502 of FIG. 35 are also larger than the resistors 3402 shown in the embodiment of FIG. 34.

Figure 36:
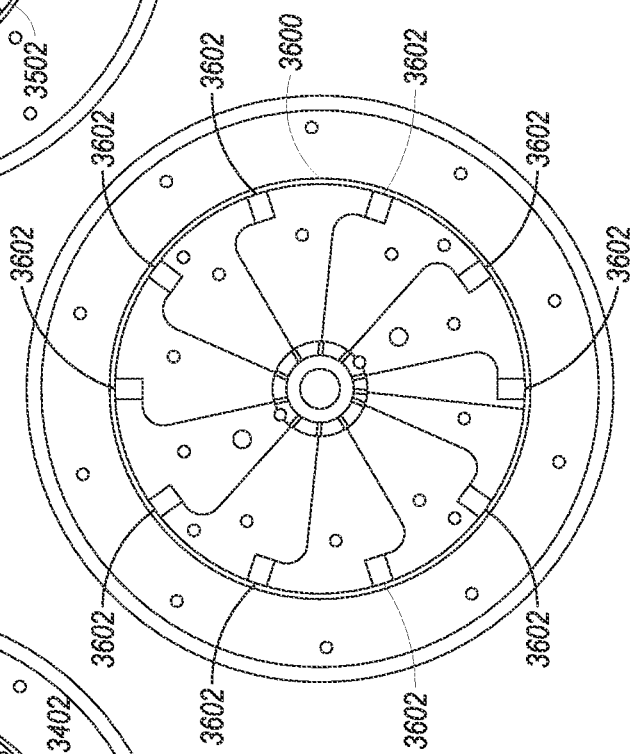
FIG. 36 illustrates yet another disk-shaped resistor array according to an embodiment of the present application.

Referring to FIG. 36, the resistor array 3600 forms a printed circuit layer including heating elements (i.e., resistors) 3602 for actuating valves in a modular fluid separation cassette. The resistor array 3600 is circular in shape and accommodates a disk-shaped cassette. The resistors 3602 of the embodiment in FIG. 36 are further outboard than the resistors 3502 of FIG. 35. The resistors 3602 of FIG. 36 are also larger than the resistors 3502 shown in FIG. 35.

Figure 37:
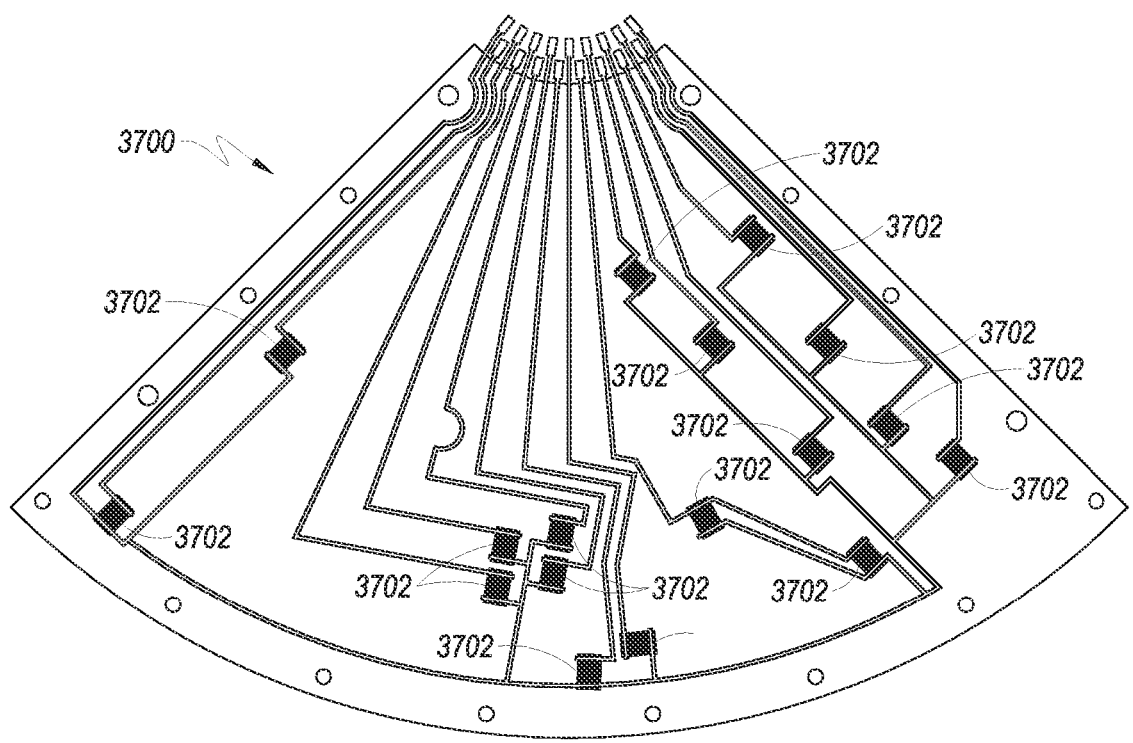
FIG. 37 illustrates a wedge-shaped resistor array according to an embodiment of the present application.

Referring to FIG. 37, the resistor array 3700 is arranged in wedge-shaped configuration. The resistor array 3700 forms a printed circuit layer including heating elements (i.e., resistors) 3702 for actuating valves in a modular fluid separation cassette. The resistor array 3700 of FIG. 37 is an example of a resistor array that may be incorporated into the cassette 3800 shown in FIG. 38. Notably, the location of the resistors 3702 of FIG. 37 corresponds with the location of the valves 3826, 3828 of cassette 3800 shown in FIG. 38 as each resistor 3702 is designed to be capable of thermally actuating a valve once the array is incorporated into the cassette 3800 or layer thereof.

In operation, once the resistor arrays described herein are incorporated into a cassette or layer thereof, control of the resistor array allows for control of valves variously positioned throughout the cassette. Control of the valves throughout the cassette allows for control of the fluid throughout the cassette during centrifugation. Each embodiment of FIG. 34 to FIG. 37 utilizes a slightly different shape and arrangement of elements. The shape and arrangement of elements on the resistor array can be variously optimized for any particular application, design or material type.

Figure 38:
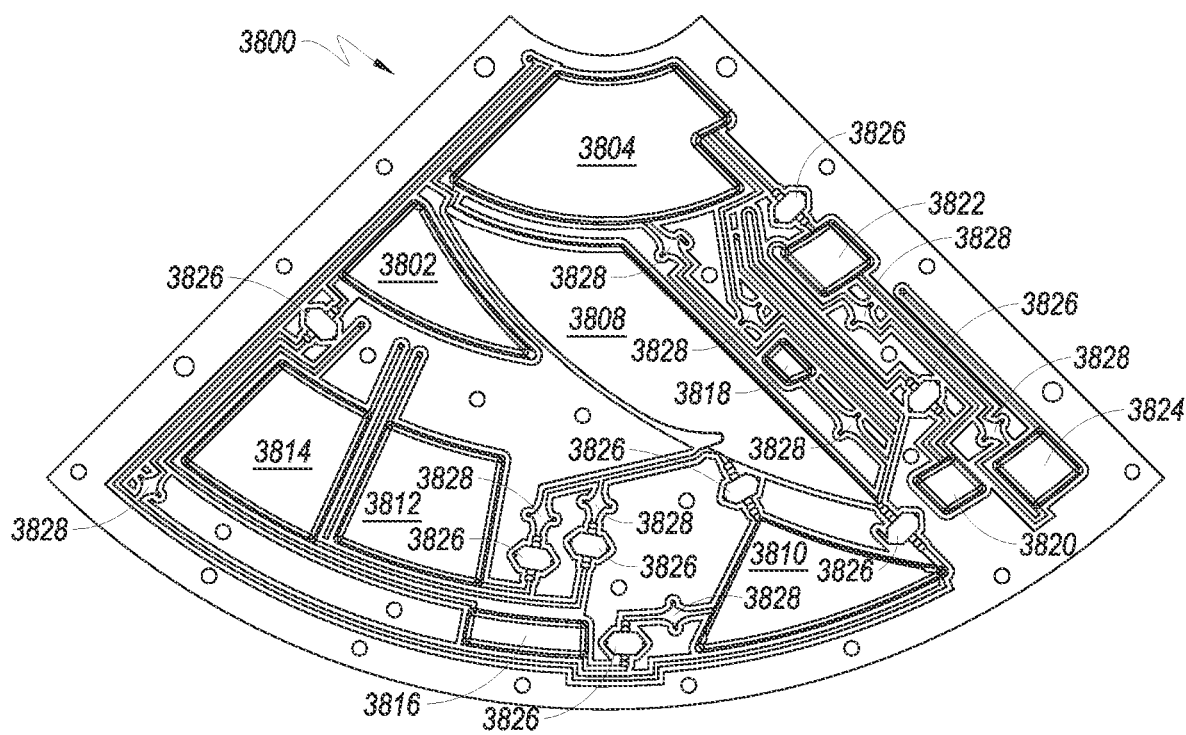
FIG. 38 is a top view of a modular fluid separation cassette according to an embodiment of the present application.

FIG. 38 is a top view of a modular fluid separation cassette according to embodiments of the present application.

As shown in FIG. 38, the modular fluid separation cassette 3800 includes a first separation media chamber 3802; a wash reservoir 3804; a two-part separation portion (shown as 4406 in FIG. 44) including a separation/wash section or chamber 3808 and a separation/heavy waste section or chamber 3810; a first light waste chamber 3812; a second light waste chamber 3814; a plasma chamber 3816; a media chamber 3818; a final chamber 3820; a pulley power chamber 3822; a pulley waste chamber 3824; various NOVs 3826 and various NCVs 3828.

To use the cassette of FIG. 38, whole blood is loaded into the upper section of the separation chamber 3808. Density gradient media is loaded into the separation media chamber 3802. Phosphate-Buffered Saline (PBS) or other cell washing media is loaded into the wash reservoir 3804. Cell suspension or storage media is loaded into the media chamber 3818. As the cassette is spun in a centrifuge, the pulley power chamber 3822 is loaded with fluid from the wash reservoir 3804; whole blood flows into the separation/heavy waste section 3810 of the two-part separation portion (shown as 4406 in FIG. 44) from the separation/wash section 3808, leaving the separation/wash section 3808 empty; and blood cells in the separation/heavy waste section 3810 sediment and separate from plasma. The NCV 3828 between the separation/heavy waste section 3810 and plasma chamber 3816 is then opened to transfer some of the plasma layer from the separation/heavy waste section 3810 into the Plasma chamber 3816. Next, the NCV 3828 Valve between separation/heavy waste section 3810 and plasma chamber 3816 is closed to block the fluid pathway. Next, the NCV 3828 between the separation media chamber 3802 and the separation/heavy waste section 3810 is opened to push the density gradient media under the remaining whole blood in the separation/heavy waste section 3810. Next, the NOV 3826 between the separation media chamber 3802 and the separation/heavy waste section 3810 is closed to block the fluid pathway. Next, time is elapsed to separate mononuclear cells (PBMCs) from red blood cells (RBCs) and granulocytes, with PBMCs rising into the separation/wash section 3808 and RBCs and granulocytes sedimenting into the separation/heavy waste section 3810. Next, the NOVs 3826 between the separation/heavy waste section 3810 and the separation/wash section 3808 of the two-part separation portion are closed to isolate the sections from one another. Next, NCV 3828 valve between wash reservoir 3804 and the separation/wash section 3808 is opened to suspend the contents of the separation/wash section 3808 (now the wash chamber) in wash media. Next, time is elapsed as cells sediment in separation/wash section 3808 (i.e., wash chamber). Next, the NCV 3828 between the wash chamber 3803 and the light waste chamber 3812 is opened to drain supernatant fluid from the wash chamber 3808 into the light waste chamber 3812 (LW1). Next, the NOV 3826 between the wash chamber 3808 and the light waste chamber 3814 is closed. Next, the NCV 3828 between the wash reservoir 3804 and the separation/wash section 3808 is opened to suspend the contents of the wash chamber 3808 a second time, and time is elapsed as cells sediment. Next, the NCV 3828 between the wash chamber 3808 and the light waste chamber 3814 (LW2) is opened to drain supernatant fluid from the Wash chamber into LW2. Next, the NOV 3826 between the wash chamber 3808 and the light waste chamber 3814 (LW2) is closed. Next, the NCV 3828 between the separation/wash section 3808 and the media chamber 3818 is opened to suspend the contents of the Wash chamber in suspension/storage media. Next, the valve between the wash reservoir 3804 and the pulley power chamber 3822 is closed to isolate the Wash Reservoir from the Pulley Power chamber. Next, the NCV 3828 between the final chamber 3820 and the pulley power chamber 3822 is opened to open the vent connecting the final chamber 3820 and the pulley power chamber 3822. Next, the NCV 3828 between the pulley power chamber 3822 and the pulley waste chamber 3824 is opened to activate the fluid pulley and transfer the contents of the pulley power chamber 3822 to the pulley waste chamber 3824, thereby causing the transfer the contents of the separation/wash section 3808 (final PBMC payload) over a "weir" 3830 into the final chamber 3820 without passing though the orifice of a valve. Next, the NOV 3826 between the final chamber 3820 and the separation/wash section 3808 is closed to seal the final chamber.

Notably, in one application of IC NOVs, the cassette of FIG. 38 depicts a separation portion having multiple sections and incorporating IWC NOVs on either side of a skimmer dam or a middle section. In another application of IC NOVs, the cassette of FIG. 38 depicts the use of an IC NOV in series with another valve (e.g. a NCV). In this configuration, a fluidic channel may begin in a closed position, may then be opened by actuating the NCV, and may then be closed by actuating the IC NOV.

In embodiments, a modular cassette described herein may include any one or more of multiple valves, channels or chambers existing in multiple planes or layers. For example, a combination of chamber(s), valve(s) and channel(s) for one workflow or process may exist across a base portion of a cassette and in a cover plate. In this configuration, a sealing membrane may be sandwiched between the base portion and the cover plate. The sealing membrane may be a compliant member, may form or include a printed circuit or resistor array, and may include cutout portions to allow fluid to flow between the components of the different planes or layers.

In embodiments, two separate workflows or processes, such as two separate cassettes, may be sandwiched together. In this configuration, the sealing membrane may likewise be a compliant member, may form or include two or more printed circuits or resistor arrays, and may include cutout portions which allow fluid to flow between the planes or layers.

Optionally, several layers or planes of chamber(s), valve(s) and channel(s) may likewise be layered in to a single portion of a cassette, thereby abating the need for a sealing portion.

Figure 39:
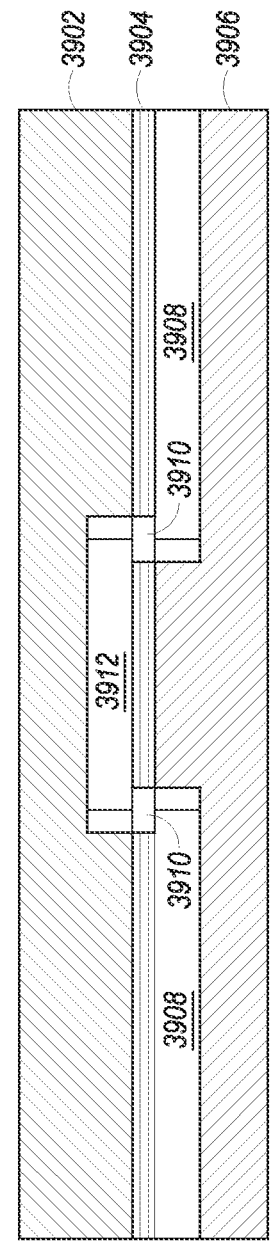
FIG. 39 illustrates a partial cross section of a cassette including two separate layers connected by a sealing layer according to an embodiment of the present application.
Figure 40A:
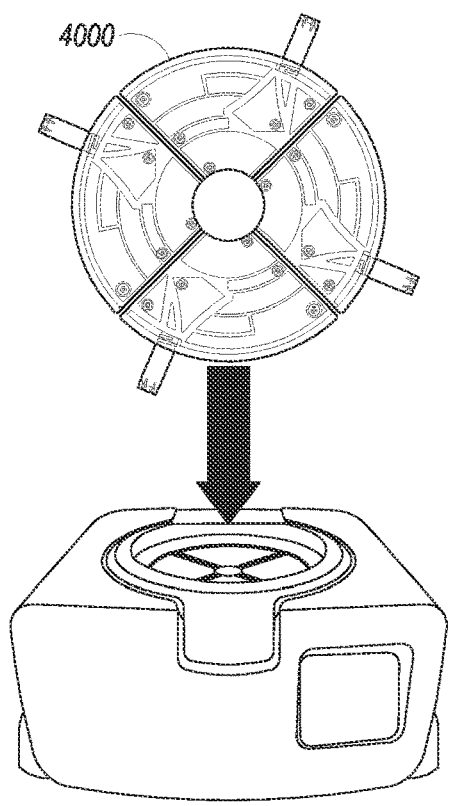
FIGS. 40A to 40D illustrate various cassette combinations according to an embodiment of the present application.
Figure 40B:
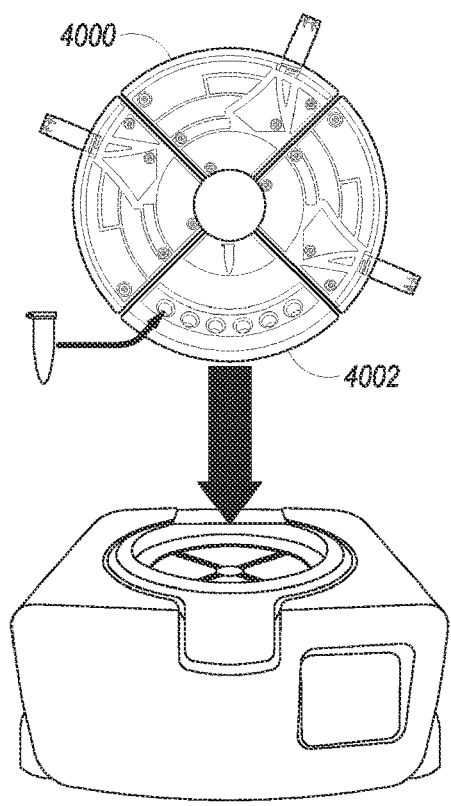
Figure 40C:
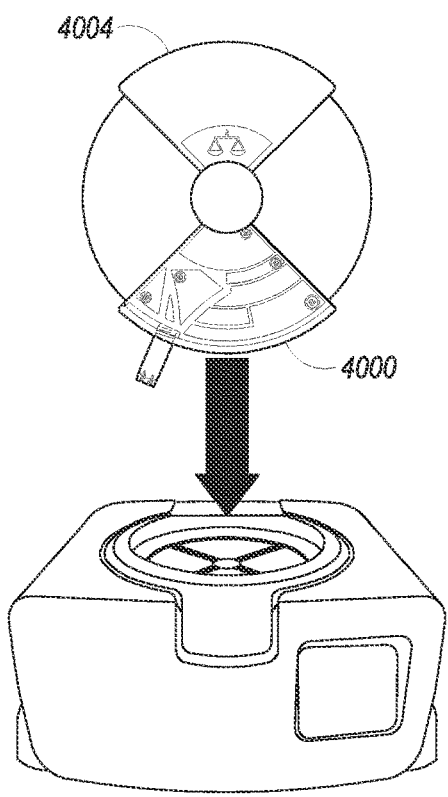
Figure 40D:
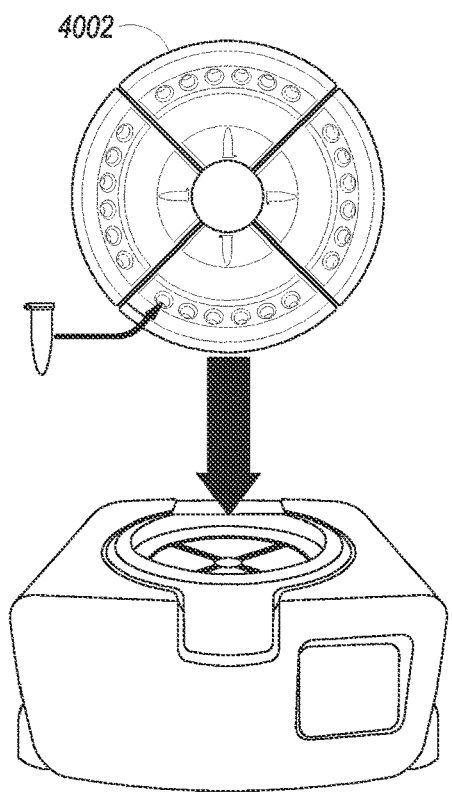

FIG. 39 illustrates a partial cross section of a cassette including two separate layers connected by a sealing layer in which cylindrical channels have been cut to allow for fluid flow between planes or layers.

As shown in FIG. 39, cassette 3900 includes a top layer 3902, a sealing layer 3904 and a bottom layer 3906. The bottom layer 3906 includes two channels 3908. The top layer 3902 includes a channel 3912. The sealing layer 3904 includes cutout portions 3910 which allow fluid to flow between the channel 3912 of the top layer 3902 and the channels 3908 of the bottom layer 3906.

FIGS. 40A to 40D illustrate various cassette combinations according to embodiments of the present application.

FIGS. 40A to 40D depict the use of between zero (0) and four (4) modular fluid separation cassettes. In embodiment 40A, each of the four (4) cassettes is a modular fluid separation cassette 4000. In embodiment 40B, three (3) of cassettes are modular fluid separation cassettes 4000 and one (1) cassette utilizes a traditional centrifugation design 4002 which houses one or more separation tubes in a fixed-angle or swinging bucket configuration. In embodiment 40C, only two (2) cassettes are used, and are arranged so as to be counterbalanced vis-a-vis one another. In this embodiment, a modular fluid separation cassette 4000 is shown opposite a "dummy" cassette 4004. In embodiment 40D, each modular cassette is a traditional cassette 4002; no modular fluid separation cassette or dummy cassette is included.

As shown in FIGS. 40A to 40D, each cassette is modular. The benchtop-style fluid separation system may include any combination of the modular fluid separation cassette 4000, the traditional cassette 4002 and the "dummy" cassette 4004. The dummy cassette may comprise any suitable material, such as a properly weighted rubber or other material that would be recognized by those skilled in the art as being a suitable counterbalance.

As shown in FIGS. 40A to 40D, each modular fluid separation cassette 4000 is designed to form a "wedge" shape which occupies only a percentage of a disk in a circumferential direction about the axis of rotation of the rotor assembly. For example, in embodiment 40A, a centrifuge may hold four (4) modular fluid separation cassettes 4000 (as shown) aligned radially or circumferentially about the rotor assembly relative to its axis of rotation, each cassette occupying approximately 25% of the circumferential area of the rotor assembly. In other embodiments, a fewer or greater number of modular fluid separation cassettes may be used.

In further embodiments, two or more modular fluid separation cassettes may also be affixed to, or placed adjacent to, one another so as to be scalable in a vertical or "stackable" direction (not shown) relative to an axis of rotation. This configuration may be referred to colloquially as a "pancaked" configuration. In such embodiments, an increased number of small volume modular fluid separation cassettes having a capacity to process blood samples of between 1 ml-10 ml may be processed simultaneously. There exist several advantages to this type of configuration, such as the ability to process several discreet small volume samples concurrently in an emergency or disaster scenario, or on a battleground, each of which potentially involving a high volume of donors and requiring rapid assessment.

FIGS. 41A and 41B illustrate a cross sectional comparison of two modular fluid separation cassettes according to embodiments of the present application.

Referring to FIGS. 41A and 41B, the modular fluid separation cassette may be configured to process a sample of liquid having a volume of 1 ml-10 ml, as in embodiment 41A, or configured to process a sample of liquid from 40 ml-125 ml, as in embodiment 41B. That is, the modular fluid separation cassette is scalable in size. In embodiments, an individual modular fluid separation cassette may be increased in its capacity to process a greater volume of fluid. Increasing the size of the modular fluid separation cassette in the thickness direction (i.e., the direction perpendicular to the centrifugal force and parallel to the axis of rotation) does not substantially change the fluid dynamics of the liquid during centrifugation. This is because, as noted in the explanation and equations in the background section, an increase in radius of the modular fluid separation cassette would be required to increase the centrifugal forces exerted on the fluid. Here, changing the volume of the modular fluid separation cassette in the thickness direction does not require an increase in radius of the cassette, and thus does not result in a substantial change in the amount of centrifugal force acting upon the fluid. Various other cassette shapes and sizes are also contemplated in this disclosure, and this disclosure is in no way limited to any specific examples provided herein.

Figure 42:
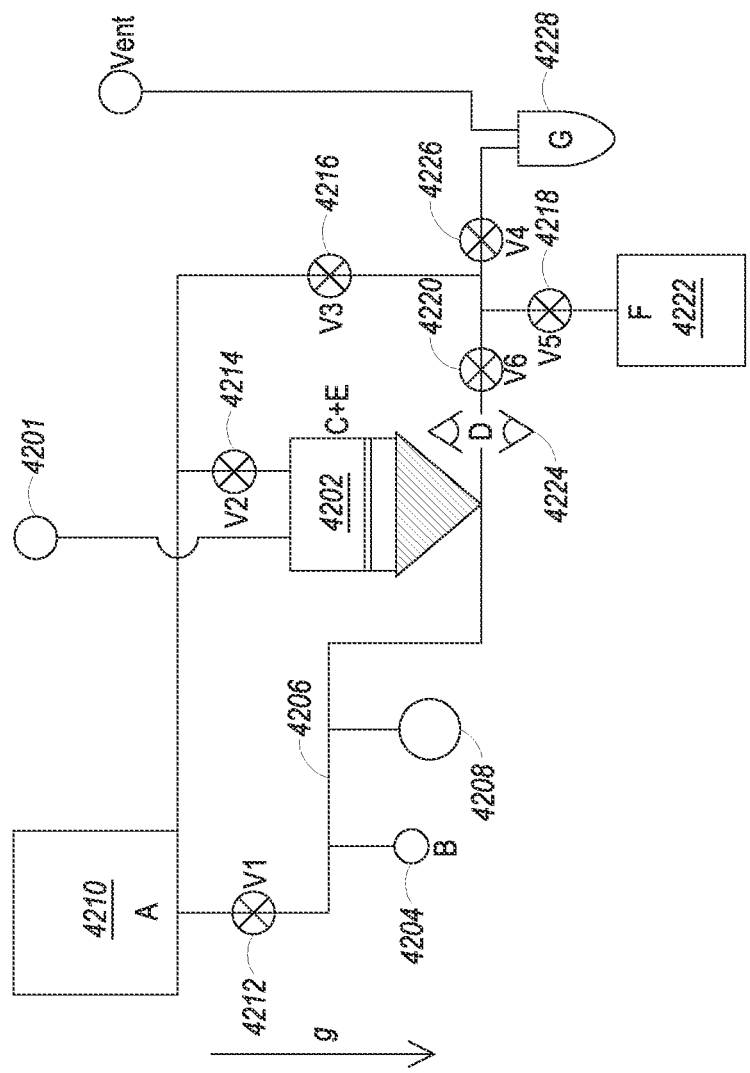
FIG. 42 is a schematic diagram of a fluid separation processes according to an embodiment of the present application.
Figure 43:
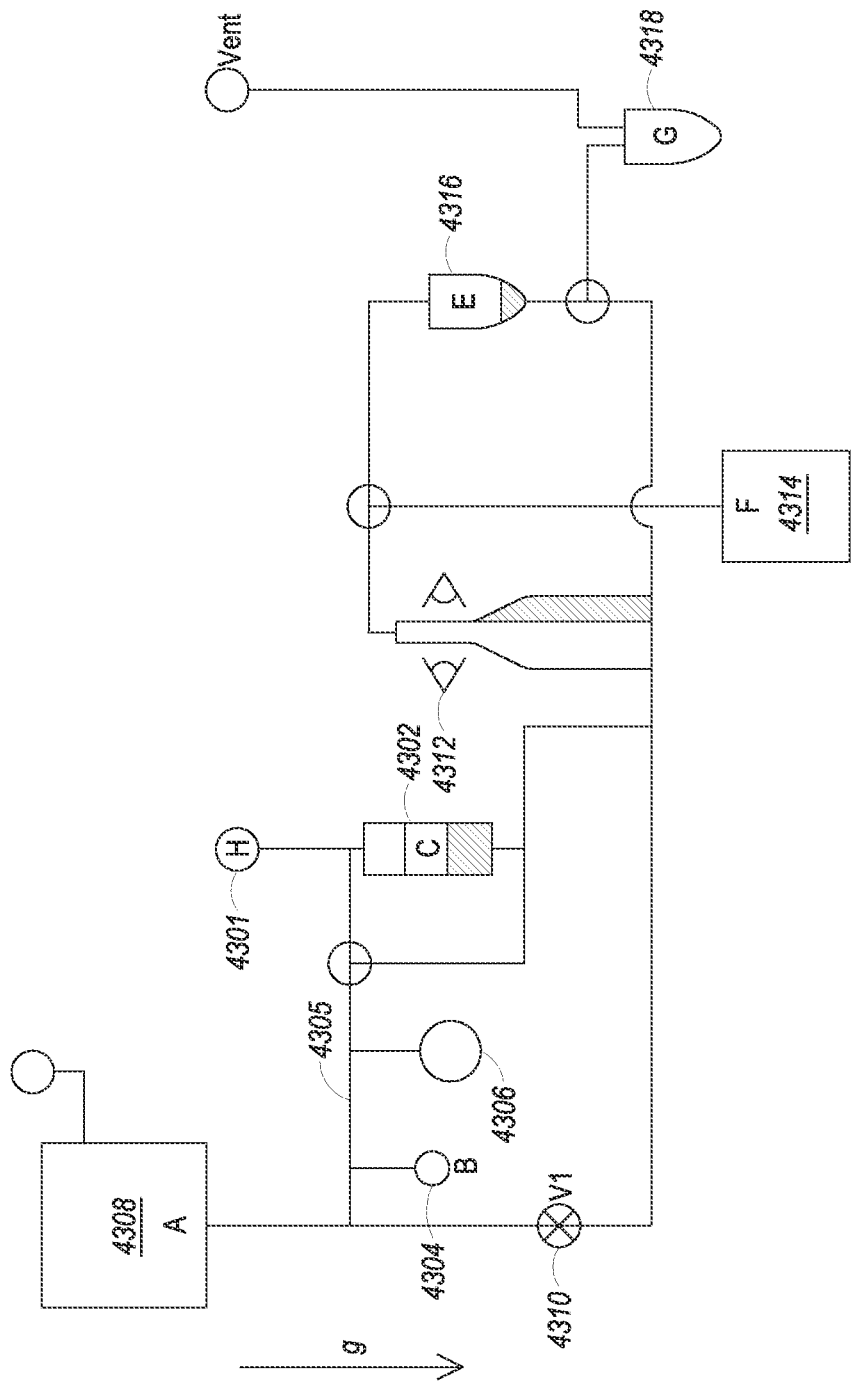
FIG. 43 is a schematic diagram of another fluid separation processes according to an embodiment of the present application.
Figure 44:
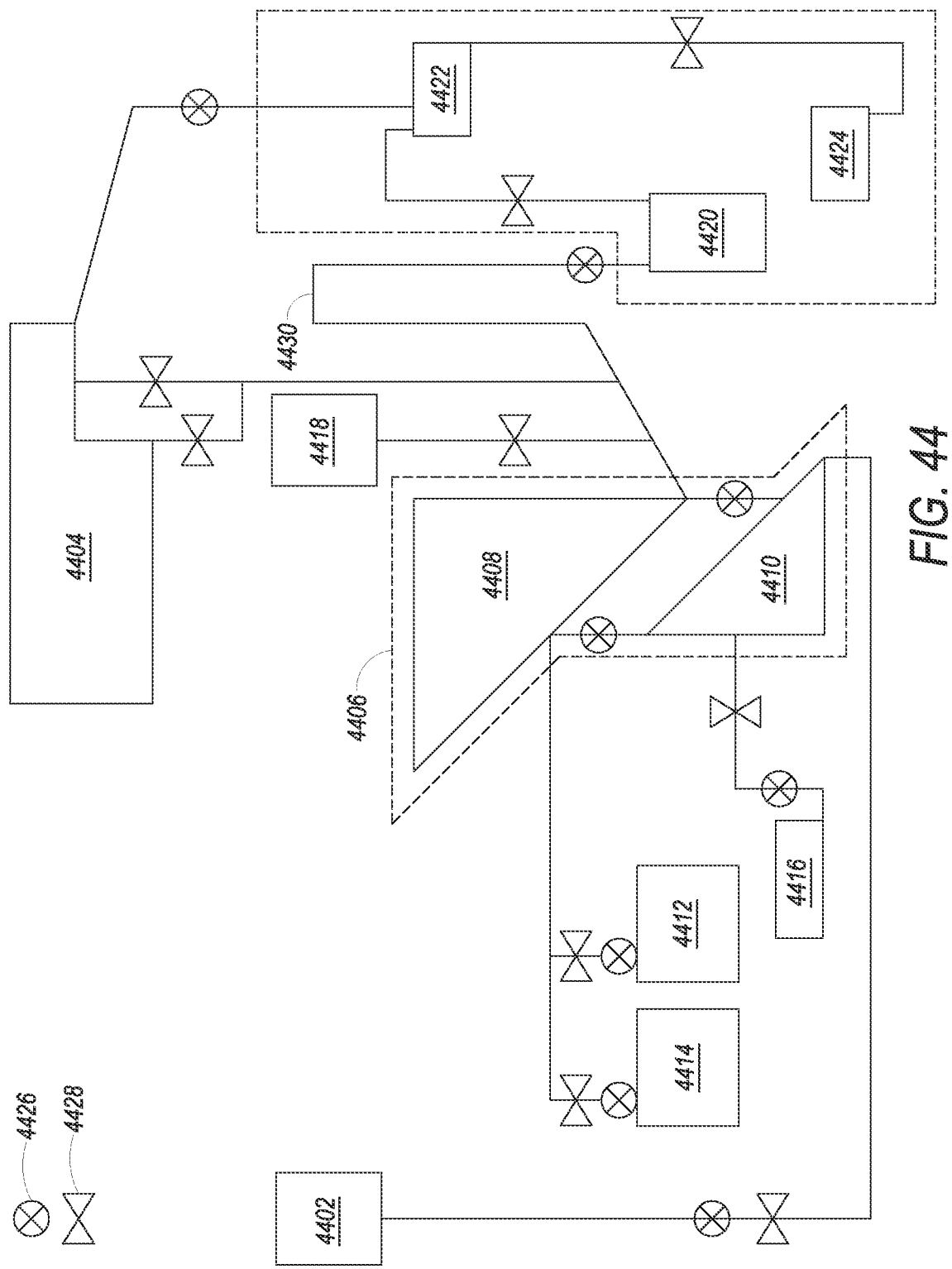
FIG. 44 is a schematic diagram of yet another fluid separation processes according to an embodiment of the present application.

FIG. 42 to FIG. 44 are schematic diagrams of fluid separation processes according to embodiments of the present application.

Although specific sequences and cassette components may be described below in connection with the schematic diagrams of FIG. 43 to FIG. 45, the present application is not limited thereto. Those skilled in the art may appreciate various cassette design and process variations that may accomplish the same or similar ends. Likewise, the steps described below are not limited to a particular cassette type, and may occur in a wedge type cassette, in a disk type cassette or in any other cassette type (see, e.g., appendix A). The steps described below may also occur across two or more cassettes or in two or more separate systems, and multiple processes may occur on the same cassette.

Referring to FIG. 42, first, whole blood is loaded in to separation chambers C and E 4202 through port 4201. Next, density gradient media is loaded into media chamber B 4204 and calibrated to fill a channel length 4206 and to overflow into a density gradient media sink 4208. Next, Phosphate-Buffered Saline (PBS) is loaded into a buffer solution chamber at point A 4210. Next, valve 1 (4212) is opened to push the density gradient media under the whole blood in chamber C 4202. Next, the centrifuge is hard spun to separate the Red Blood Cells (RBCs) from the plasma; next, valves 2 (4214), 3 (4216), 5 (4218) and 6 (4220) are opened to push RBCs to waste chamber F 4222 until density gradient media is detected at point D 4224. Next, valves 2 (4214) and 5 (4218) are closed and valve 3 (4216) is opened to push PBMCs back to C and E 4202. Next, valve 3 (4216) is closed and valves 1 (4212), 2 (4214) and 5 (4218) are open (valve 1 (4212) is opened to admit rinse to bottom of C and E), and plasma, platelets and density gradient media are directed to waste chamber F 4222. Next, valves 1 (4212) and 5 (4218) are closed and valves 2-4 (4214; 4216; and 4226 respectively) and 6 (4220) are opened to direct PBMCs to chamber G 4228.

Referring to FIG. 43, first, whole blood is loaded into separation chamber C 4302 from port H 4301. Next, density gradient media is loaded into a media chamber B 4304 and calibrated to fill a channel length 4305 and to overflow into a density gradient media sink 4306. Next, PBS is loaded into a buffer solution chamber A 4308. Next, the centrifuge is spun and the PBS flows through B 4304 to push density gradient media under the whole blood in chamber C 4302. Next, valve 1 4310 opens to admit the PBS to the top of chamber C 4302. Next, separated fluid (which flows in order of RBCs, density gradient media, MNCs, plasma) flows through a thin channel area which lengthens the interface and allows for effective valve actuation based on feedback from interface detection means 4312. Next, RBCs are directed to waste area F 4314. Next, some density gradient media, MNCs and plasma are directed to wash chamber E 4316. Next, PBS is directed to the bottom of chamber E 4316 to wash away density gradient media and plasma. Next, the centrifuge is "hard spun" with no fluid flow. Next, PBS is directed to the top of E 4316, pushing the MNCs to collection area G 4318.

FIG. 44 is a schematic view of the cassette depicted in FIG. 38.

As shown in FIG. 44, the schematic view of the cassette shown in FIG. 38 includes a first separation media chamber 4402; a wash reservoir 4404; a two-part separation portion 4406 including a separation/wash section or chamber 4408 and a separation/heavy waste section or chamber 4410; a first light waste chamber 4412; a second light waste chamber 4414; a plasma chamber 4416; a media chamber 4418; a final chamber 4420; a pulley power chamber 4422; a pulley waste chamber 4424; various NOVs 4426 and various NCVs 4428.

To use this configuration, whole blood is loaded into the upper section of the separation chamber 4408. Density gradient media is loaded into the separation media chamber 4402. Phosphate-Buffered Saline (PBS) or other cell washing media is loaded into the wash reservoir 4404. Cell suspension or storage media is loaded into the media chamber 4418. As the cassette is spun in a centrifuge, the pulley power chamber 4422 is loaded with fluid from the wash reservoir 4404; whole blood flows into the separation/heavy waste section 4410 of the two-part separation portion 4406 from the separation/wash section 4408, leaving the separation/wash section 4408 empty; and blood cells in the separation/heavy waste section 4410 sediment and separate from plasma. The NCV 4428 between the separation/heavy waste section 4410 and plasma chamber 4416 is then opened to transfer some of the plasma layer from the separation/heavy waste section 4410 into the plasma chamber 4416. Next, the NCV 4428 between separation/heavy waste section 4410 and plasma chamber 4416 is closed to block the fluid pathway. Next, the NCV 4428 between the separation media chamber 4402 and the separation/heavy waste section 4410 is opened to push density gradient media under the remaining whole blood in the separation/heavy waste section 4410. Next, the NOV 4426 between the separation media chamber 4402 and the separation/heavy waste section 4410 is closed to block the fluid pathway. Next, time is elapsed to separate mononuclear cells (PBMCs) from red blood cells (RBCs) and granulocytes, with PBMCs rising into the separation/wash section 4408 and RBCs and granulocytes sedimenting into the separation/heavy waste section 4410. Next, the NOVs 4426 between the separation/heavy waste section 4410 and the separation/wash section 4408 of the two-part separation portion 4406 are closed to isolate the sections from one another. Next, NCV 4428 valve between wash reservoir 4404 and the separation/wash section 4408 is opened to suspend the contents of the separation/wash section 4408 (now the wash chamber) in wash media. Next, time is elapsed as cells sediment in separation/wash section 4408 (i.e., wash chamber). Next, the NCV 4428 between the wash chamber 4408 and the light waste chamber 4412 is opened to drain supernatant fluid from the wash chamber 4408 into the light waste chamber 4412 (LW1). Next, the NOV 4426 between the wash chamber 4408 and the light waste chamber 4414 is closed. Next, the NCV 4428 between the wash reservoir 4404 and the separation/wash section 4408 is opened to suspend the contents of the wash chamber 4408 a second time, and time is elapsed as cells sediment. Next, the NCV 4428 between the wash chamber 4408 and the light waste chamber 4414 (LW2) is opened to drain supernatant fluid from the Wash chamber into LW2. Next, the NOV 4426 between the wash chamber 4408 and the light waste chamber 4414 (LW2) is closed. Next, the NCV 4428 between the separation/wash section 4408 and the media chamber 4418 is opened to suspend the contents of the wash chamber in suspension/storage media. Next, the valve between the wash reservoir 4404 and the pulley power chamber 4422 is closed to isolate the Wash Reservoir from the pulley power chamber 4422. Next, the NCV 4428 between the final chamber 4420 and the pulley power chamber 4422 is opened to open the vent connecting the final chamber 4420 and the pulley power chamber 4422. Next, the NCV 4428 between the pulley power chamber 4422 and the pulley waste chamber 4424 is opened to activate the fluid pulley and transfer the contents of the pulley power chamber 4422 to the pulley waste chamber 4424, thereby causing the transfer the contents of the separation/wash section 4408 (final PBMC payload) over a "weir" 4430 into the final chamber 4420 without passing though the orifice of a valve. Next, the NOV 4426 between the final chamber 4420 and the separation/wash section 4408 is closed to seal the final chamber.

The pulley concept in this configuration can be rearranged such that instead of using a reduced pressure to transfer the payload up and over the "weir" 4430, an increased pressure in the separation/wash section 4408 can "push" the transfer by using a compression of air through filling a non-vented chamber (i.e. a pulley waste) connected to the separation/wash section 4408.

As shown in the schematic diagrams of FIG. 42 to FIG. 44, the PBS is loaded and begins at a high or "inboard" point in the G-field. The waste is deposited at a lower or more "outboard" point in the G-field. This is accomplished by controlling the flow of fluid in the G-field during centrifugation. All functions in the modular fluid separation cassette occur due to the proper design, positioning and orientation of each of the chambers, valves, fluid channels, sensors, heating elements and other components within the cassette, such that monitoring and control of each of the cassette components, the rotation time and the rotation speed result in an effective fluid separation. Various modifications and optimizations regarding the design, location and orientation of the above features and method steps will be understood by those in the art to be encompassed by this description.

Figure 45:
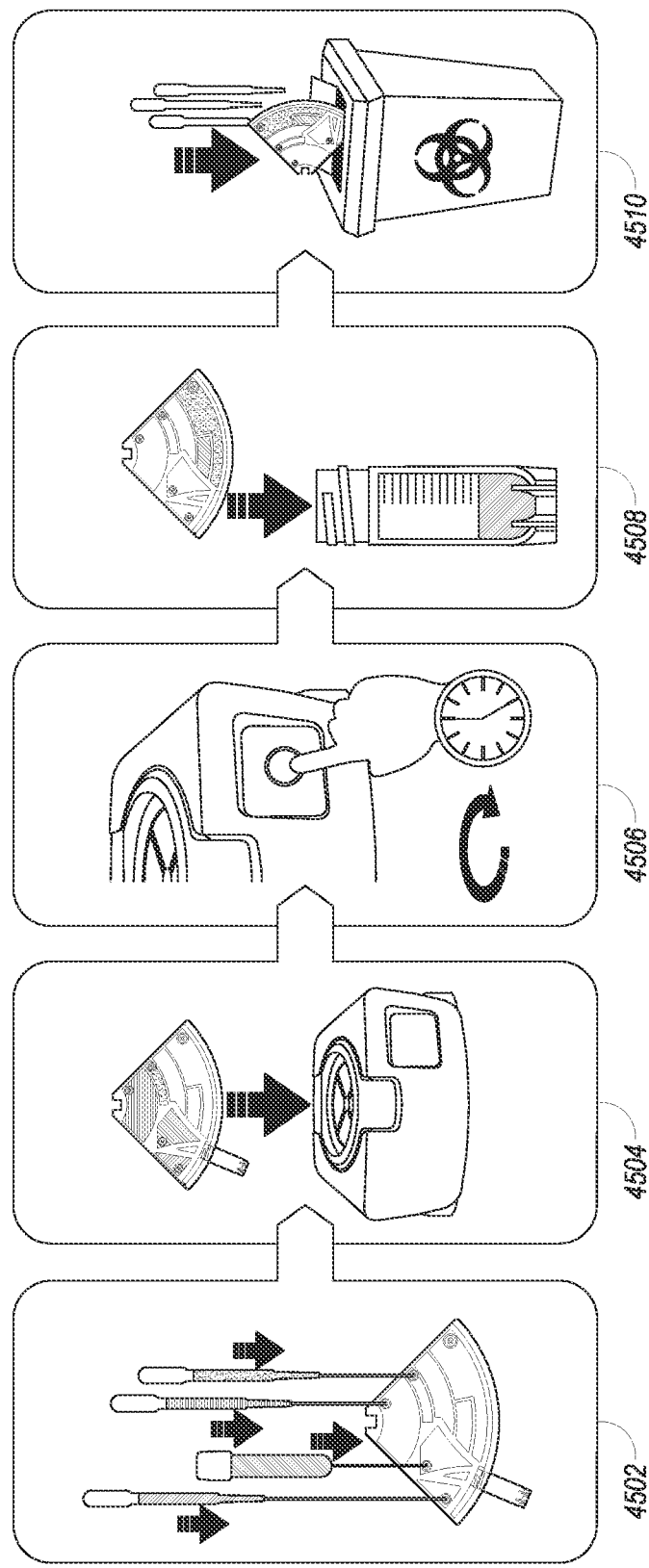
FIG. 45 is a flow diagram of a workflow according to an embodiment of the present application.

FIG. 45 is a flow diagram of a workflow according to an embodiment of the present application.

Referring to FIG. 45, a modular fluid separation cassette is prepared in step 4502; the modular fluid separation cassette is loaded into the separator in step 4504; the separator is started in step 4506; a packaged PBMC sample is retrieved in step 4508; and the modular fluid separation cassette is disposed of in step 4510.

The workflow shown in FIG. 45 requires the use of the systems and components described in the present application, and accordingly represents a significant advance over conventional techniques used in the separation of PBMC from whole blood for the variety of reasons provided throughout this disclosure. Among those enumerated advantages is a demonstrable yield increase of 25% vis-a-vis traditional manual procedures. Such yield increases may be attributable, in part, to the perpetual exposure of blood components in the modular fluid separation cassette to the G-field throughout centrifugation, thereby eliminating the potential for contamination in the final sample that is caused by the mixing of components at zero G.

The automation of embodiments of the various systems and components described herein using computer processing may further allow for more efficient and dynamical sample and process tracking than is currently achievable using manual or conventional processes. For instance, embodiments may include adhesive RFID tags, bar codes, or the like, alongside networked software and hardware to physically track machines and samples. Automation may also be beneficial in using hardware and software to better track and control processes to ensure the integrity of the sampling procedure, to alert operators to potential problems and to otherwise monitor and record process progress, to generate reports, and so on.

A further advantage to embodiments described herein is that yield may be produced in a "ready-to-go" state in which a final product is immersed in media immediately upon separation. In the case of a cassette including a removable collection vessel, such media may be included in the collection vessel. In cases without a removable collection vessel, a collection chamber within the cassette may include the media. Such embodiments contrast with traditional procedures that require an operator to place the yield into media at a time after collection. Embodiments herein thus extend the time period during which cells are viable after separation and collection.

In various embodiments, operation of the system or its individual components may be controlled by one or more processors included therein, and may advantageously comprise a plurality of embedded computer processors that are part of a computer system. The computer system may also include components that allow a user to interface with the computer system, including for example, memory and storage devices (RAM, ROM (e.g., CD-ROM, DVD), magnetic drives, optical drives, flash memory,); communication/networking devices (e.g., wired such as modems/network cards, or wireless such as Wi-Fi); input devices such keyboard(s), touch screen(s), camera(s), and/or microphone(s); and output device(s) such as display(s), and audio system(s). In order to assist the operator of the centrifugation systems described herein with various aspects of its operation, such embodiments may include a graphical user interface with a display that includes an interactive touch screen.

Notwithstanding the various particular embodiments enumerated throughout this disclosure, those skilled in the art will appreciate that a variety of modifications and optimizations could be implemented for particular applications. It is to be understood that this application is not limited to any configuration described herein. For instance, it may be desirable to use a lesser or greater number of modular fluid separation cassettes in a centrifuge. That is, in a particular scenario, six (6) balanced modular fluid separation cassettes may be implemented in which each modular fluid separation cassette comprises 60 degrees of a circumferential area of a rotor assembly. Likewise, a scenario may exist in which three (3) balanced modular fluid separation cassettes would be implemented, whereby each modular fluid separation cassette comprises 120 degrees of a circumferential area of the rotor assembly. Similarly, modular fluid separation cassettes including any combination of front-loaded, back-loaded, NOV and NCV valve configurations may be desirable. Likewise, the number of valves may be adjusted for a particular application. Pumpless flow control means as described herein may also be variously incorporated for particular applications. Additionally, the present application is not limited to the separation of blood. That is, the principles of the present application may be applicable to the separation or removal of particular constituents from many fluids. Accordingly, various modifications and changes may be made in the arrangement, operation, and details of the methods and systems of the present application which will be apparent to those skilled in the art.

What is claimed is:

1. A modular cassette for separating a composite fluid into at least two component parts thereof during centrifugation, the modular cassette comprising:
   a housing defining a fluid inlet, a fluid outlet, and a chamber for fluid separation;
   a fluidic channel configured to provide fluid communication between at least two components of the modular cassette;
   a heat expanding valve including:
      a flow pathway including undulations configured to facilitate closing of the fluidic channel, wherein the heat expanding valve occludes one or more of the undulations of the flow pathway to close the fluidic channel; and
      a heating element configured to actuate the heat expanding valve.

2. The modular cassette of claim 1, wherein the undulations are semicircular undulations.

3. The modular cassette of claim 1, wherein the undulations are arranged such that a width of the flow pathway varies along at least one section of the flow pathway.

4. The modular cassette of claim 1, wherein the heat expanding valve is a wax valve.

5. The modular cassette of claim 4, wherein the heat expanding valve includes a volume of wax sufficient to fill and occlude one or more of the undulations of the flow pathway to close the fluidic channel.

6. The modular cassette of claim 4, wherein the wax valve comprises an injection cavity.

7. The modular cassette of claim 6, wherein the injection cavity comprises at least one injection port.

8. The modular cassette of claim 7, wherein the injection cavity further comprises at least one vent.

9. The modular cassette of claim 8, wherein the injection cavity further comprises an extended portion configured to accept a volume of molten wax equal to a volume of at least part of the flow pathway.

10. The modular cassette of claim 1, wherein the undulations are arranged on opposing sides of the flow pathway.

11. The modular cassette of claim 10, wherein each of the undulations includes a concave surface, and concave surfaces of opposing pairs of the undulations face one another at an interior of the flow pathway.

* * * * *